(12) United States Patent
Lincker et al.

(10) Patent No.: US 9,366,906 B2
(45) Date of Patent: Jun. 14, 2016

(54) PHOTOREACTIVE COMPOUNDS

(75) Inventors: Frederic Lincker, Schiltigheim (FR);
Izabela Bury S. Pires, Allschwil (CH);
Sabrina Chappellet, Village-Neuf (FR);
Patricia Scandiucci De Freitas, Basel (CH); Mohammed Ibn-Elhaj, Allschwil (CH); Qian Tang, Oberwil (CH); Satish Palika, Zofingen (CH); Masato Hoshino, Basel (CH); Jean-Francois Eckert, Kientzville (FR)

(73) Assignee: ROLIC AG, Zug (CH)

( * ) Notice: Subject to any disclaimer, the term of this patent is extended or adjusted under 35 U.S.C. 154(b) by 0 days.

(21) Appl. No.: 14/237,270

(22) PCT Filed: Aug. 7, 2012

(86) PCT No.: PCT/EP2012/065380
§ 371 (c)(1),
(2), (4) Date: Feb. 5, 2014

(87) PCT Pub. No.: WO2013/026691
PCT Pub. Date: Feb. 28, 2013

(65) Prior Publication Data
US 2014/0192305 A1 Jul. 10, 2014

(30) Foreign Application Priority Data

| Aug. 25, 2011 | (EP) | 11178750 |
| Dec. 22, 2011 | (EP) | 11195086 |

(51) Int. Cl.
| C09K 19/00 | (2006.01) |
| G02F 1/1337 | (2006.01) |
| C09K 19/56 | (2006.01) |
| C07C 255/41 | (2006.01) |
| C07D 307/81 | (2006.01) |
| C07D 317/46 | (2006.01) |
| C07D 319/08 | (2006.01) |
| C09K 19/04 | (2006.01) |

(52) U.S. Cl.
CPC ........ *G02F 1/133711* (2013.01); *C07C 255/41* (2013.01); *C07D 307/81* (2013.01); *C07D 317/46* (2013.01); *C07D 319/08* (2013.01); *C09K 19/56* (2013.01); *C09K 2019/0448* (2013.01); *C09K 2019/0496* (2013.01); *Y10T 428/1005* (2015.01)

(58) Field of Classification Search
CPC ............ C09K 19/56; C09K 2019/0496; G02F 1/133711; C07C 255/41; C07D 317/46; C07D 319/08; Y10T 428/1005; Y10T 428/1014; Y10T 428/1018; Y10T 428/1023

USPC ............. 428/1.2, 1.25, 1.26, 1.27, 1.28; 349/123, 127; 430/30, 20; 524/548, 524/549; 558/402
See application file for complete search history.

(56) References Cited

U.S. PATENT DOCUMENTS

| 3,080,418 | A | 3/1963 | Sullivan |
| 5,539,079 | A | 7/1996 | Cramer et al. |
| RE36,625 | E | 3/2000 | Herr et al. |
| 6,107,427 | A | 8/2000 | Herr et al. |
| 6,201,087 | B1 | 3/2001 | Herr et al. |
| 6,340,506 | B1 | 1/2002 | Buchecker et al. |
| 6,632,909 | B2 | 10/2003 | Buchecker et al. |
| 6,649,230 | B1 | 11/2003 | Seiberle et al. |
| 6,831,148 | B2 | 12/2004 | Buchecker et al. |
| 6,833,421 | B1 | 12/2004 | Marck |
| 6,887,534 | B2 | 5/2005 | Nakata et al. |
| 7,491,752 | B2 | 2/2009 | Marck et al. |
| 7,514,514 | B2 | 4/2009 | Buchecker et al. |
| 7,687,118 | B2 | 3/2010 | Cherkaoui et al. |
| 7,750,185 | B2 | 7/2010 | Marck et al. |
| 7,959,990 | B2 | 6/2011 | Cherkaoui et al. |
| 2003/0039768 | A1 | 2/2003 | Buchecker et al. |
| 2005/0288426 | A1 | 12/2005 | Studer et al. |
| 2008/0274304 | A1 | 11/2008 | Cherkaoui et al. |
| 2009/0290109 | A1 | 11/2009 | Lee et al. |
| 2010/0266821 | A1 | 10/2010 | Bury et al. |
| 2011/0065859 | A1 | 3/2011 | Bury et al. |

FOREIGN PATENT DOCUMENTS

| DK | 1 078 120 A | 9/1958 |
| EP | 1 764 405 A1 | 3/2007 |
| EP | 1818354 A2 | 8/2007 |
| GB | 872355 | 7/1961 |
| JP | 58-109479 A | 6/1983 |
| JP | 60-013740 A | 1/1985 |
| JP | 04458299 B2 | 4/2010 |
| WO | 00/59966 A1 | 10/2000 |
| WO | 01/53384 A1 | 7/2001 |
| WO | 2004/060861 A2 | 7/2004 |
| WO | 2008/135131 A1 | 11/2008 |
| WO | 2009/051207 A1 | 4/2009 |

OTHER PUBLICATIONS

"Table of Substituent Effects", Retrieved from webside of Ohio Northern University, "www2.onu.edu", Feb. 2015.*
International Search Report for PCT/EP2012/065380 dated Sep. 17, 2012.

* cited by examiner

*Primary Examiner* — Ruiyun Zhang
(74) *Attorney, Agent, or Firm* — Sughrue Mion, PLLC

(57) ABSTRACT

The present invention relates to photoreactive compounds that are particularly useful in materials for the alignment of liquid crystals.

18 Claims, No Drawings

PHOTOREACTIVE COMPOUNDS

CROSS REFERENCE TO RELATED APPLICATIONS

This application is a National Stage of International Application No. PCT/EP 2012/065380 filed Aug. 7, 2012, claiming priority based on European Patent Application No. 11178750.3, filed Aug. 25, 2011, and European Patent Application No. 11195086.1, filed Dec. 22, 2011, the contents of all of which are incorporated herein by reference in their entirety.

The present invention relates to photoreactive compounds that are particularly useful in materials for the alignment of liquid crystals.

Liquid crystal devices are more and more used in many different applications. Examples are optical or electro-optical elements, such as optical films, in particular polarizing films and retardation films, especially 3-D-retarder films which can be used for liquid crystal displays (LCDs), decorative applications or security devices, such as for preventing forgery, counterfeiting and copying. In all these applications the liquid crystals possess specific orientations, which are for example accessible by alignment layers. Photoalignment layers are preferred ones due to their economic manufacturing processes, wherein they are accessible in nearly quantitative yields. Therefore, there is a huge interest from the market and industries to have photoalignment materials which can be used in these economic photoaligning processes and in addition, give access to the envisaged good optical or electro-optical properties in the different applications.

Thus the present invention relates in a first aspect to a compound comprising a terminal group of formula (I), preferably a terminal group of formula (Ia)

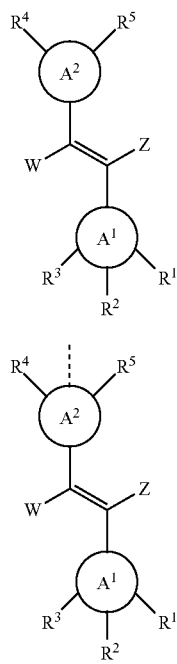

wherein:
the doted line means a linkage of the terminal group to the residue of the compound;
$A^1$ and $A^2$ each independently are a ring system of 5 to 40 atoms, wherein each ring system includes at least one unsaturation directly connected via electron conjugation ($\pi$-$\pi$ bonding) to the double bond shown in formula (I); and wherein $A^2$ is linked to a polymerizable group by a single bond or at least one spacer unit;

$R^1$ is hydrogen, a substituent L or a straight-chain or branched, substituted or unsubstituted $C_1$-$C_{12}$alkyl, in which one or more C-atom, CH— or $CH_2$— group is unreplaced or replaced by a linking group; preferably $R^1$ is hydrogen or —$X^1$—$R^6$, wherein $R^6$ is hydrogen, —$CF_3$, $C_1$-$C_6$alkylen-aryl, aryl, alicyclic group, $C_1$-$C_{12}$alkyl, in which one or more C-atom, CH— or $CH_2$— group may be replaced by a linking group, and wherein $X^1$ is —O—, —S—, Se, —N—, —NH— and —$NR^7$, wherein $R^7$ is a hydrogen atom or a straight-chain or branched alkyl or alkylene group, having from 1 to 12, more preferably from 1 to 6 carbon atoms, wherein one or more, preferably non-adjacent —$CH_2$— groups independently unreplaced or replaced by a linking group, preferably selected from —O—, —CO—, —CO—O—, —O—CO—, —C=C—, —C≡C; more preferably $R^7$ is a hydrogen atom or methyl; or preferably $R^1$ is an optionally substituted $C_1$-$C_6$alkyl, or a polymerizable group; and more preferably $R^1$ is hydrogen;

and wherein if
W is hydrogen and Z is an electron withdrawing group, then $R^4$, $R^5$ are hydrogen, and $R^2$ and $R^3$ are independently from each other an electron-donating single substituent, preferably these electron-donating single substituents are in meta-position to each other; or $R^2$ and $R^3$ form together the residue of an electron-donating ring which is condensed to ring $A^1$; or if W is hydrogen and Z is an electron withdrawing group, then $R^4$, $R^5$ are independently from each other hydrogen, a substituent L, or an electron-donating single substituent, with the proviso that at least one $R^4$ or $R^5$ is a substituent L, or an electron-donating single substituent; or $R^4$, $R^5$ form together the residue of an electron-donating ring which is condensed to ring $A^2$; and, $R^2$ and $R^3$ form together the residue of an electron-donating ring which is condensed to ring $A^1$; or $R^4$ is —O—$C_2$-$C_6$alkyl, such as —O-ethyl, —O-propyl, —O-butyl, —O-pentyl, —O-hexyl, $R^5$ is hydrogen and $R^2$ and $R^3$ are hydrogen or an electron-donating single substituent, preferably both $R^2$ and $R^3$ are an electron-donating single substituent; or $R^4$, $R^5$ are independently from each other a substituent L, an electron-donating single substituent, or hydrogen; and $R^2$ and $R^3$ are independently from each other —O—$C_2$-$C_6$alkyl, such as —O-ethyl, —O-propyl, —O-isopropyl, —O-butyl, —O-tert-butyl, —O-sec-butyl, —O-pentyl, —O-isopentyl, —O-hexyl; or $R^4$, $R^5$ are independently from each other a —O—$C_2$-$C_6$alkyl, such as —O-ethyl, —O-propyl, —O-isopropyl, —O-butyl, —O-tert-butyl, —O-sec-butyl, —O-pentyl, —O-isopentyl, —O-hexyl or hydrogen, and $R^2$ and $R^3$ are independently from each other —O—$C_2$-$C_6$alkyl, such as —O-ethyl, —O-propyl, —O-isopropyl, —O-butyl, —O-tert-butyl, —O-sec-butyl, —O-pentyl, —O-isopentyl, —O-hexyl; or $R^4$, $R^5$ are independently from each other a substituent L, an electron-donating single substituent, preferably $R^4$, $R^5$ are O—$C_1$-$C_6$alkyl, more preferably —O-methyl, —O-ethyl, and $R^2$ and $R^3$ are independently from each other —O—$C_1$-$C_6$alkyl, such as —O-methyl, —O-ethyl, —O-propyl, —O-isopropyl, —O-butyl, —O-tert-butyl, —O-sec-butyl, —O-pentyl, —O-isopentyl, —O-hexyl;

or if W is an electron withdrawing group and Z is hydrogen, then
R$^4$, R$^5$ are independently from each other hydrogen, a substituent L, an electron-donating single substituent, or R$^4$, R$^5$ form together the residue of an electron-donating ring which is condensed to ring A$^2$ or hydrogen, and R$^2$ and R$^3$ are independently from each other an electron-donating single substituent, or form together the residue of an electron-donating ring which is condensed to ring A$^1$;
most preferred is
W is hydrogen and Z is an electron withdrawing group, then
R$^4$, R$^5$ are hydrogen, and R$^2$ and R$^3$ are independently from each other an electron-donating single substituent, preferably these electron-donating single substituents are in meta-position to each other; or
R$^2$ and R$^3$ form together the residue of an electron-donating ring which is condensed to ring A$^1$; or
if W is hydrogen and Z is an electron withdrawing group, then
R$^4$, R$^5$ are independently from each other hydrogen, a substituent L, or an electron-donating single substituent, with the proviso that at least one R$^4$ or R$^5$ is a substituent L, or an electron-donating single substituent; or R$^4$, R$^5$ form together the residue of an electron-donating ring which is condensed to ring A$^2$; and,
R$^2$ and R$^3$ form together the residue of an electron-donating ring which is condensed to ring A$^1$; or
or if W is an electron withdrawing group and Z is hydrogen, then
R$^4$, R$^5$ are independently from each other hydrogen, a substituent L, an electron-donating single substituent, or R$^4$, R$^5$ form together the residue of an electron-donating ring which is condensed to ring A$^2$ or hydrogen, and R$^2$ and R$^3$ are independently from each other an electron-donating single substituent, or form together the residue of an electron-donating ring which is condensed to ring A$^1$.

In a further preferred embodiment the substituents R$^2$ and R$^3$ are independently from each other and an electron-donating ring which is condensed to ring.

The wording "polymerizable group" as used in the context of the present invention refers to a functional group that can be subjected to polymerization (optionally with other comonomers) to yield an oligomer, dendrimer or polymer according to the present invention. For a person skilled in the art it will be obvious which functional groups are intended for any specific polymer. Thus for example in case of "imid monomer" as the indicated polymer backbone group it is obvious to a person skilled in the art that the actual monomer units for polymerization to yield a polyimid are e.g. diamines and dianhydrides. Similarly regarding "urethane monomer" the actual monomer units are diols and diisocyanates.

In a further preferred embodiment the polymerizable group is "D", which is preferably selected from acrylate, methacrylate, 2-chloroacrylate, 2-phenylacrylate, optionally N-lower alkyl substituted acrylamide, methacrylamide, 2-chloroacrylamide, 2-phenylacrylamide, vinyl ether and ester, epoxy, oxetan, allyl ether and ester epoxy, styrene and styrene derivatives, for example alpha-methylstyrene, p-methylstyrene, p-tert-butyl styrene, p-chlorostyrene, siloxanes, organosilane, diamines, imide monomers, amic acid monomers and their esters, amidimide monomers, maleic acid and maleic acid derivatives, for example, di-n-butyl maleate, dimethyl malenate, diethyl malenate, etc, fumaric acid and fumaric acid derivatives, for example, di-n-butyl fumarate, di-(2-ethylhexyl)fumarate, etc, urethanes or their corresponding homo- and co-polymers. More preferably the polymerizable group D is selected from acrylate, methacrylate, vinyl ether and ester, epoxy, styrene derivatives, siloxanes, diamines, imide monomers, amic acid monomers and their corresponding homo and copolymers.

In the context of the present invention the wording "spacer unit", is preferably S$^1$ and/or S$^2$ each independently from each other represents preferably a single bond or a cyclic, straight-chain or branched, substituted or unsubstituted C$_1$-C$_{24}$alkylen, preferably 1 to 16, more preferably 1 to 12 carbon atoms, and more preferably S$^1$ and/or S$^2$ or further more preferably S$^1$ and S$^2$ together are a C$_6$-C$_{15}$alkylen, such as hexylene, heptylene, octylene, nonylene, decylene, undecylene, dodecylene and preferred are C$_5$- or C$_8$- or C$_{11}$-alkylene; in which one or more, preferably non-adjacent, C-atom, CH— or CH$_2$—, group unreplaced or replaced by a linking group, and/or a non-aromatic, aromatic, unsubstituted or substituted carbocyclic or heterocyclic group of formula (V):

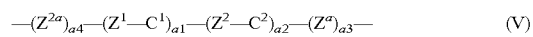
(V)

wherein:
C$^1$, C$^2$ each independently represents a alicyclic or aromatic, optionally substituted carbocyclic or heterocyclic group, preferably connected to each other via the bridging groups Z$^1$ and/or Z$^2$ and/or Z$^{1a}$ and/or Z$^{2a}$ preferably C$^1$ and C$^2$ are connected at the opposite positions via the bridging groups Z$^1$ and Z$^2$ and/or Z$^{1a}$ and/or Z$^{2a}$, so that groups S$^1$ and/or S$^2$ have a long molecular axis, and
Z$^1$, Z$^2$, Z$^{1a}$, Z$^{2a}$ each independently represents a bridging group within the above given meanings and preferences, and
a1, a2, a3, a4 each independently represents an integer from 0 to 3, such that
a1+a2+a3+a4≤6, preferably a3 and a4 are 0 and a1+a2≤4,
preferably S$^1$ and S$^2$ each independently from each other represents a single bond or a spacer unit, which is a straight-chain or branched, substituted, or unsubstituted C$_1$-C$_{24}$alkylen, preferably C$_1$-C$_{12}$alkylen, more preferably C$_1$-C$_6$alkylen, in which one or more, preferably non-adjacent, C-atom, CH— or CH$_2$— group may be replaced by a linking group, preferably replaced by a single bond, —O—, —O(CO), —S—, —(CO)O— or

—NR$^2$—, and wherein the substituent is preferably at least one C$_1$-C$_6$alkyl, preferably methyl; more preferably
S$^1$ is a straight-chain or branched C$_1$-C$_{12}$alkylen, in which one or more, preferably non-adjacent, C-atom, CH— or CH$_2$— group is unreplaced or replaced by —O—, —CH$_2$—, —S— and preferably —O—,
S$^2$ represents a single bond or a spacer unit, which is a straight-chain or branched, substituted or unsubstituted C$_1$-C$_{12}$alkylen, in which one or more, preferably non-adjacent, C-atom, CH— or CH$_2$—, group may be replaced by a linking group, and, preferably replaced by is a single bond, —O—, —O(CO), —S—, —(CO)O— or

—NR$^2$ and wherein the substituent is preferably at least one C$_1$-C$_6$alkyl, preferably methyl; and with the proviso that oxygen atoms of linking groups are not directly linked to each other.

In the context of the present invention the wording "electron withdrawing groups", for W and Z are —COR$^7$, —COOR$^2$, —SOCF$_3$, —NO$_2$, a halogen, such as —F, —Cl, —Br, -J, especially —F; —CF$_3$, —CN, preferably —CN, —COR$^2$ or —COOR$^2$, more preferably —CN or —COOR$^7$, wherein R$^7$ is as described above and within the above given preferences.

In the context of the present invention the wording "electron-donating single substituent" is preferably selected from the groups C$_1$-C$_{24}$alkyl, preferably methyl, ethyl, propyl, isopropyl, butyl, sec.-butyl, tert, -butyl, pentyl, isopentyl, hexyl, iso-hexyl; or —X$^1$—C$_1$-C$_{24}$alkyl, preferably —X$^1$—C$_1$-C$_{12}$alkyl, more preferably —X$^1$—C$_1$-C$_6$alkyl, most preferably —X$^1$—C$_1$-C$_3$alkyl, wherein X$^1$ is a single bond, —O—, —S—, Se, —N—, —NH— and —NR$^7$, preferably —O—, and wherein R$^7$ is as described above and within the above given preferences; preferably —O-methyl, —O-ethyl, —O-propyl, —O-isopropyl, —O-butyl, —O-sec.-butyl, —O-tert-butyl, —O-pentyl, —O-isopentyl, —O-hexyl or —O-isohexyl; or —X$^1$—C$_1$-C$_{24}$alkylen-aryl, preferably —O-benzylen, —O-methylen-phenyl, —O-ethylen-phenyl; or —O—CF$_3$; with the proviso that in the residue C$_1$-C$_{24}$alkyl, one or more C-atom, CH— or CH$_2$— group may be replaced by a linking group. Preferred C$_1$-C$_{24}$alkyl residue is C$_1$-C$_{12}$alkyl, more preferably C$_1$-C$_6$alkyl, and more preferred are methyl, ethyl, propyl, isopropyl, butyl, tert-butyl sec.-butyl, iso-pentyl, pentyl, hexyl or isohexyl and most preferred are methyl and ethyl. Most preferred electron-donating single substituent is methyl, ethyl, propyl, isopropyl, butyl, sec.-butyl, tert.-butyl, —O—CF$_3$, —O-benzylen, —O-methylen-phenyl, —O-methyl, —O-ethyl, —O-propyl, —S-methyl, —S-ethyl, —S-propyl, —NR$^7$-methyl, —NR$^7$-ethyl, —NR$^7$-propyl, wherein R$^7$ is hydrogen or methyl.

In the context of the present invention the term "residue of an electron-donating ring which is condensed to ring A$^1$," is preferably unsubstituted or substituted —X$^1$—C$_1$-C$_{24}$alkylene-(X$^2$)$_{0\ or\ 1}$, or more especially or substituted —X$^1$—C$_2$-C$_{24}$alkylene-(X$^2$)$_{0\ or\ 1}$—, wherein X$^1$ and X$^2$ are independently from each other selected from a single bond, —O—, —S—, Se, —N—, —NH— and —NR$^7$, wherein R$^7$ is as described above and within the above given preferences, wherein the substituted —X$^1$—C$_1$-C$_{24}$alkylene-(X$^2$)$_{0\ or\ 1}$—, is preferably C$_1$-C$_6$alkyl, such as methyl or ethyl, which substitutes a C$_1$-C$_{24}$alkylene position. Preferred X$^1$ and X$^2$ are identical, more preferably X$^1$ and X$^2$ are —O—. Further preferred —X$^1$—C$_1$-C$_{24}$alkylene-(X$^2$)$_{0\ or\ 1}$—, is —X$^1$—C$_1$-C$_{12}$alkylene-(X$^2$)$_{0\ or\ 1}$—, more preferred —X$^1$—C$_1$-C$_6$alkylene-(X$^2$)$_{0\ or\ 1}$—, and most preferred —X$^1$—C$_1$-C$_3$alkylene-(X$^2$)$_{0\ or\ 1}$—, especially 1,3-propylene, 1,2-ethylene, methylene, —CH(CH$_3$)CH(CH$_3$)—, —CH$_2$CH(CH$_3$)CH$_2$—. More preferred X$^1$ and X$^2$ are identical and are —O-propylene-O—, —O-ethylene-O—, -ethylene-O—, —O-methylene-O—, —OCH(CH$_3$)CH(CH$_3$)—O—, —O—CH$_2$CH(CH$_3$)CH$_2$—O—.

In the context of the present invention the substituent "L" is preferably a polar group, preferably the polar group is in the context of the present invention halogen, hydroxy nitro, cyano or carboxy, and/or acryloyloxy, alkoxy, alkylcarbonyloxy, alkyloxocarbonyloxy, methacryloyloxy, vinyl, vinyloxy, allyl, allyloxy, and/or a cyclic, straight-chain or branched alkyl residue, which is unsubstituted, mono- or poly-substituted by fluorine and/or chlorine, and/or a silane group, and/or a siloxane group, wherein the alkyl residue has from 1 to 20 C-atoms, wherein one or more, preferably non-adjacent, —CH$_2$— groups independently may be replaced by a group, preferably selected from —O—, —S—, —NH—, —N(C$_1$-C$_6$)alkyl, —CO—, —COO—, —OCO—, —C=C—, —C≡C—, —Si(CH$_3$)$_2$—, —Si(CH$_3$)$_2$—O—Si(CH$_3$)$_2$—; "L" is more preferably an alkyl residue which has from 1 to 20 C-atoms, wherein one or more, preferably non-adjacent, —CH$_2$— groups independently may be replaced by a group, preferably selected from —O—, such as —O-alkyl, especially —O—(C$_1$-C$_6$)alkyl, —O-methyl, —O-ethyl, —O-propyl, —O-isopropyl, —O-butyl, —O-tert-butyl, —O-sec-butyl, —O-pentyl, —O-isopentyl, —O-hexyl; more especially —O—CH$_3$.

In the context of the present invention the wording "bridging groups", is preferably selected from the groups —O—, —CO—, —CH(OH)—, —CH$_2$(CO)—, —OCH$_2$—, —CH$_2$O—, —O—CH$_2$—O—, —COO—, —OCO—, —OCF$_2$—, —CF$_2$O—, —CON(C$_1$-C$_{16}$alkyl)-, —(C$_1$-C$_{16}$alkyl)NCO—, —CONH—, —NHCO—, —HNOCO—, —OCONH—, —NHCONH—, —OCOO—, —CO—S—, —S—CO—, —CSS—, —SOO—, —OSO—, —SOS—, —SO—, —CH$_2$(SO)—, —SO$_2$—, —CH=CH—, —C≡C—, —CH=CH—COO—, —OCO—CH=CH—, —CH=N—, —C(CH$_3$)=N—, —N=N—, or a single bond; or a cyclic, straight-chain or branched, substituted or unsubstituted C$_1$-C$_{24}$alkylen, wherein one or more C-atom, CH— or CH$_2$— group may independently from each other be replaced by a linking group.

Preferably, the bridging group is —O—, —CO—, —COO—, —OCO—, —OCOO—, —OCF$_2$—, —CF$_2$O—, —CON(CH$_3$)—, —(CH$_3$)NCO—, —CONH—, —NHCO—, —CO—S—, —S—CO—, —CSS—, —SOO—, —OSO—, —CH$_2$(SO$_2$)—, —CH$_2$—CH$_2$—, —OCH$_2$—, —CH$_2$O—, —CH=CH—, —C≡C—, —CH=CH—COO—, —OCO—CH=CH—, or a single bond.

More preferably bridging group is —COO—, —OCO—, —OCOO—, —OCF$_2$—, —CF$_2$O—, —CON(CH$_3$)—, —(CH$_3$)NCO—, —CONH—, —NHCO—, —CO—S—, —S—CO—, —CS—S—, —SOO—, —OSO, especially —COO—, —OCO—, —OCF$_2$—, —CF$_2$O—, —CON(CH$_3$)—, —(CH$_3$)NCO—, —CONH—, —NHCO— or a single bond.

Most preferred bridging group is a single bond, —COO— or —OCO—.

In the context of the present invention the wording "linking group", is preferably be selected from a single bond, —S—, —S(CS)—, —(CS)S—, —CO—S—, —S—CO—, —O—, —CO, —CO—O—, —O—CO—,

—NR$^7$—, —NR$^7$—CO—, —CO—NR$^7$—, —NR$^7$—CO—O—, —O—CO—NR$^7$—, —NR$^7$—CO—NR$^7$—, —CH=CH—, —C≡C—, —O—CO—O—, —Si(CH$_3$)$_2$—O—Si(CH$_3$)$_2$— and unsubstituted or substituted cyclohexylen and unsubstituted or substituted phenylene, preferred is a single bond, —O—, —O(CO), —S—, —(CO)O— or

—N(CH$_3$)—, —NH—; and wherein:

R$^7$ represents a hydrogen atom or C$_1$-C$_6$alkyl and especially hydrogen or methyl; and with the proviso that oxygen atoms of linking groups are not directly linked to each other.

The wording "monocyclic ring" as used in the context of the present invention, preferably denotes optionally substituted carbocyclic and heterocyclic aromatic or alicyclic groups.

The term "aromatic", as used in the context of the present invention, preferably denotes optionally substituted carbocyclic and heterocyclic aromatic groups.

In the context of the present invention the wording "a carbocyclic or heterocyclic ring group" is an alicyclic or/and aromatic group, optionally substituted carbocyclic or heterocyclic group.

The wording "carbocyclic or heterocyclic aromatic group" or "aromatic group" or "aryl" or "carbocyclic and heterocyclic aromatic groups" as used in the context of the present invention represents five, six, ten or 14 ring atoms, which may bear a positive charge, preferably if they comprise a nitrogen; preferred examples of "carbocyclic or heterocyclic aromatic group" or "aromatic group" or "aryl" or "carbocyclic and heterocyclic aromatic groups" are furan, benzene or phenylene, pyridine, pyridinium cation, triazine, triazine cation, 2,3-dihydro-seleno-pheno[3,4-b][1,4]dioxine, pyrimidine, pyrimidine cation biphenylene, naphthalene, anthracene, pyrene, fluorene, 9H-fluorene, 9,9-dimethyl-9H-fluorene, 9H-fluoren-9-one, selenophene, thiophene, phenanthrene, 9,10-dihydrophenanthrene, triphenylene, tetraline which are uninterrupted or interrupted by at least a single heteroatom and/or at least a single bridging group; preferred are benzene, phenylene, naphthalene, biphenylene, phenanthrene, or triphenylen and more preferred are benzene, phenylene and biphenylene, especially phenylene.

The term "phenylene", as used in the context of the present invention, preferably denotes a unsubstituted 1,2-, 1,3- or 1,4-phenylene group or a substituted phenylene group having the substitutents or linkages preferably in the following positions 1,3,5-1,2,5- or 2,3,5. It is preferred that the phenylene group is either a 1,3- or a 1,4-phenylene group. 1,4-phenylene groups are especially preferred.

The term "alicylic", or "alicylic ring", as used in the context of the present invention, preferably denotes optionally substituted "non-aromatic carbocyclic or heterocyclic ring systems".

The wording "carbocyclic or heterocyclic alicyclic group" or "alicyclic group" or "non-aromatic carbocyclic or heterocyclic ring systems" as used in the context of the present invention represents for example ring systems, with 3 to 40 carbon atoms, preferably C17-C40 carbon atoms as for example cyclopropane, cyclobutane, cyclopentane, cyclopentene, cyclohexane, cyclohexene, cyclohexadiene, decaline, tetrahydrofuran, dioxane, pyrrolidine, piperidine or a steroidal skeleton such as cholesterol, which are uninterrupted or interrupted by at least a single heteroatom and/or at least a single bridging group, or rod shaped groups, such as bi-, tri-, or tetra-cyclohexyl, 1,4-phenylene-(1,4-cyclohexylene)$_n$, wherein n is 1, 2, 3 or 4; and preferred are cyclohexane or a steroidal skeleton.

The wording "rod shaped adjacent aromatic and/or aromatic/alicyclic group" as used in the context of the present invention represents for example -(aryl)$_{n1}$-(bridging group)-(alicyclic ring)$_{n2}$, wherein n1 and n2 are independently from each other are 1, 2, 3, 4 or 5, preferably n1 is 1 and n2 is 1, 2 or 3 and wherein preferably aryl is phenyl and alicyclic ring is cyclohexyl, with the proviso that if n1 or n2 are >1 then the aryl groups and licyclic rings may be connected by bridging groups.

The term "alkyl", unless the context requires otherwise, includes straight-chain and branched alkyl, as well as saturated and unsaturated groups, which is substituted or unsubstituted. Preferred is C$_1$-C$_{24}$alkyl, more preferred C$_1$-C$_{12}$alkyl, and most preferred is C$_1$-C$_6$alkyl, such as preferably methyl, ethyl, propyl, isopropyl, butyl, sec.-butyl, tert,-butyl, pentyl, isopentyl, hexyl, iso-hexyl; in which one or more C-atom, CH— or CH$_2$— group may be replaced by a linking group.

The term "alkylene" as used in the context of the present invention is the biradical derivative of alkyl within the above given meaning and preferences.

The term "C$_1$-C$_6$alkylen-aryl" as used in the context of the present invention is -methylen-aryl, ethylene-aryl, preferably is methylene-phenyl.

The term "lower alkyl", as used in the context of the present invention, taken on its own or in a combination such us "lower alkoxy", etc., preferably denotes straight-chain and branched saturated hydrocarbon groups having from 1 to 6, preferably from 1 to 3, carbon atoms. Methyl, ethyl, propyl and isopropyl groups are especially preferred. In case of "lower alkoxy", methoxy, ethoxy, propoxy and isopropoxy groups are especially preferred.

The term "aliphatic", unless the context requires otherwise, includes straight-chain and branched alkyl, as well as saturated and unsaturated groups. Possible substituents include alkyl, aryl (thus giving an araliphatic group) and cycloalkyl, as well as amino, cyano, epoxy, halogen, hydroxy, nitro, oxo etc. Possible heteroatoms which may replace carbon atoms include nitrogen, oxygen and sulphur. In the case of nitrogen further substitution is possible with groups such as alkyl, aryl and cycloalkyl.

The term "halogen" denotes a chloro, fluoro, bromo or iodo substituent, preferably a chloro or fluoro substituent.

The term "heteroatom", as used in the context of the present invention primarily denotes oxygen, sulphur and nitrogen, preferably oxygen and nitrogen, in the latter case preferably in the form of —NH—.

The term "optionally substituted" or "substituted" as used in the context of the present invention primarily means substituted by lower alkyl, lower alkoxy, hydroxy, halogen, two electron-donating single substituent or an electron-donating ring which is condensed to ring or a polymerizable group or by a polar group as defined above.

With respect to straight or branched alkyl, alkylene, alkoxy, alkoxycarbonyl, alkylcarbonyl, alkylcarbonyloxy groups it is repeatedly pointed out that some or several of the —CH$_2$— groups may be replaced e.g. by heteroatoms, but also by other groups. In such cases it is generally preferred that such replacement groups are not directly linked to each other. It is alternatively preferred that heteroatoms, and in particular oxygen atoms are not directly linked to each other.

It is understood that the wording "each ring system includes at least one unsaturation directly connected via electron conjugation (π-π bonding) to the double bond" indicates that each ring system A$^1$ and A$^2$ contains at least one unsaturated bond, i.e. double bond, that is directly linked to the double bond in formula (I) thereby extending the electron conjugation.

In a preferred embodiment ring systems $A^1$ and $A^2$ are a carbocyclic or heterocyclic ring group selected from a monocyclic ring of four to six atoms, or at least two adjacent monocyclic rings of five or six atoms, or a fused bicyclic ring system of eight, nine or ten atoms, or a fused tricyclic ring system of thirteen or fourteen atoms.

More preferably ring systems $A^2$ is selected from pyrimidine, pyridine, pyridine cation, thiophenylene, furanylene, phenanthrylene, 9,10-dihydrophenanthrene, pyrene, naphthylene, 9H-fluorene, 9H-fluoren-9-one, 9,9-dimethyl-9H-fluorene or phenylene, and $A^1$ is selected from cyclohexane, cyclohexene, cyclohexadiene, pyrimidine, pyridine, thiophenylene, furanylene, phenanthrylene, naphthylene, or phenylene, or a steroidal skeleton or a rod shaped adjacent aromatic and/or aromatic/alicyclic group.

In a yet a further embodiment
$A^2$ is a ring system of formula (II):

(II)

and
$A^1$ is a ring system of formula (III):

(III)

wherein:
$C^1$, $C^2$ each independently are a substituted or unsubstituted non-aromatic of 3 to 40 atoms, or an aromatic, optionally substituted, carbocyclic or heterocyclic group of 5 to 14 atoms, preferably connected to each other at the opposite positions via the bridging groups $Z^1$ and $Z^2$, and wherein the substituents of "substituted $C^1$, $C^2$" are $R^4$, $R^5$ for ring $A^2$ and $R^1$, $R^2$, $R^3$ for ring $A^1$, wherein $R^1$, $R^2$, $R^3$, $R^4$ and $R^5$ have the same meanings and dependencies and pü refereces as given above for formula (I) or (a);
and
$Z^1$, $Z^2$ each independently are a single bond or a bridging group preferably selected from —CH(OH)—, —O—, —CH$_2$(CO)—, —SO—, —CH$_2$(SO)—, —SO$_2$—, —CH$_2$(SO$_2$)—, —COO—, —OCO—, —COF$_2$—, —CF$_2$CO—, —S—CO—, —CO—S—, —SOO—, —OSO—, —CH$_2$—CH$_2$—, —O—CH$_2$—, —CH$_2$O—, —CH=CH—, —C—S—, —SH=CH—COO—, —OCO—CH=CH—, —CH=N—, —C(CH$_3$)=N—, —O—CO—O—, —N=N—, or a short alkyl spacer of 1 to 6 carbon atoms, preferably 1 to 3 carbon atoms;
a is 0, 1, 2 or 3, preferably a is 0 or 1, more preferably 0;
with the proviso that $C^2$, which is directly connected to the double bond, is unsaturated and conjugated to it, and preferably
if in formula (II) $C^1$ and/or $C^2$ are unsubstituted or substituted by a substituent L, an electron-donating single substituent, or an electron-donating ring which is condensed to ring $C^1$ and/or $C^2$ and in formula (III) the terminal $C^1$ or $C^2$ is substituted by at least two electron-donating single substituent or an electron-donating ring which is condensed to ring $C^1$ and/or $C^2$, then W is an electron withdrawing group and Z is hydrogen; or
if in formula (II) $C^1$ and/or $C^2$ are substituted by a substituent L an electron-donating single substituent, or an electron-donating ring which is condensed to ring $C^1$ and/or $C^2$, and in formula (III) the terminal $C^1$ or $C^2$ an electron-donating ring which is condensed to ring $C^1$ and/or $C^2$, then W is hydrogen if Z is an electron withdrawing group; or
if in formula (II) $C^1$ and/or $C^2$ are unsubstituted and in formula (III) the terminal $C^1$ or/and $C^2$ is substituted by at least two electron-donating single substituent or an electron-donating ring which is condensed to ring $C^1$ and/or $C^2$, then W is hydrogen if Z is an electron withdrawing group; or
if in formula (II) $C^1$ and/or $C^2$ are substituted by O—C$_2$-C$_6$alkyl, such as —O-ethyl, —O-propyl, —O-butyl, —O-pentyl, —O-hexyl and in formula (III) the terminal $C^1$ or/and $C^2$ is substituted by an electron-donating single substituent, then W is hydrogen if Z is an electron withdrawing group; or
if in formula (II) $C^1$ and/or $C^2$ are substituted by L, an electron-donating single substituent, or hydrogen and in formula (III) the terminal $C^1$ or/and $C^2$ is substituted by —O—C$_2$-C$_6$alkyl, such as —O-ethyl, —O-propyl, —O-isopropyl, —O-butyl, —O-tert-butyl, —O-sec-butyl, —O-pentyl, —O-isopentyl, —O-hexyl; or
if in formula (II) $C^1$ and/or $C^2$ are substituted by O—C$_2$-C$_6$alkyl, such as —O-ethyl, —O-propyl, —O-butyl, —O-pentyl, —O-hexyl and in formula (III) the terminal $C^1$ or/and $C^2$ is substituted by —O—C$_2$-C$_6$alkyl, such as —O-ethyl, —O-propyl, —O-isopropyl, —O-butyl, —O-tert-butyl, —O-sec-butyl, —O-pentyl, —O-isopentyl, —O-hexyl; or
if in formula (II) $C^1$ and/or $C^2$ are substituted by L, an electron-donating single substituent and in formula (III) the terminal $C^1$ or/and $C^2$ is substituted by O—C$_1$-C$_6$alkyl, more preferably —O-methyl, —O-ethyl, and $R^2$ and $R^3$ are independently from each other —O—C$_1$-C$_6$alkyl, such as —O-methyl, —O-ethyl, —O-propyl, —O-isopropyl, —O-butyl, —O-tert-butyl, —O-sec-butyl, —O-pentyl, —O-isopentyl, —O-hexyl;
especially preferred are
if in formula (II) $C^1$ and/or $C^2$ are unsubstituted or substituted by a substituent L, an electron-donating single substituent, or an electron-donating ring which is condensed to ring $C^1$ and/or $C^2$ and in formula (III) the terminal $C^1$ or $C^2$ is substituted by at least two electron-donating single substituent or an electron-donating ring which is condensed to ring $C^1$ and/or $C^2$, then W is an electron withdrawing group and Z is hydrogen; or
if in formula (II) $C^1$ and/or $C^2$ are substituted by a substituent L an electron-donating single substituent, or an electron-donating ring which is condensed to ring $C^1$ and/or $C^2$, and in formula (III) the terminal $C^1$ or $C^2$ an electron-donating ring which is condensed to ring $C^1$ and/or $C^2$, then W is hydrogen if Z is an electron withdrawing group; or
if in formula (II) $C^1$ and/or $C^2$ are unsubstituted and in formula (III) the terminal $C^1$ or/and $C^2$ is substituted by at least two electron-donating single substituent or an electron-donating ring which is condensed to ring $C^1$ and/or $C^2$, then W is hydrogen if Z is an electron withdrawing group.

In a most preferred embodiment the ring A2 is substituted by an electron-donating ring which is condensed to ring.

The term "connected to each other at the opposite positions via the bridging groups $Z^1$ and $Z^2$" means that five- and six-membered rings are preferably linked in 1,3- or 1,4-position and not in neighbouring 1,2-position. Analogous linking pattern in other e.g. higher membered rings will be obvious to a skilled person.

It is understood that ring system $A^1$ has an analogous structure to ring system $A^2$ of formula (II) with the exception that group $A^2$ carries a terminal group. Thus, for a=0 group $C^2$ represents the terminal group and for a>0 groups $C^1$ are connected via the bridging groups $Z^1$, with the final group $C^1$ being the terminal group. Thus, for a=1 ring system $A^2$ has the following formula

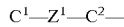

Likewise for a=2 or 3 ring system $A^2$ has the following formula

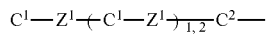

Preferred compounds are compounds according to the general formula (I) wherein
$A^2$ is a ring system of formula (II):

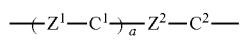 (II)

and
$A^1$ is a ring system of formula (III):

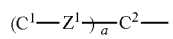 (III)

wherein:
$C^1$, $C^2$ each independently are a substituted or unsubstituted non-aromatic of 3 to 40 atoms, or an aromatic, optionally substituted, carbocyclic or heterocyclic group of 5 to 14 atoms, preferably connected to each other at the opposite positions via the bridging groups $Z^1$ and $Z^2$,
$Z^1$, $Z^2$ each independently are a single bond or a bridging group preferably selected from —CH(OH)—, —O—, —CH$_2$(CO)—, —SO—, —CH$_2$(SO)—, —SO$_2$—, —CH$_2$(SO$_2$)—, —COO—, —OCO—, —COF$_2$—, —CF$_2$CO—, —S—CO—, —CO—S—, —SOO—, —OSO—, —CH$_2$—CH$_2$—, —O—CH$_2$—, —CH$_2$O—, —CH═CH—, —C—S—, —SH═CH—COO—, —OCO—CH═CH—, —CH═N—, —C(CH$_3$)═N—, —O—CO—O—, —N═N—, or a short alkyl spacer of 1 to 6 carbon atoms, preferably 1 to 3 carbon atoms,
a is 0, 1, 2 or 3, preferably a is 0 or 1, more preferably 0,
with the proviso as given above for $C^2$. that $C^2$, which is directly connected to the double bond, is unsaturated and conjugated to it, and
if in formula (II) $C^1$ and/or $C^2$ are unsubstituted or substituted by a substituent L, and in formula (III) the terminal $C^1$ or $C^2$ is substituted by at least two electron-donating single substituent, then W is an electron withdrawing group and Z is hydrogen; or
if in formula (II) $C^1$ and/or $C^2$ are unsubstituted or substituted by a substituent L, and in formula (III) the terminal $C^1$ or $C^2$ is an electron-donating ring which is condensed to ring $C^1$ or $C^2$, then W is hydrogen if Z is an electron withdrawing group or W is an electron withdrawing group if Z is hydrogen; or
if in formula (II) $C^1$ and/or $C^2$ are unsubstituted and in formula (III) the terminal $C^1$ or $C^2$ is substituted by at least two electron-donating single substituent, then W is hydrogen if Z is an electron withdrawing group; preferably these electron-donating single substituents are in meta-position to each other.

Preferably, a is 0 or 1, more preferably 0.
Preferably $C^1$, $C^2$ in formula (II) independently have one of the following meanings:

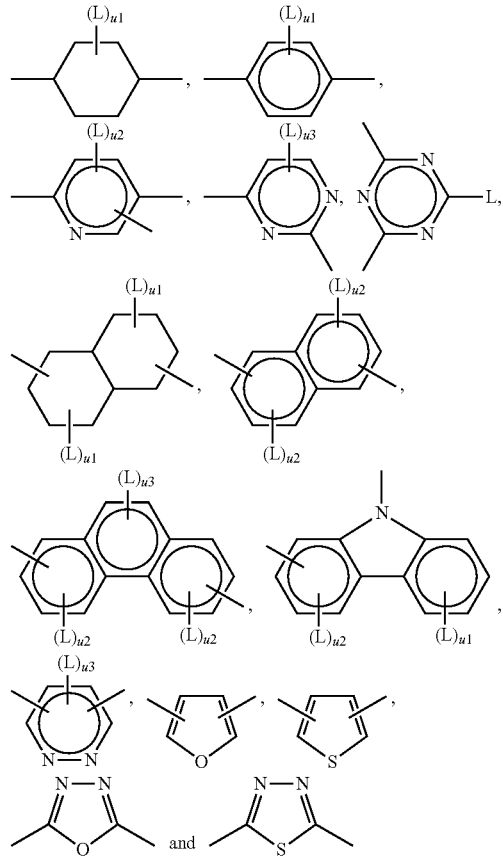

wherein
L has the above giving meaning and preferences
u1 is 0, 1, 2, 3, or 4,
u2 is 0, 1, 2, or 3, and
u3 is 0, 1, or 2.
with the proviso that $C^2$, which is directly connected to the double bond, is unsaturated and conjugated to it.

More preferably $C^1$, $C^2$ are phenanthryl, phenanthrylene, biphenyl, biphenylene, naphthyl, naphthylene, cyclohexyl, cyclohexylen, phenyl or phenylene, pyridine, pyridinylene; preferably naphthyl or naphthylene, phenyl or phenylene, pyridine or pyridinylene.

Preferably $Z^1$, $Z^2$ in formulae (II) and (III) each independently are a single bond or a bridging group most preferably selected from —CH(OH)—, —O—, —CH$_2$(CO)—, —COO—, —OCO—, —COF$_2$—, —CF$_2$CO—, —CH$_2$—CH$_2$—, —O—CH$_2$—, —CH$_2$O—, —CH═CH—, —OCO—CH═CH—, —CH═N—, —C(CH$_3$)═N—, —O—CO—O—, —N═N—, or a short alkyl spacer of 1 to 6 carbon atoms, preferably 1 to 3 carbon atoms.

More preferably $Z_1$, $Z_2$ each independently are a single bond, —O—, —CH$_2$(CO)—, —COO—, —OCO—, —CH$_2$—CH$_2$—, —OCO—CH═CH—, —N═N—, or a short alkyl spacer of 1 to 3 carbon atoms.

Further preferred compound of formula (I) or (Ia) is (Ib)

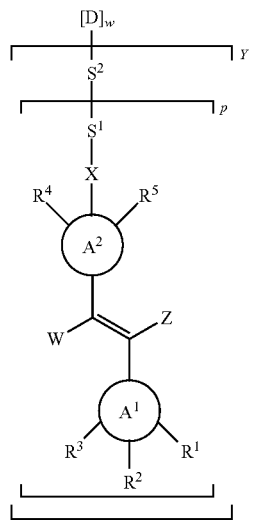

(Ib)

wherein:
A$^1$ and A$^2$ each independently are a ring system of 5 to 40 atoms, wherein each ring system includes at least one unsaturation directly connected via electron conjugation (π-π bonding) to the double bond shown in formula (I);
X represents a single bond or —NH—, —N(CH$_3$)—, —NH—CO—, —CO—NH—, —NH—CO—O—, —O—CO—NH—, —NH—CONH—, —CON(CH$_3$)—, —(CH$_3$)NCO—, —O—, —CO—, —COO—, —OCO—, —OCF$_2$—, —CF$_2$—O—, —CF$_2$S—, —SCF$_2$—, —CF$_2$NH—, —NHCF$_2$—, —S—, —CS—, —SCS—, —SCO—, —CH=CH—, —C≡C— or —O—CO—O—;
preferably X is —O—, —CO—, —COO—, —OCO— or a single bond more preferably —O— or a single bond;
D represents an unsubstituted or substituted aliphatic, aromatic or alicyclic polymerisable group, and represents preferably amine, acrylate, methacrylate, 2-chloroacrylate, 2-phenylacrylate, acrylamide, methacrylamide, 2-chloroacrylamide, 2-phenyl-acrylamide, N—(C$_1$-C$_6$) alkyl substituted acrylamide-, N—(C$_1$-C$_6$)alkyl substituted methacrylamide, N—(C$_1$-C$_6$)alkyl substituted 2-chloroacrylamide, N—(C$_1$-C$_6$)alkyl substituted 2-phenylacrylamide, vinyl ether, vinyl ester, epoxid, malienimide, styrene, vinyl, carboxylic acid, carboxylic halogenid, carbonyl, siloxane, hydroxy, halogenid, or a mixture thereof; more preferred polymerisable group is amine, especially diamines, vinyl, acrylate or methacrylate;
y and p are each independently from each other 1, 2, 3 or 4, preferably 1 or 2;
w is 1, 2, 3, 4 and preferably 1 or 2,
S$^1$ and S$^2$ each independently from each other represents preferably a single bond or a cyclic, straight-chain or branched, substituted or unsubstituted C$_1$-C$_{24}$alkylen, preferably 1 to 16, more preferably 1 to 12 carbon atoms, in which one or more, preferably non-adjacent, C-atom, CH— or CH$_2$—, group unreplaced or replaced by a linking group, and/or a non-aromatic, aromatic, unsubstituted or substituted carbocyclic or heterocyclic group of formula (V):

—(Z$^{2a}$)$_{a4}$—(Z$^1$—C$^1$)$_{a1}$—(Z$^2$—C$^2$)$_{a2}$—(Z$^{1a}$)$_{a3}$— (V)

wherein:
C$^1$, C$^2$ each independently represents a alicyclic or aromatic, optionally substituted carbocyclic or heterocyclic group, preferably connected to each other via the bridging groups Z$^1$ and/or Z$^2$ and/or Z$^{1a}$ and/or Z$^{2a}$, preferably C$^1$ and C$^2$ are connected at the opposite positions via the bridging groups Z$^1$ and Z$^2$ and/or Z$^{1a}$ and/or Z$^{2a}$, so that groups S$^1$ and/or S$^2$ have a long molecular axis, and
Z$^1$, Z$^2$, Z$^{1a}$, Z$^{2a}$ each independently represents a bridging group within the above given meanings and preferences, and
a1, a2, a3, a4 each independently represents an integer from 0 to 3, such that
a1+a2+a3+a4≤6, preferably a3 and a4 are 0 and a1+a2≤4,
preferably S$^1$ and S$^2$ each independently from each other represents a single bond or a spacer unit, which is a straight-chain or branched, substituted, or unsubstituted C$_1$-C$_{24}$alkylen, preferably C$_1$-C$_{12}$alkylen, more preferably C$_1$-C$_6$alkylen, in which one or more, preferably non-adjacent, C-atom, CH— or CH$_2$— group may be replaced by a linking group, preferably replaced by is a single bond, —O—, —O(CO), —S—, —(CO)O— or

—NR$^2$—, and wherein the substituent is preferably at least one C$_1$-C$_6$alkyl, preferably methyl;
more preferably
S$^1$ is a straight-chain or branched C$_1$-C$_{12}$alkylen, in which one or more, preferably non-adjacent, C-atom, CH— or CH$_2$— group is unreplaced or replaced by —O—, —CH$_2$—, —S— and preferably —O—,
S$^2$ represents a single bond or a spacer unit, which is a straight-chain or branched, substituted or unsubstituted C$_1$-C$_{12}$alkylen, in which one or more, preferably non-adjacent, C-atom, CH— or CH$_2$—, group may be replaced by a linking group, and, preferably replaced by is a single bond, —O—, —O(CO), —S—, —(CO)O— or

—NR$^2$—, and wherein the substituent is preferably at least one C$_1$-C$_6$alkyl, preferably methyl;
and wherein
R$^1$, W, Z, R$^4$, R$^5$, R$^2$, R$^3$, R$^4$, R$^5$ are as described above with the above given meanings and preferences; and with the proviso that oxygen atoms of linking groups are not directly linked to each other.

Preferably in compound (Ib) R$^2$ and R$^3$ form together the residue of an electron-donating ring which is condensed to ring A$^1$ and R$^1$ is hydrogen More preferred R$^2$ and R$^3$ form together the residue of an electron-donating ring which is condensed to ring A$^1$ and R$^1$ is hydrogen and R$^4$ and R$^5$ are hydrogen, a substituent L, or an electron-donating single substituent.

Thus more preferred compounds are compounds according to the general formula (I) wherein $A^2$ is a ring system of formula (II):

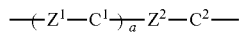
(II)

$A^1$ is a ring system of formula (III):

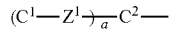
(III)

wherein:

$C^1$, $C^2$ each independently are naphthyl or naphthylene, phenyl or phenylene, pyridine or pyridinylene, which is unsubstituted or substituted $Z^1$, $Z^2$ each independently are a single bond or —O—, —CH$_2$(CO)—, —COO—, —OCO—, —CH$_2$—CH$_2$—, —OCO—CH=CH—, —N=N—, or a short alkyl spacer of 1 to 3 carbon atoms, a is 0 or 1, preferably 0, with the proviso that $C^2$, which is directly connected to the double bond, is unsaturated and conjugated to it, and if in formula (II) $C^1$ and/or $C^2$ are unsubstituted or substituted by a substituent L, and in formula (III) the terminal $C^1$ or $C^2$ is substituted by at least two electron-donating single substituent, then W is an electron withdrawing group and Z is hydrogen; or if in formula (II) $C^1$ and/or $C^2$ are unsubstituted or substituted by a substituent L, and in formula (III) the terminal $C^1$ or $C^2$ is an electron-donating ring which is condensed to ring $C^1$ or $C^2$, then W is hydrogen if Z is an electron withdrawing group or W is an electron withdrawing group if Z is hydrogen; or if in formula (II) $C^1$ and/or $C^2$ are unsubstituted and in formula (III) the terminal $C^1$ or $C^2$ is substituted by two electron-donating single substituent, then W is hydrogen if Z is an electron withdrawing group, preferably these electron-donating single substituents are in meta-position to each other.

Preferred is, if in formula (II) $C^1$ and/or $C^2$ are unsubstituted or substituted by a substituent L, and in formula (III) the terminal $C^1$ or $C^2$ is an electron-donating ring which is condensed to ring $C^1$ or $C^2$, then W is hydrogen if Z is an electron withdrawing group or W is an electron withdrawing group if Z is hydrogen;

y and p are each independently from each other 1, 2, 3 or 4, preferably 1 or 2;

w is 1, 2, 3, 4 and preferably 1 or 2, $S^1$ is a straight-chain or branched $C_1$-$C_6$alkylen, —O—, —CH$_2$—, —S— and preferably —O—, $S^2$ represents a single bond or a spacer unit, which is a straight-chain or branched, substituted or unsubstituted $C_1$-$C_{24}$alkylen, in which one or more, preferably non-adjacent, C-atom, CH— or CH$_2$—, group may be replaced by a linking group, and, preferably replaced by is a single bond, —O—, —O(CO), —S—, —(CO)O— or

—NR$^2$—, and wherein the substituent is preferably at least one $C_1$-$C_6$alkyl, preferably methyl; and with the proviso that oxygen atoms of linking groups are not directly linked to each other;

D is a hydrogen atom, optionally substituted alkyl, or a polymerizable group selected from acrylate, methacrylate, vinyl ether and ester, epoxy, siloxanes, diamine, imide monomers, amic acid monomers or their corresponding homo- and co-polymers.

Preferred examples of the substructure $A^2$ of formula (I), (Ia) or (Ib) are given in the following listing, where "st-" represents the linkage to the double bond of compound (I), (Ia) or (Ib) and "O—" represents the linkage to the $S^1$ group of the molecule:

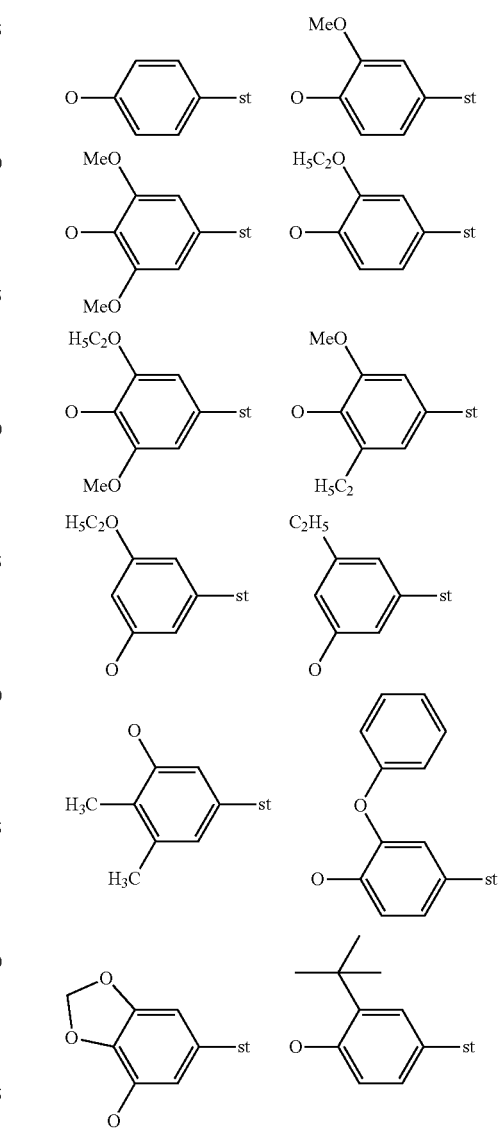

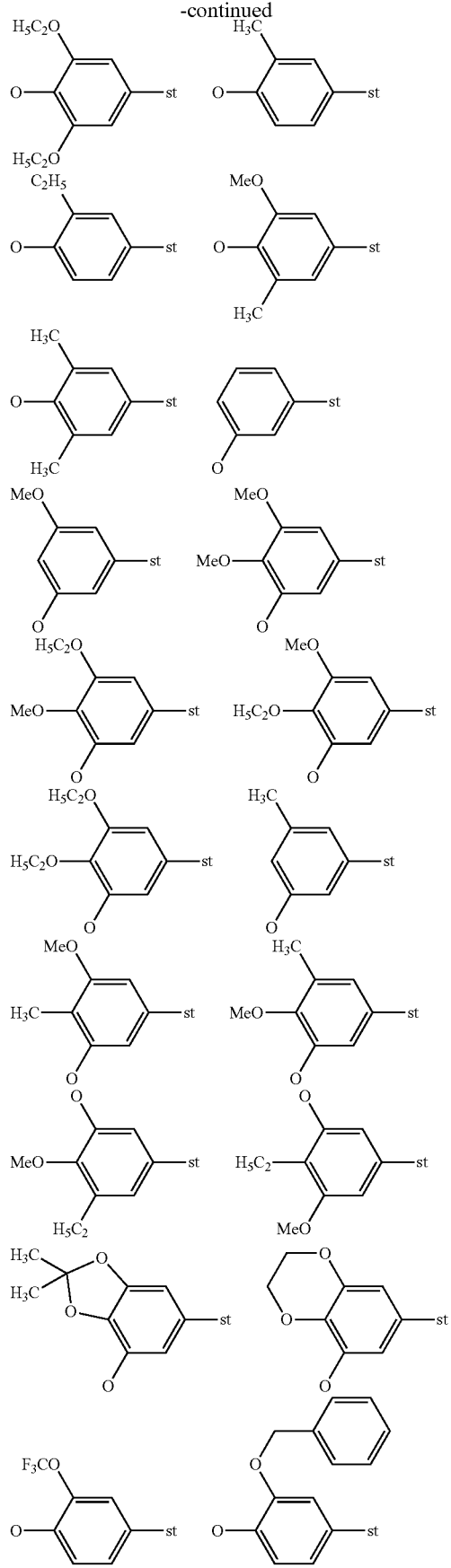
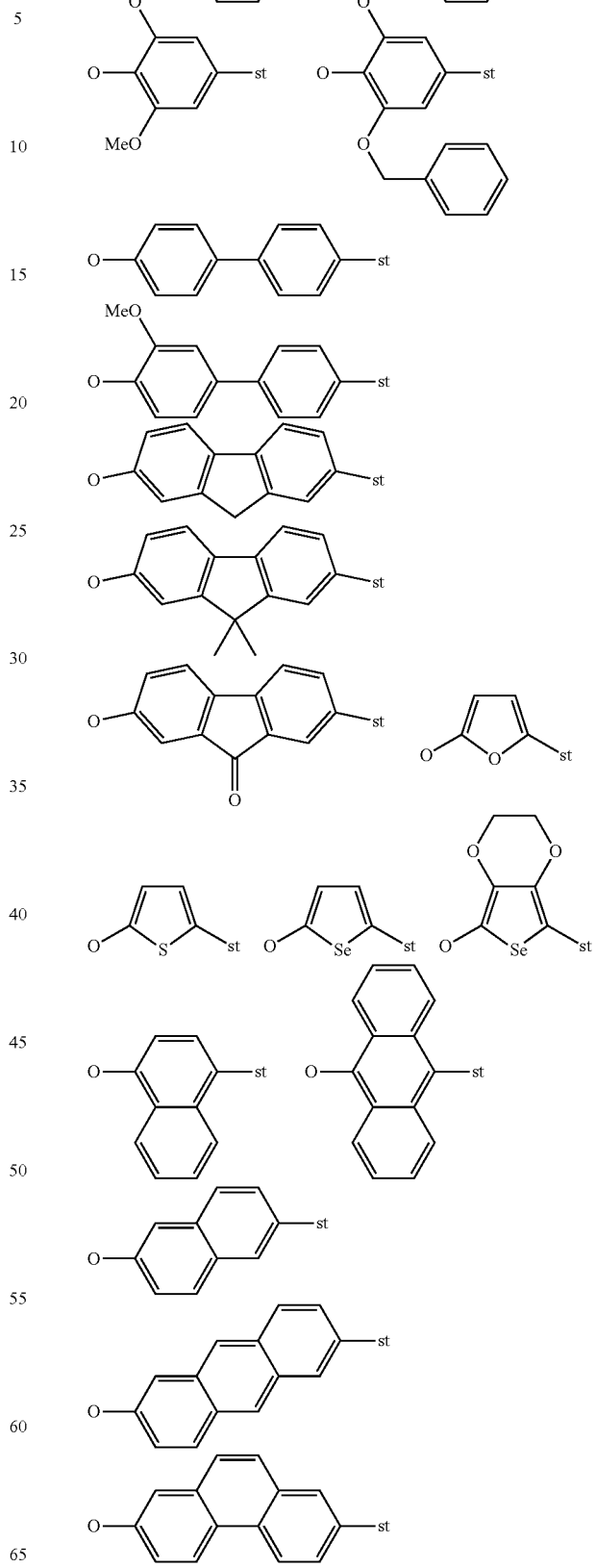

Preferred examples of the substructure $A^1$ of formula (I), (Ia) or (Ib) are given in the following listing, where st- is the bound connected to the stilbene part:
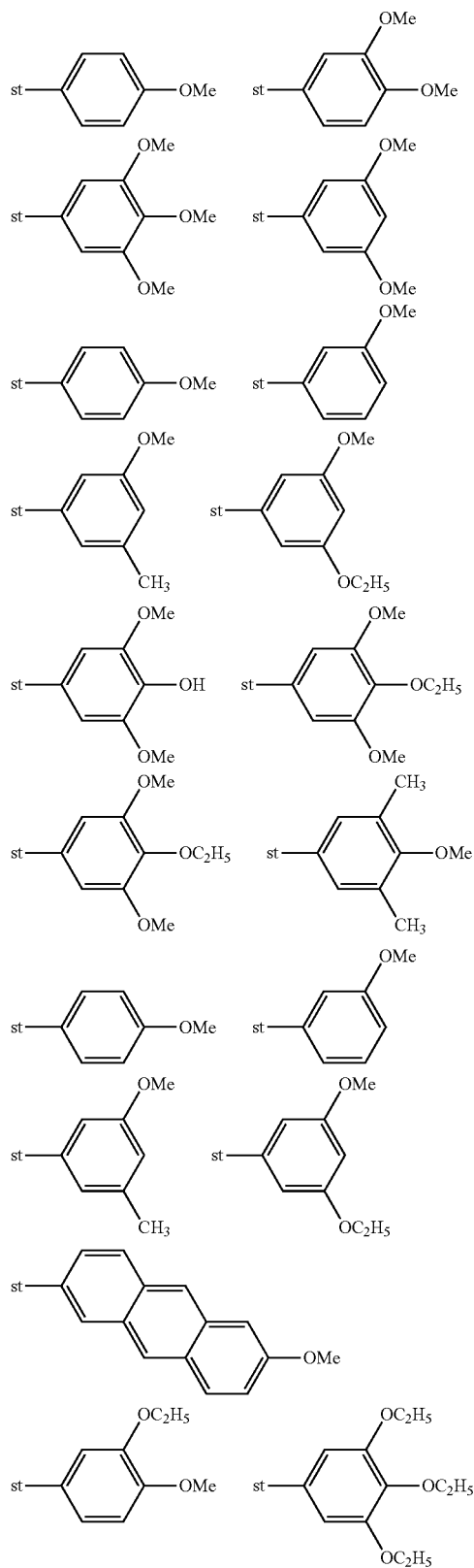
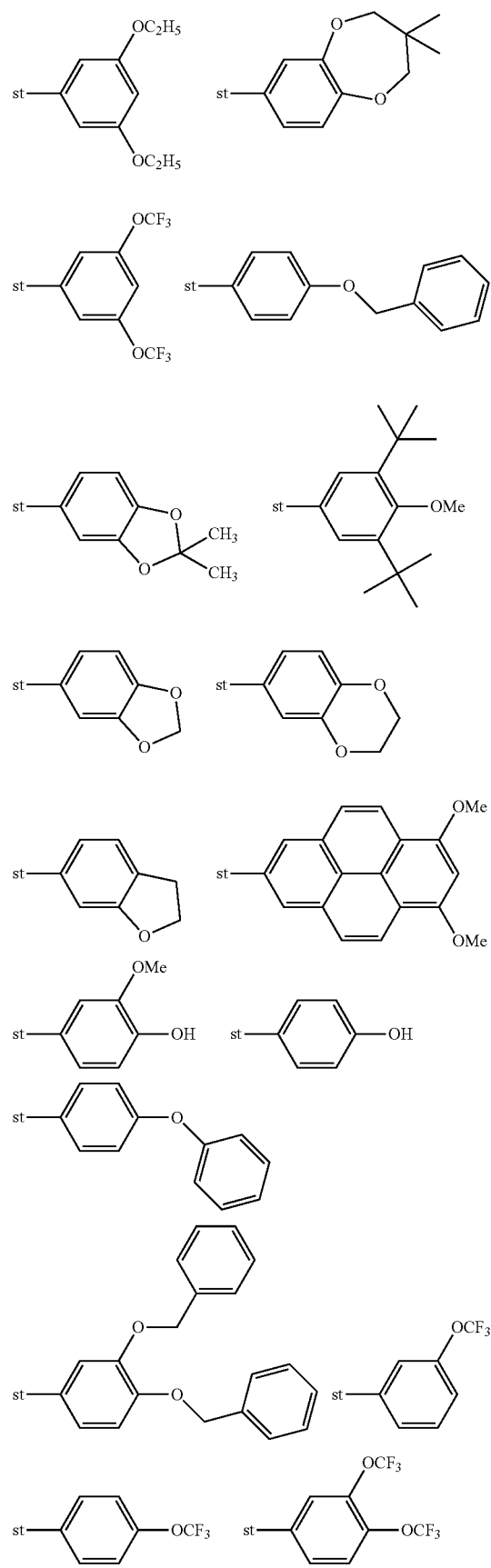

-continued

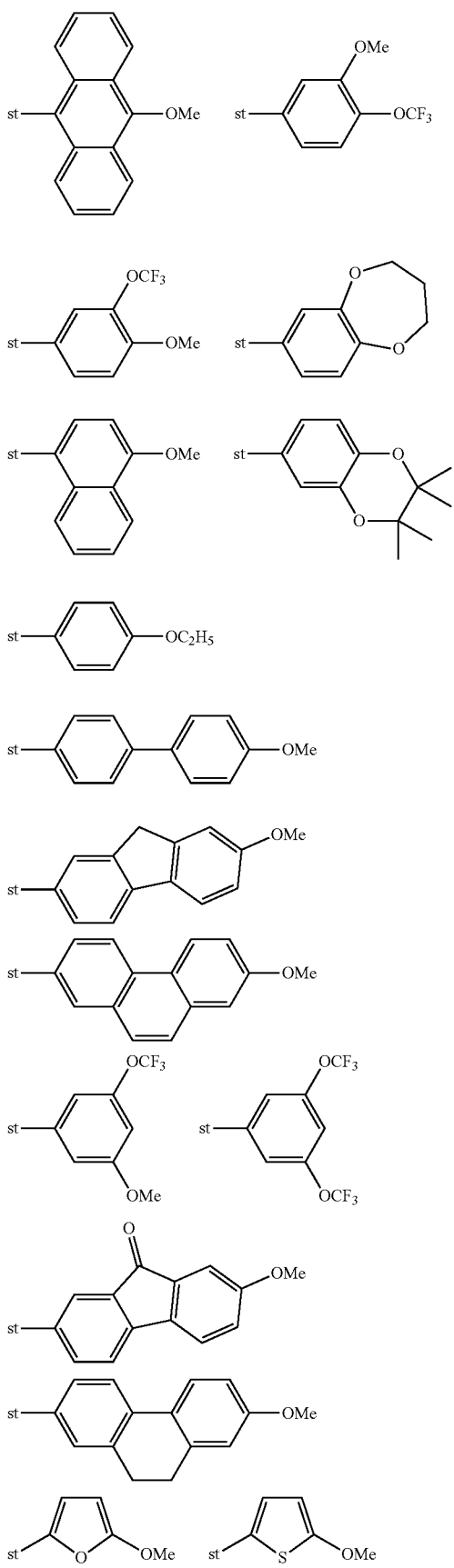

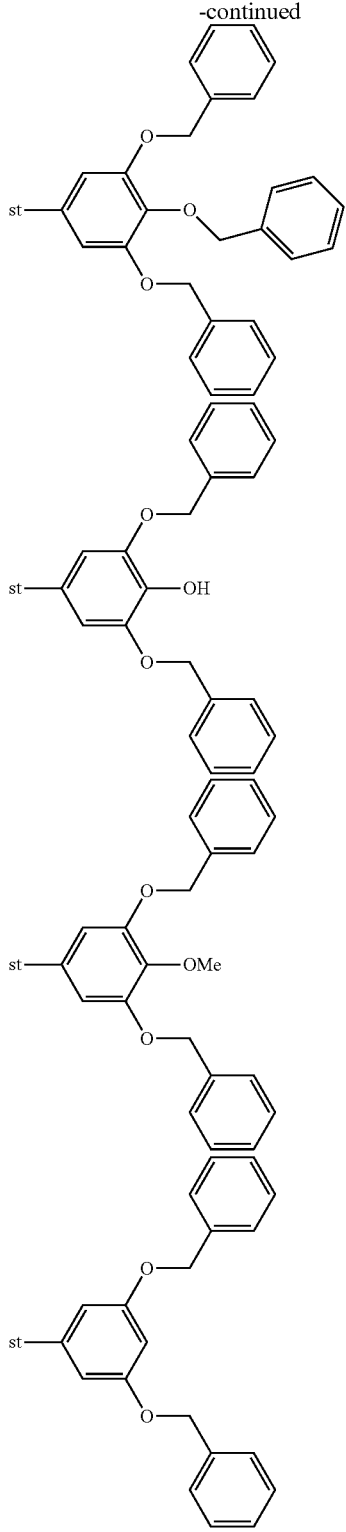

In the context of the present invention the term polymer is not limited to homopolymer, and e.g. has also the meaning of copolymer, homopolymer oligomer, dendrimer, or an oligomeric, homopolymeric, dendrimeric, polymeric, or copolymeric form.

In the context of the present invention the term photoactive has the same meaning as photoreactive, and denotes a chemical group or compound which reacts after irradiating with light, preferably actinic light. Preferably, the term photoreactive denotes to a group or compound, comprising ethene group, which is

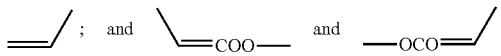

group, a coumarin group, chalcon group, stilben group or azobenzene group. In the context of the present invention the term "not-photoreactive" denotes a group or compound comprising a carbocyclic or heterocyclic aromatic and/or alicyclic or aliphatic group, which is unsubstituted or substituted by an acrylate group, vinyl group, allyl group, epoxy group, maleinimide group, straight-chain or branched $C_1$-$C_{16}$alkyl group, $C_1$-$C_{16}$alkylacrylate group, $C_1$-$C_{16}$alkylvinyl group, $C_1$-$C_{16}$alkylallyl group, $C_1$-$C_{16}$alkylepoxy group, $C_1$-$C_{16}$alkylmaleinimide group, preferably unsubstituted or substituted by $C_1$-$C_{16}$alkylacrylate group, more preferably by $C_1$-$C_6$alkylacrylate group.

More preferably the not-photoreactive group is an unsubstituted or substituted steroidal skeleton such as a cholesterol group, which is uninterrupted or interrupted by at least a single heteroatom and/or at least a single bridging group. Preferably, a cholesterol group is cholesteryl, cholestanyl, cholestan. In the context of the present invention the photoreactive or non-photoreactive group my also reactive by heat treatment, and is preferably also a thermic reactive group.

More preferred is a not-photoreactive group substituted or unsubstituted and selected from a carbocyclic or heterocyclic aromatic group, preferably a substituted or unsubstituted phenylen-(bridging group)-phenylene-, or -(phenylene)$_{n1}$-(bridging group)$_{m1}$-(phenylene)$_{n2}$-(bridging group)$_{m1}$-(cyclohexylen)$_{n3}$-, wherein bridging group has the same meaning and preferences as given below, and n1, n2, n3 represent an integer of 0, 1, 2, 3, 3 or 4 and m1, m2 an integer of 0 or 1, with proviso that at least one n1, n2, n3 or n4 is >1; or the not-photoreactive group is naphthylene or phenylene, which are unsubstituted or substituted by at least one, preferably two, acrylate group, vinyl group, allyl group, epoxy group, maleinimide group, straight-chain or branched $C_1$-$C_{16}$alkyl group, $C_1$-$C_{16}$alkylacrylate group, $C_1$-$C_{16}$alkylvinyl group, $C_1$-$C_{16}$alkylallyl group, $C_1$-$C_{16}$alkylepoxy group, $C_1$-$C_{16}$alkyl-maleinimide group, preferably unsubstituted or substituted by $C_1$-$C_{16}$alkylacrylate group, more preferably by $C_1$-$C_6$alkylacrylate group; or selected from a carbocyclic or heterocyclic alicyclic group, preferably a steroidal skeleton, preferred steroidal skeleton is a cholesterol group, which is uninterrupted or interrupted by at least a single heteroatom and/or at least a single bridging group. More preferred steroid skeleton is a cholesterol group, preferred is cholesteryl, cholestanyl, cholestan.

Especially more preferred is a not-photoreactive group substituted or unsubstituted a carbocyclic or heterocyclic aromatic group, preferably selected from di-(phenyl)alkylen, such as -phenylene-ethylene-phenylene-; -phenylene-propylene-phenylene-, -phenylene-isopropylene-phenylene-, phenylene-butylene-phenylene-, -phenylene-pentylene-phenylene-naphthylene, phenylene, fluorene, benzoic acid, benzyl alcohol, benzoic acid, 2-methoxybenzoic acid, octafluoro-biphenyl, benzidine, fluorenone, 3,5,3',5'-tetrabromo-biphenyl, 2,2'-dichloro-1,1'-biphenyl, 1,11-dimethyl-5,7-dihydro-dibenzo(a,c)cyclohepten-6-one, dibenzo(1,2) dithiine, benzo-phenone, diphenylmethane, 4,4-bis(4-hydroxyphenyl)-valeric acid, 2,2-bis(4-hydroxyphenyl)-hexafluoropropane, 2,2-bis(4-methylphenyl)-hexafluoropropane, 2,2-bis(phenyl)hexa-fluoropropane, bis-(4-chloro-phenyl)-methanone, bis-(4-dimethyl-phenyl)-methanone, benzidine-3,3'-dicarboxylic acid, 1,1'-binaphthyl, diphenyl-3,3'-diglycolic acid, dihydroethidium, 2,2'-dichloro-5,5'-dimethoxybenzidine, 3-methoxybenzidine, 3,3'-dichlorobenzidine (diphenyl-d6), 2,2'-bis(trifluoromethyl)benzidine, 3,3'-bis(trifluoromethyl)-benzidine, 3,3'-dichloro-benzidine-d6, tetramethylbenzidine; or selected from a carbocyclic or heterocyclic alicyclic group, preferably a steroidal skeleton, preferred steroidal skeleton is a cholesterol group, which is uninterrupted or interrupted by at least a single heteroatom and/or at least a single bridging group. More preferred steroid skeleton is a cholesterol group, preferably is cholesteryl, cholestanyl, cholestan.

In a further aspect, the compounds (I) are part of an oligomer, dendrimer, polymer or copolymer or copolymer, which may be a homopolymer or a copolymer. Said oligomer, dendrimer, polymer or copolymer may be obtained by polymerization of the monomer of general formula (I) and may be in form of a gel or a network.

The present invention further relates to an oligomer, dendrimer, polymer or copolymer comprising at least one compound comprising group (I) and preferably a compound (Ia) as monomer unit.

Further, the present invention relates to an oligomer, dendrimer, copolymer or polymer comprising at least one compound (I) within the given meanings and preferences in its polymerized form.

Preferably, the present invention relates to a copolymer comprising a first monomer of compound (I) within the given meanings and preferences, which has preferably the highest absorption in the UV-B- or UV-A-spectrum, more preferably in the UV-A spectrum, and a second comonomer comprising a not-photoreactive group, or a photoreactive group having the highest absorption in the wave length range from 100 to 430 nm, preferably from 150 to 400 nm and more preferably from 200 to 400 nm. In addition, a preferred photoreactive group has the highest absorption in the UV-C, UV-B, or the UV-A spectrum.

In the context of the present invention the wave length range of UV-C is 100 to 280 nm, UV-B is 280 to 315 nm and UV-A is 315 to 380 nm.

Preferably the photoreactive group of the second monomer is selected from a substituted or unsubstituted ethene group, which is

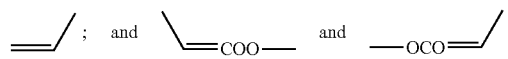

group, coumarin group, chalcon group, stilben group and azobenzene group, more preferably the second monomer comprise a substituted or unsubstituted ethene group, which is

group,

Preferred second comonomer is of the below formula

I

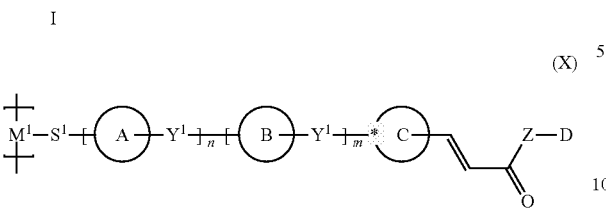

(X)

wherein
M1 is a monomer unit selected from the group consisting of acrylate, methacrylate, 2-chloroacrylate, 2-phenylacrylate, acrylamide, methacrylamide, 2-chloroacrylamide, 2-phenylacrylamide, N-lower alkyl substituted acrylamide, N-lower alkyl substituted methacrylamide, N-lower alkyl substituted 2-chloroacrylamide, N-lower alkyl substituted 2-phenylacrylamide, vinyl ether, vinyl ester, styrene, siloxane, diamine, amide, imide, siloxane, amic ester, amic acid; preferred is methacrylate ring A is unsubstituted phenylene, phenylene which is substituted with fluorine, chlorine, cyano, alkyl or alkoxy, pyridine-2,5-diyl, pyrimidine-2,5-diyl, 1,3-dioxane-2,5-diyl, cyclohexane-1,4-diyl, piperidine-1,4-diyl, or piperazine-1,4-diyl; preferred is phenylene, ring B is unsubstituted phenylene, phenylene which is substituted with fluorine, chlorine, cyano, alkyl or alkoxy, pyridine-2,5-diyl, pyrimidine-2,5-diyl, 1,4-naphthylene, 2,6-naphthylene, 1,3-dioxane-2,5-diyl, or cyclohexane-1,4-diyl; preferred is phenylene, Y1, Y2 each independently is a single covalent bond, —(CH$_2$)t-, —O—, —CO—, —CO—O—, —O—OC—, —NR$^4$—, —CO—NR$_4$—, —R$^4$N—CO—, —(CH$_2$)$_u$—O—, —O—(CH$_2$)$_u$—, —CF$_2$O—, —OCF$_2$—, —(CH$_2$)$_u$—NR$^4$—, or —NR$_4$—(CH$_2$)$_u$—, in which R4 is hydrogen or lower alkyl;
t is a whole number from 1 to 4;
u is a whole number from 1 to 3;
m, n each independently is 0 or 1;

ring C is unsubstituted phenylene, phenylene which is substituted with fluorine, chlorine, cyano, alkyl or alkoxy, pyrimidine-2,5-diyl, pyridine-2,5-diyl, 2,5-thiophenylene, 2,5-furanylene, 1,4-naphthalene, or 2,6-naphthylene;

S$^1$ is a spacer unit which is preferably is C$_1$-C$_{24}$alkylene, and wherein alkylene is unsubstituted or substituted, straight-chain or branched alkylene, in which one or more —CH$_2$— groups may be replaced by at least one linking group, alicyclic or/and aromatic group, Z is —O— or —NR$_5$—, in which R$_5$ is hydrogen or lower alkyl, or a second group of formula D, in which D is hydrogen or an unsubstituted C$_1$-C$_{20}$ straight-chain alkylene group, or a C$_1$-C$_{20}$ straight-chain alkylene group substituted with fluorine or chlorine, a branched-chain C$_1$-C$_{20}$ alkylene group substituted with fluorine or chlorine, an unsubstituted cycloalkyl residue with 3 to 8 ring atoms, or a cycloalkyl residue with 3 to 8 ring atoms substituted with fluorine, chlorine, alkyl or alkoxy.

The term "linking group", as used in the context of the present invention is preferably be selected from —O—, —CO, —CO—O—, —O—CO—,

—NR$^1$—, —NR$^1$—CO—, —CO—NR$^1$—, —NR$^1$—CO—O—, —O—CO—NR$^1$—, —NR$^1$—CO—NR$^1$—, —CH═CH—, —C≡C—, —O—CO—O—, and —Si(CH$_3$)$_2$—O—Si(CH$_3$)$_2$—, and wherein:

R1 represents a hydrogen atom or C$_1$-C$_6$alkyl;
with the proviso that oxygen atoms of linking groups are not directly linked to each other.

Preferably substituent of alkylene in S$^1$ is C$_1$-C$_{24}$-alkyl, preferably C$_1$-C$_{12}$-alkyl, more preferably C$_1$-C$_8$-alkyl; or hydroxy, fluorine, chlorine, cyano, ether, ester, amino, amido. In the context of the present invention the term "alkyl" is substituted or unsubstituted, straight-chain or branched, saturated hydrocarbon residues with a maximum of 20 carbon atoms, wherein one or more —CH$_2$— or —CH$_3$— groups may be unreplaced or replaced by at least one linking group, or/and alicyclic or/and aromatic group.

The term "lower alkyl" taken alone or in combinations such as "lower alkoxy", "hydroxy-lower alkyl", "phenoxy-lower alkyl", "phenyl-lower alkyl", denotes, hereinbefore and hereinafter, straight-chain or branched saturated hydrocarbon residues with 1 to 6, preferably with 1 to 3, carbon atoms, such as methyl, ethyl, propyl, or i-propyl.

Further, preferred second monomer of the present invention consists of compounds of formula I in which ring A signifies phenylene which is unsubstituted or optionally substituted with fluorine, chlorine, cyano, alkyl or alkoxy, pyridine-2,5-diyl, pyrimidine-2,5-diyl, cyclohexane-1,4-diyl;

ring B signifies phenylene which is unsubstituted or optionally substituted with fluorine, chlorine, cyano, alkyl or alkoxy, pyridine-2,5-diyl, pyrimidine-2,5-diyl, 1,4- or 2,6-naphthylene, cyclohexane-1,4-diyl;

Y$^1$, Y$^2$ each independently signify a single covalent bond, —CH2CH2-, —O—, —CF$_2$O—, —OCF$_2$—, —CH$_2$—O—, —O—CH$_2$—, —CO—O— or —O—OC—;

ring C signifies phenylene which is unsubstituted or optionally substituted with fluorine, chlorine, cyano, alkyl or alkoxy, or pyrimidine-2,5-diyl, pyridine-2,5-diyl, 2,5-furanylene, 1,4- or 2,6-naphthylene;

Z signifies —O— and

D signifies hydrogen or a straight-chain or branched alkylene group with 1 to 20, especially with 1 to 12, carbon atoms or a cycloalkyl residue with 5 or 6 ring atoms which is optionally substituted with alkyl or alkoxy, especially with methyl or methoxy, and M$^1$ and S$^1$ m and n have the significance given above.

In addition, further preferred is the second monomer selected from polymers, respectively their monomers according to formula (I) according to the patents and patent applications given below and herewith incorporated by reference: U.S. Pat. No. 5,539,079, U.S. Pat. No. 6,201,087, U.S. Pat. No. 6,107,427, U.S. Pat. No. 6,632,909, U.S. Pat. No. 6,340,506, U.S. Pat. No. 6,649,230, U.S. Pat. No. 6,833,421, U.S. Pat. No. 6,831,148, U.S. Pat. No. 7,514,514, U.S. Pat. No. 7,750,185, U.S. Pat. No. 7,687,118, U.S. Pat. No. 7,959,990, US2008-0293888 A1, WO2008/135131.

In a preferred embodiment the present invention relates to copolymers wherein the weight ratio of the first monomer to the second comonomer, preferably the comonomer X, is 99.9:0.1 to 0.1:99.9.

In dependence from the envisaged use, desired properties and method, the ratio of the comonomers of the copolymers of the invention may vary.

In a further preferred embodiment the copolymers have a weight ratio of the first monomer to the second comonomer, preferably the comonomer X, is 99.5:0.5 to 1:1, more preferably from 99:1 to 80:20, and particularly preferred from 99:1 to 90:10. In addition, preferred are copolymers have a weight ratio of the first monomer to the second comonomer, preferably the comonomer X, is 90:10 to 30:70, more preferably from 90:10 to 50:50, and particularly preferred from 90:10 to 60:40.

The invention relates in a further aspect to alignment layer materials comprising said compounds (I) in monomeric, oligomeric, dendrimeric, polymeric, or copolymeric form. Such alignment layer materials are particularly useful for the alignment of liquid crystals and polymerizable or crosslinkable liquid crystalline materials.

The invention relates in yet a further aspect to optical elements, e.g. optical films having a nematic, smectic or cholesteric order, and electro-optical elements, e.g. liquid crystal display cells, comprising an alignment layer made of a material comprising functionalized photoreactive compounds according to the general formula (I) in monomeric, oligomeric, dendrimeric, polymeric or copolymeric form.

In specific embodiments, the alignment layer has a pattern of different alignment directions, which pattern advantageously can be formed by photoalignment methods.

In a further aspect the invention also relates to the use of one or more oligomers, dendrimers, copolymer or polymers according to the present invention or a composition according to the invention as an alignment layer for liquid crystals, preferably polymerizable liquid crystals or switchable liquid crystals.

The compounds according to the present invention in form of prefinished monomers may be readily prepared using methods that are well known to the person skilled in the art. Suitable methods can for instance be found in Houben-Weyl, Methoden der Organischen Chemie, Thieme-Verlag, Stuttgart.

Subsequently these prefinished monomers are typically subjected to direct polymerisation to obtain an oligomer, dendrimer, polymer or copolymer. Thus, the compounds of the present invention may also be part of an oligomer, a dendrimer, polymer, copolymer, which may be a homopolymer or a copolymer.

In a specific embodiment the compounds with group of formula (I), or the oligomer, dendrimer, polymer or copolymer comprising group (I) may be formulated with any other monomers, functional moieties and additives, such as silane-containing compounds, epoxy-containing crosslinking agents, a photosensitiser, a photoradical generator and/or a cationic photoinitiator.

Further, the oligomer, dendrimer, polymer or copolymer comprising group (I) comprise in a further embodiment of the invention other polymers, copolymers oligomers, monomers, photoactive polymers, photoactive copolymers, photoactive oligomers and/or photoactive monomers.

The present invention also relates to a composition comprising an oligomer, dendrimer, polymer or copolymer comprising group (I) and optionally other monomers, functional moieties and additives, such as silane-containing compounds, epoxy-containing crosslinking agents, a photosensitiser, a photoradical generator and/or a cationic photoinitiator, such as cross-linking agents, such as epoxy-, acrylate-, methacrylate-agents such as for example the photoalignment additives as disclosed in US 2009/0290109; or additives selected from the following group: 4,4'-methylene-bis-(N,N-diglycidylaniline), trimethylolpropane triglycidyl ether, benzene-1,2,4,5-tetracarboxylic acid 1,2,4,5-N,N'-diglycidyldiimide, polyethylene glycol diglycidyl ether and N,N-diglycidylcyclohexylamine, Trimethylolpropane tris(3-mercaptopropionate), Pentaerythritol tetrakis(3-mercaptopropionate), Trimethylolpropane tris(2-mercaptoacetate), Pentaerythritol tetrakis(2-mercaptoacetate); or additives such as silane-containing compounds and epoxy-containing crosslinking agents for further improving the adhesion of the polymer to a substrate. Example for silane adhesion promoters were described in the literature, for example Plast. Eng. 36 (1996) (Polyimides, fundamentals and applications). The above epoxy-containing crosslinking agent preferably includes 4,4'-methylenebis(N,N-diglycidylaniline), trimethylolpropane triglycidyl ether, benzene-1,2,4,5-tetracarboxylic acid 1,2:4,5-N,N'-diglycidyldiimide, polyethylene glycol diglycidyl ether, N,N-diglycidyl-cyclohexylamine and the like.

In addition, the compositions of the present invention may comprise additives such as Thioxanthone, 4,4'-Bis(dimethylamino)benzophenone, Thiomichler's Ketone; or other polymers, oligomers, monomers, photoactive polymers, photoactive oligomers and/or photoactive monomers.

The compositions of the invention comprising the polymers, copolymers according to the invention may contain additives such a photosensitiser, a photoradical generator and/or a cationic photoinitiator. Example for such additives were 2,2-dimethoxy-phenylethanone, mixture of diphenylmethanone and N,N-dimethylbenzenamine or ethyl 4-(dimethylamino)benzoate, xanthone, thioxanthone, Irgacure™ 184, 369, 500, 651 and 907 (Ciba), Michler's ketone, triaryl sulfonium salt and the like.

A preferred composition of the present invention comprises a copolymer and in addition comprises epoxy-, acrylate-, allyl-, methacrylate-, vinyl-compounds.

The compositions, preferably blends comprising a copolymer comprising, according to the invention may optionally further include organic solvent. Organic solvent includes, however, is not limited to chlorobenzene, pyrrolidone solvents such as preferably, N-methyl-2-pyrrolidone, N-ethyl-2-pyrrolidone, N-cyclohexyl-2-pyrrolidone; dimethylsulfoxide, dimethylformamide, toluene, chloroform, organic ester, such as acetyl acetic ester, butyl acetate, ethyl acetate or butyl acetic ester, pentyl acetic ester, hexyl acetic ester; further Y-butyrolactone, methyl cellosolve, butyl cellosolve, butyl carbitol, tetrahydrofuran, diethylene glycol diethylether, dipentylether dipropylene glycol dimethylether, diisobutyl ketone momoethylene glycol dimethyl ether, etc. These solvents can be used alone or in mixtures thereof.

Preferably, the composition of the invention comprises 0.5% to 99% by weight of a compound (I), (Ia), or (Ib) or a polymer, which is preferably a polymer, homo- or copolymer or oligomer, of compound (I), (Ia), or (Ib) as described above, and 99.5 to 1% by weight of an organic solvent. Preferably, the composition, preferably blend, comprises 0.5 to 40% by weight and more preferably 0.5 to 10% by weight and most preferably 0.5 to 5% by of a polymer, homo- or copolymer or oligomer of compound (I), (Ia), or (Ib), or of compound (I), (Ia), or (Ib).

For the direct polymerisation, the monomers and (optionally) the comonomers are firstly prepared separately from the individual components. Subsequently the formation of the polymers is effected in a manner known per se for any given polymer, copolymer for example under the influence of UV radiation or heat or by the action of radical or ionic catalysts.

Potassium peroxodisulfate, dibenzoyl peroxide, azobisisobutyronitrile or di-tert-butyl peroxide are examples of radical initiators. Ionic catalysts are alkali-organic compounds such as phenyllithium or naphthylsodium or Lewis acids such as $BF_3$, $AlCl_3$, $SnCl_3$ or $TiCl_4$. The monomers can be polymerised in solution, suspension, emulsion or substance.

If copolymerized with other comonomers the obtained copolymers are consisting of a monomer unit derivating from formula (I) as defined in any of the proceeding meanings and any other known second comonomer unit that is commercially available or not or with the meaning and preferences as given above.

Upon polymerization it may further be advantageous to terminate the growing polymer chain after a suitable chain length is reached by capping the polymerizable group present at the chain end by using specific reagents well known in the art.

Suitable polymers include polyacrylates, polymethacrylates, polyacrylamides, polymethacrylamides, polyvinylether and polyvinylester, polyallylether and ester, polystyrenes, polysiloxanes, polyimides, polyamic acids and their esters, polyamidimides, polymaleic acids, polyfumaric acids polyurethanes and derivatives thereof.

These polymers may all be prepared according to well known methods in the art. Thus for example the poly(meth) acrylates described herein may be prepared in line with methods such as described in Polymer Synthesis Characterization: A Laboratory Manual (Stanley R. Sandler, Wolf Karo, JoAnne Bonesteel, Eli M. Pearce) and Principles of Polymerization (George Odian).

Thus in the case when the monomer unit is bearing an acrylic or methacrylic end, the comonomer unit can be represented by compounds listed below. Most of them are commercially available from chemical suppliers such as Aldrich, ABCR, ACROS, Fluka,
or could be monomers selected for example as herewith incorporated by references from U.S. Pat. No. 7,959,990, from column 61, line 14 to column 69, line 8, and U.S. Pat. No. RE36,625, U.S. Pat. No. 6,201,087, U.S. Pat. No. 6,107,427, U.S. Pat. No. 6,632,909, U.S. Pat. No. 6,649,230, U.S. Pat. No. 6,833,421, U.S. Pat. No. 7,514,514 U.S. Pat. No. 7,491,752 and WO-2004/060861.

The polyamic acids, polyamic acid esters and polyimides according to the present invention may be prepared in line with known methods, such as those described in Plast. Eng. 36 (1996), (Polyimides, fundamentals and applications), Marcel Dekker Inc. For example, the polycondensation reaction for the preparation of the polyamic acids is carried out in solution in a polar aprotic organic solvent, such as γ-butyrolactone, N,N-dimethylacetamide, N-methylpyrrolidone or N,N-dimethylformamide. In most cases equimolar amounts of the dianhydride and the diamine are used, that is to say one amino group per anhydride group. If it is desired to stabilise the molecular weight of the polymer, it is possible for that purpose to add an excess or a less-than-stoichiometric amount of one of the two components or to add a monofunctional compound in the form of a dicarboxylic acid monoanhydride or in the form of a monoamine. Examples of such monofunctional compounds are maleic anhydride, phthalic anhydride, aniline and so on. The reaction is carried out preferably at a temperature of less than 100° C.

The cyclisation of the polyamic acids to form the polyimides can be carried out by heating that is to say by condensation with removal of water or by other imidisation reactions with reagents. When carried out purely thermally, the imidisation of the polyamic acids is not always complete, that is to say the resulting polyimides may still contain proportions of polyamic acid. The imidisation reactions are generally carried out at a temperature of from 60 to 250° C., but preferably at less than 200° C. In order to achieve imidisation at rather lower temperatures there are additionally mixed into the reaction mixture reagents that facilitate the removal of water. Such reagents are, for example, mixtures consisting of acid anhydrides, such as acetic acid anhydride, propionic acid anhydride, phthalic acid anhydride, trifluoroacetic acid anhydride, and tertiary amines, such as triethylamine, trimethylamine, tributylamine, pyridine, N,N-dimethylaniline, lutidine, collidine etc. The amount of reagents used in that case is preferably at least two equivalents of amine and four equivalents of acid anhydride per equivalent of polyamic acid to be condensed.

The imidisation reaction can be carried out before or alternatively only after application to a support. The latter variant is preferred especially when the polyimide in question has poor solubility in the customary solvents.

Thus the polymer material or oligomer material from the class of polyamic acids, polyamic acid esters or polyimides (and any mixtures thereof) may be obtained by or obtainable by the reaction of at least one compound represented by the general formula (I) wherein D represents a diamine group and optionally one or more additional other diamines (as e.g. given above), with one or more tetracarboxylic acid anhydrides of the general formula (IV)

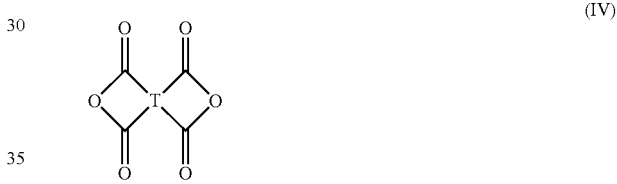

(IV)

wherein:
T represents a tetravalent organic radical.

The tetravalent organic radical T is preferably derived from an aliphatic, alicyclic or aromatic tetracarboxylic acid dianhydride.

Preferred examples of aliphatic or alicyclic tetracarboxylic acid dianhydrides are: 1,1,4,4-butanetetracarboxylic acid dianhydride, ethylenemaleic acid dianhydride, 1,2,3,4-cyclobutanetetracarboxylic acid dianhydride, 1,2,3,4-cyclopentanetetracarboxylic acid dianhydride; 2,3,5-tricarboxycyclopentylacetic acid dianhydride (with the term "2,3,5-tricarboxycyclopentylacetic acid dianhydride" all isomers of this compound are incorporated especially the exo and/or endo body), 2,3,5-tricarboxycyclopentylacetic-1,2:3,4-dianhydride is accessible for example by processes as described in JP59-190945, JP60-13740 and JP58-109479, respectively DE 1078120 and JP58-109479, or GB 872,355, and JP04458299, which processes are herewith incorporated by reference;
tetrahydro-4,8-methanofuro[3,4-d]oxepine-1,3,5,7-tetrone,
  3-(carboxymethyl)-1,2,4-cyclopentanetricarboxylic acid
  1,4:2,3-dianhydride, hexahydrofuro[3',4':4,5]cyclopenta
  [1,2-c]pyran-1,3,4,6-tetrone, 3,5,6-tricarboxy-norbornylacetic acid dianhydride, 2,3,4,5-tetrahydrofurantetracarboxylic acid dianhydride, rel-[1S,5R,6R]-3-oxabicyclo
  [3.2.1]octane-2,4-dione-6-spiro-3'-(tetrahydrofuran2',5'-
  dione), 4-(2,5-dioxotetrahydrofuran-3-yl)
  tetrahydronaphthalene-1,2-dicarboxy-licacid
  dianhydride, 5-(2,5-dioxotetrahydro-furan-3-yl)-3-methyl-3-cyclohexene-1,2-dicarboxylic-acid dianhydride, bicyclo[2.2.2]oct-7-ene-2,3,5,6-tetra-carboxylic acid dianhydride, bicyclo[2.2.2]octane-2,3,5,6-tetracarboxylic acid dianhydride, 1,8-dimethylbicyclo[2.2.2]oct-7-ene-2,3,5,6-tetracarboxylic acid dianhydride, pyromellitic acid dianhydride, 3,3',4,4'-benzophenonetetracarboxylic acid dianhydride, 4,4'-oxydiphthalic acid dianhydride, 3,3',4,4'-diphenylsulfonetetracarboxylic acid dianhydride, 1,4,5,8-naphthalenetetracarboxylic acid dianhydride, 2,3,6,7-naphthalenetetracarboxylic acid dianhydride, 3,3',4,4'-dimethyldiphenylsilanetetracarboxylic acid dianhydride, 3,3',4,4'-tetraphenylsilanetetracarboxylic acid dianhydride, 1,2,3,4-furantetracarboxylic acid di-anhydride, 4,4'-bis(3,4-dicarboxyphenoxy)diphenyl sulfide dianhydride, 4,4'-bis(3,4-dicarboxyphenoxy)-diphenyl sulfone dianhydride, 4,4'-bis(3,4-dicarboxyphenoxy)diphenylpropane dianhydride, 3,3',4,4'-biphenyltetracarboxylic acid dianhydride, ethylene glycol bis(trimellitic acid) dianhydride, 4,4'-(1,4-phenylene)bis(phthalic acid) dianhydride, 4,4'-(1,3-phenylene)bis(phthalic acid) dianhydride, 4,4'-(hexafluoroisopropylidene)diphthalic acid dianhydride, 4-tert-butyl-6-(2,5-dioxotetrahydro-3-furanyl)-2-benzofuran-1,3-dione, 5-(2,5-dioxotetrahydro-3-furanyl)-3a,4,5,9b-tetrahydronaphtho[1,2-c]furan-1,3-dione, 5-(2,5-dioxotetrahydro-3-furanyl)-5-methyl-3a,4,5,9b-tetrahydronaphtho[1,2-c]furan-1,3-dione, 5-(2,5-dioxotetrahydro-3-furanyl)-6-methylhexahydro-2-benzofuran-1,3-dione, 5-(2,5-dioxotetrahydro-3-furanyl)-7-methyl-3a,4,5,7a-tetrahydro-2-benzofuran-1,3-dione, 6-(2,5-dioxotetrahydro-3-furanyl)-4-methylhexahydro-2-benzofuran-1,3-dione, 9-isopropyloctahydro-4,8-ethenofuro[3',4':3,4]cyclobuta[1,2-t][2]benzofuran-1,3,5,7-tetrone, 1,2,5,6-cyclooctanetetracarboxylic acid dianhydride, octahydro-4,8-ethenofuro[3',4':3,4]cyclobuta[1,2-f][2]benzofuran-1,3,5,7-tetrone, octahydrofuro[3',4':3,4]cyclobuta[1,2-f][2]benzofuran-1,3,5,7-tetrone, tetrahydro-3,3'-bifuran-2,2',5,5'-tetrone, 4,4'-oxydi(1,4-phenylene)bis(phthalic acid) dianhydride, and 4,4'-methylenedi(1,4-phenylene)bis(phthalic acid) dianhydride.

Preferred examples of aromatic tetracarboxylic acid dianhydrides are:
pyromellitic acid dianhydride,
3,3',4,4'-benzophenonetetracarboxylic acid dianhydride,
4,4'-oxydiphthalic acid dianhydride,
3,3',4,4'-diphenylsulfonetetracarboxylic acid dianhydride,
1,4,5,8-naphthalenetetracarboxylic acid dianhydride,
2,3,6,7-naphthalenetetracarboxylic acid dianhydride,
3,3',4,4'-dimethyldiphenylsilanetetracarboxylic acid dianhydride,
3,3',4,4'-tetraphenylsilanetetracarboxylic acid dianhydride,
1,2,3,4-furantetracarboxylic acid dianhydride,
4,4'-bis(3,4-dicarboxyphenoxy)diphenyl sulfide dianhydride,
4,4'-bis(3,4-dicarboxyphenoxy)diphenyl sulfone dianhydride,
4,4'-bis(3,4-dicarboxyphenoxy)diphenylpropane dianhydride,
3,3',4,4'-biphenyltetracarboxylic acid dianhydride,
ethylene glycol bis(trimellitic acid) dianhydride,
4,4'-(1,4-phenylene)bis(phthalic acid) dianhydride,
4,4'-(1,3-phenylene)bis(phthalic acid) dianhydride,
4,4'-(hexafluoroisopropylidene)diphthalic acid dianhydride,
4,4'-oxydi(1,4-phenylene)bis(phthalic acid) dianhydride,
4,4'-methylenedi(1,4-phenylene)bis(phthalic acid) dianhydride,
4-tert-butyl-6-(2,5-dioxotetrahydro-3-furanyl)-2-benzofuran-1,3-dione,
and the like.

More preferably the tetracarboxylic acid dianhydrides used to form the tetravalent organic radical T are selected from:
1,2,3,4-cyclobutanetetracarboxylic acid dianhydride,
1,2,3,4-cyclopentanetetracarboxylic acid dianhydride,
2,3,5-tricarboxycyclopentylacetic acid dianhydride,
tetrahydro-4,8-methanofuro[3,4-d]oxepine-1,3,5,7-tetrone,
3-(carboxymethyl)-1,2,4-cyclopentanetricarboxylic acid 1,4:2,3-dianhydride,
hexahydrofuro[3',4':4,5]cyclopenta[1,2-c]pyran-1,3,4,6-tetrone,
5-(2,5-dioxotetrahydrofuran-3-yl)-3-methyl-3-cyclohexene-1,2-dicarboxylic acid dianhydride,
pyromellitic acid dianhydride,
4-(2,5-dioxotetrahydrofuran-3-yl)tetrahydronaphthalene-1,2-dicarboxylic acid dianhydride,
5-(2,5-dioxotetrahydro-3-furanyl)-5-methyl-3a,4,5,9b-tetrahydronaphtho[1,2-c]furan-1,3-dione,
5-(2,5-dioxotetrahydro-3-furanyl)-3a,4,5,9b-tetrahydronaphtho[1,2-c]furan-1,3-dione,
5-(2,5-dioxotetrahydro-3-furanyl)-7-methyl-3a,4,5,7a-tetrahydro-2-benzofuran-1,3-dione,
4-tert-butyl-6-(2,5-dioxotetrahydro-3-furanyl)-2-benzofuran-1,3-dione,
4,4'-(hexafluorneoisopropylidene)diphthalic acid dianhydride and
bicyclo[2.2.2]oct-7-ene-2,3,5,6-tetracarboxylic acid dianhydride.

Further, preferred examples of aliphatic or alicyclic tetracarboxylic acid dianhydrides are those as disclosed in EP 6887534 from column 6, line 31 to column 9, line 34, or in WO2009/051207 on page 8, line 1 to 2 and which are herewith incorporated by reference.

The term "diamine" or "diamine compound" is to be understood as designating a chemical structure which has at least two amino groups, i.e. which may also have 3 or more amino groups.

The diamine D of the present invention is especially more preferably selected from radicals of the following structure, $D^1$, which is represented by substituted or unsubstituted o-phenylenediamine, p-phenylene-diamine, m-phenylenediamine, biphenyldiamine, aminophenylen-Z4-phenylenamino, wherein Z4 has the same meaning and preferences as given above, especially 4-(4-aminobenzyl)phenylamine, 4-[2-(4-aminophenyl)ethyl]phenyl-amine; naphthylenediamine, benzidine, diaminofluorene, 3,4-diaminobenzoic acid, 3,4-diaminobenzyl alcohol dihydrochloride, 2,4-diaminobenzoic acid, L-(+)-threo-2-amino-1-(4-aminophenyl)-1,3-propanediol, p-aminobenzoic acid, [3,5-3h]-4-amino-2-methoxybenzoic acid, L-(+)-threo-2-(N,N-dimethylamino)-1-(4-aminophenyl)-1,3-propanediol, 2,7-diaminofluorene, 4,4'-diaminooctafluorobiphenyl, 3,3'-diaminobenzidine, 2,7-diamino-9-fluorenone, 3,5,3',5'-tetrabromo-biphenyl-4,4'-diamine, 2,2'-dichloro[1,1'-biphenyl]-4,4'-diamine, 3,9-diamino-1,11-dimethyl-5,7-dihydro-dibenzo(a,c)cyclohepten-6-one, dibenzo(1,2)dithiine-3,8-diamine, 3,3'-diaminobenzophenone, 3,3'-diaminodiphenylmethane, 4,4-bis-(3-amino-4-hydroxyphenyl)-valeric acid, 2,2-bis(3-amino-4-hydroxyphenyl)-hexafluoropropane, 2,2-bis(3-amino-4-methylphenyl)-hexafluoropropane, tetrabromo methylenedianiline, 2,7-diamino-9-fluorenone, 2,2-bis(3-aminophenyl)hexafluoropropane, bis-(3-amino-4-chlorophenyl)-methanone, bis-(3-amino-4-dimethyl-amino-phenyl)-methanone, 3-[3-amino-5-(trifluoromethyl)benzyl]-5-(trifluoromethyl)aniline, 1,5-diamino-naphthalene, benzidine-3,3'-dicarboxylic acid, 4,4'-diamino-1,1'-binaphthyl, 4,4'-diaminodiphenyl-3,3'-diglycolic acid, dihydroethidium, o-dianisidine, 2,2'-dichloro-5,5'-dimethoxybenzidine, 3-methoxybenzidine, 3,3'-dichlorobenzidine (diphenyl-d6), 2,2'-bis(trifluoromethyl)benzidine, 3,3'-bis(trifluoromethyl)benzidine, 3,3'-dichloro-benzidine-d6, tetramethylbenzidine, di-(aminophenyl)alkylen, and from amino compounds listed below, which do not carry two amino groups and are taken as derivatives with at least one additional amino group: aniline, 4-amino-2,3,5,6-tetrafluorobenzoic acid, 4-amino-3,5-diiodobenzoic acid, 4-amino-3-methylbenzoic acid, 4-amino-2-chlorobenzoic acid, 4-aminosalicylic acid, 4-aminobenzoic acid, 4-aminophthalic acid, 1-(4-aminophenyl)ethanol, 4-aminobenzyl alcohol, 4-amino-3-methoxybenzoic acid, 4-aminophenyl ethyl carbinol, 4-amino-3-nitrobenzoic acid, 4-amino-3,5-dinitrobenzoic acid, 4-amino-3,5-dichlorobenzoic acid, 4-amino-3-hydroxybenzoic acid, 4-aminobenzyl alcohol hydrochloride, 4-aminobenzoic acid hydrochloride, pararosaniline base, 4-amino-5-chloro-2-methoxybenzoic acid, 4-(hexafluoro-2-hydroxyisopropyl)aniline, piperazine-p-amino benzoate, 4-amino-3,5-dibromobenzoic acid, isonicotinic acid hydrazide p-aminosalicylate salt, 4-amino-3,5-diiodosalicylic acid, 4-amino-2-methoxybenzoic acid, 2-[2-(4-aminophenyl)-2-hydroxy-1-(hydroxymethyl)ethyl]isoindoline-1,3-dione, 4-amino-2-nitrobenzoic acid, ethyl 2-(4-aminophenyl)-3,3,3-trifluoro-2-hydroxypropanoate, ethyl 2-(4-amino-3-methylphenyl)-3,3,3-trifluoro-2-hydroxypropanoate, ethyl 2-(4-amino-3-methoxyphenyl)-3,3,3-trifluoro-2-hydroxypropanoate, 4-aminon-aphthalene-1,8-dicarboxylic acid, 4-amino-3-chloro-5-methylbenzoic acid, 4-amino-2,6-dimethylbenzoic acid, 4-amino-3-fluorobenzoic acid, 4-amino-5-bromo-2-methoxybenzenecarboxylic acid, 3,3'-tolidine-5-sulfonic acid, or their derivatives, again with the proviso that compounds listed which do not carry two amino groups are taken as derivatives with at least one additional amino group.

The diamine groups D are commercial available or accessible by known methods. The second amino group is accessible for example by substitution reaction.

D is further especially more preferably selected from the group of the following compounds:

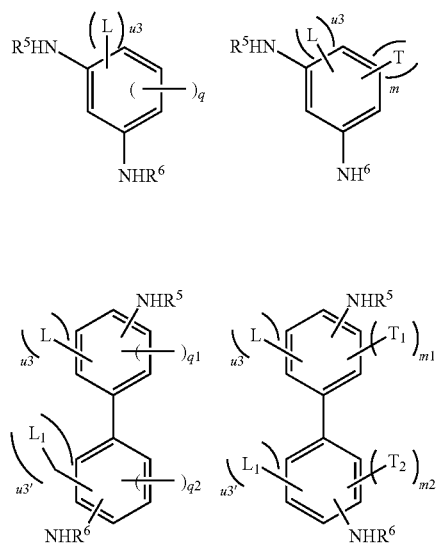

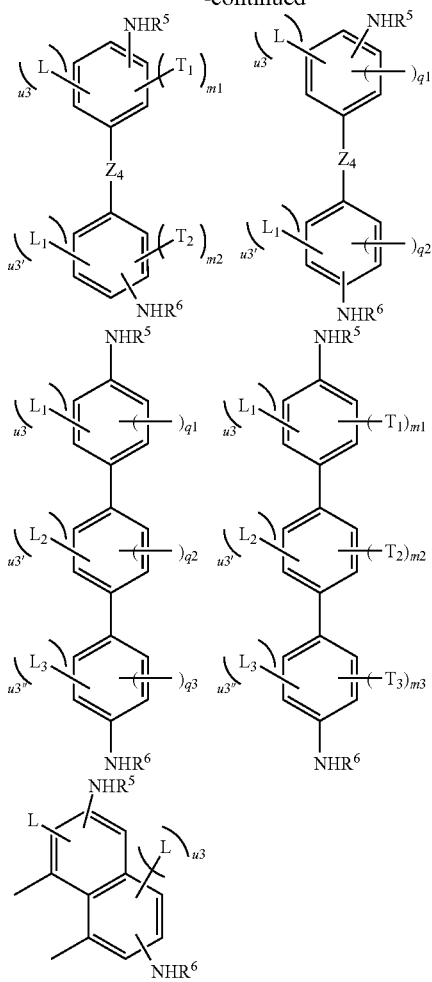

wherein

L, $L_1$, $L_2$ and $L_3$ are independently from each other —$CH_3$, —$COCH_3$, —$OCH_3$, nitro, nitrile, halogen, $CH_2$=CH—, $CH_2$=C($CH_3$)—, $CH_2$=CH—(CO)O—, $CH_2$=CH—O—, —$NR_5R_6$, $CH_2$=C($CH_3$)—(CO)O— or $CH_2$=C($CH_3$)—O—, T, $T_1$, $T_2$ and $T_3$ are independently from each other a substituted or unsubstituted straight-chain or branched $C_1$-$C_{24}$alkylene group, in which one or more C-atom, CH— or $CH_2$— group may independently from each other be replaced by a non-aromatic, aromatic, unsubstituted or substituted carbocyclic or heterocyclic group, and/or a heteroatom and/or by a linking group;

"—" is a single bond, q is an integer of 1 or 2; and q1, q2 and q3 are indepently from each other an integer from 0 to 2; preferably 1 or 2;

m is an integer of 1 or 2;

m1, m2 and m3 are indepently from each other an integer from 0 to 2; preferably 1 or 2;

u3, u3' and u3" are indepently from each other an integer from 0 to 2;

$R^5$, $R^6$ and $Z_4$ are as described above; preferably $Z_4$ is unsubstituted or substituted straight-chain or branched $C_1$-$C_{14}$alkylene group, $C_1$-$C_6$alkylene in which one or more, preferably non-adjacent, —C-atom, CH— or $CH_2$— group may be replaced by an oxygen or nitrogen atom;

more preferred $Z_4$ is methylen, ethylen, propylen, 2,2-dimethyl-propylen, butylen, pentylen, hexylen, $_2$(—O—$C_1$-$C_6$alkylen)methylen or $_2$(—(CO)O—$C_1$-$C_6$alkylen)methylen or the mono- or bi-radicals thereof, and wherein D is at least once linked to at least one group $S^1$ or $S^2$ via a single bond "—"; or via a side chain T, $T_1$, $T_2$ or $T_3$; or via group $Z_4$;

with the proviso that u3+q, or u3+m is ≤4;

u3+q1 and/or u3'+q2 or/and u3+m1, or/and u3'+m2, or/and u3"+q3, or/and u3"+m3 is ≤4;

q1+q2, and m1+m2; and q1+q2+q3, and m1+m2+m3 is ≥1.

Most preferred are diamine compounds according to the invention, wherein D is a selected from the group of the following compounds:

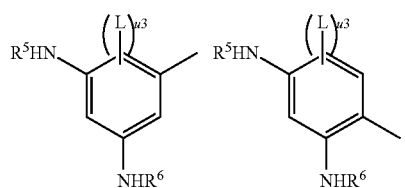

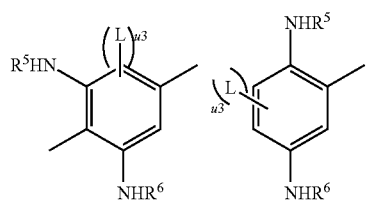

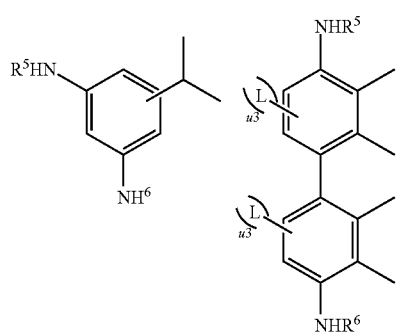

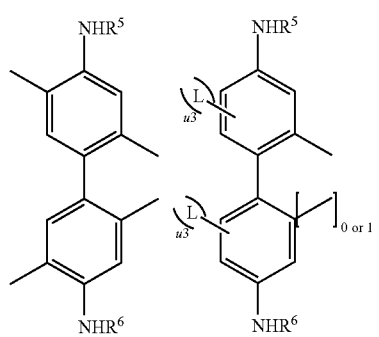

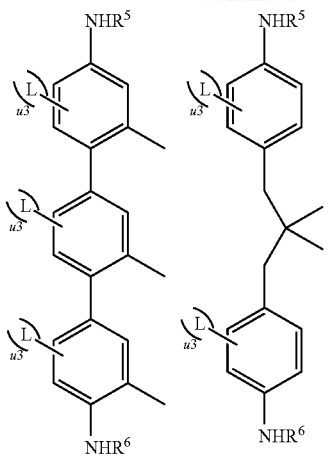

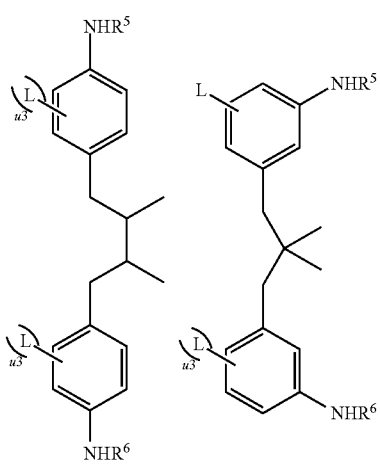

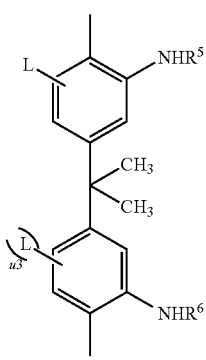

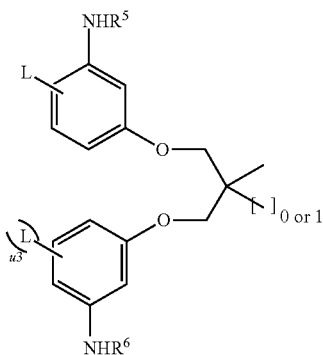

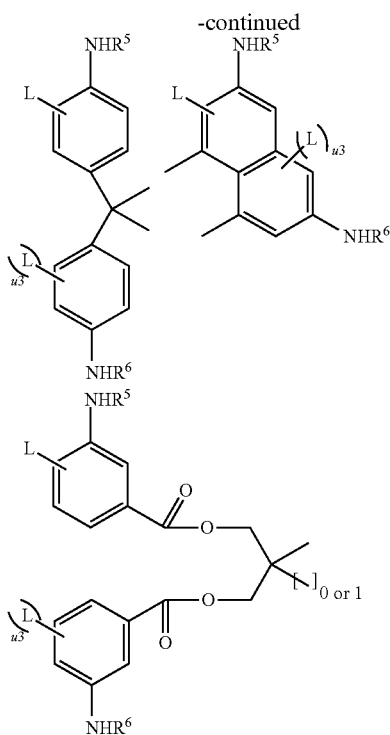

"—" denotes the linking(s) of D to $S^1$ or $S^2$ and represents a single bond; and L is —CH$_3$, —COCH$_3$, —OCH$_3$, nitro, nitrile, halogen, CH$_2$=CH—, CH$_2$=C(CH$_3$)—, CH$_2$=CH—(CO)O—, CH$_2$=CH—O—, —NR$^5$R$^6$, CH$_2$=C(CH$_3$)—(CO)O— or CH$_2$=C(CH$_3$)—O—, wherein:

$R^5$, $R^6$ each independently from each other represents a hydrogen atom or $C_1$-$C_6$alkyl;

u3 is an integer from 0 to 2.

Additionally, preferred diamine D of the present invention relate to diamines of formulae (VII) to (XV), comprising a group of formula (VII):

H$_2$N-alkylen-NH$_2$ (VII), wherein alkylen is at least once linked to the side chain of formula (I),

 (VIII)

wherein cyclohexylen group is at least once linked to the side chain of formula (I),

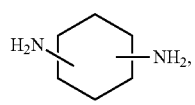 (IX)

wherein $X^4$ or/and cyclohexylen is at least once linked to the side chain of formula (I),

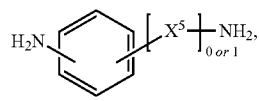 (X)

wherein $X^5$ or/and at phenylene is at least once linked to the side chain of formula (I), wherein $X^5$ is $C_1$-$C_{30}$alkyl,

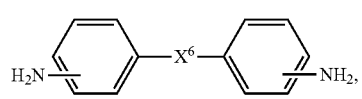 (XI)

wherein $X^6$ or/and phenylene is at least once linked to the side chain of formula (I),

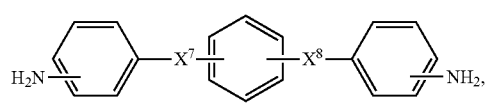 (XII)

wherein $X^7$, $X^8$ or/and phenylene is at least once linked to the side chain of formula (I),

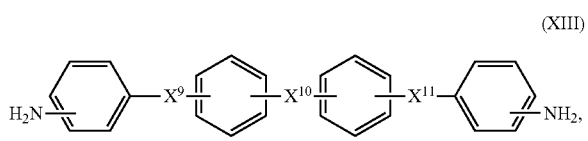 (XIII)

wherein $X^9$, $X^{10}$, $X^{11}$ or/and phenylene is at least once linked to the side chain of formula (I), and wherein $X^4$, $X^6$, $X^7$, $X^8$, $X^9$, $X^{10}$ and $X^{11}$ are independently from each other a bridging group or a single bond; or diamines of formulae (XIV) selected from the group of compounds given below:

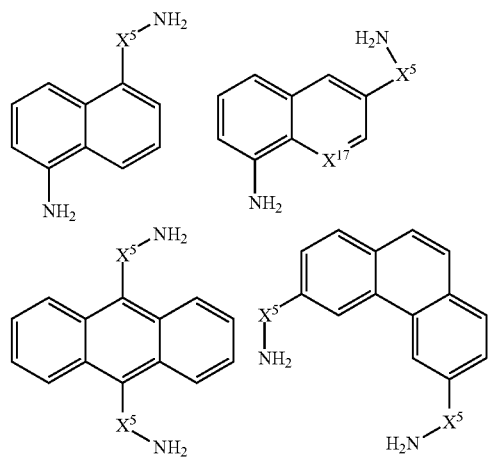

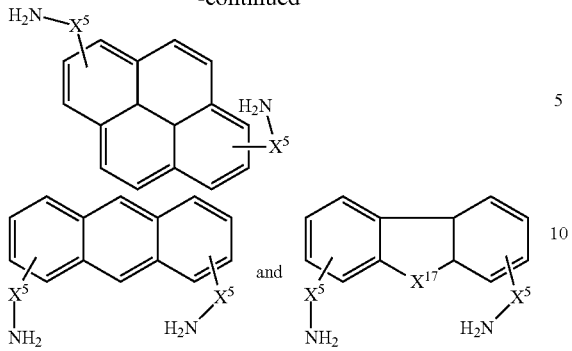

wherein $X^5$ has the meaning given above and $X^{17}$ is $CH_2$, O, NH; and which are linked at the aryl group to the side chain (I),
and (XV)

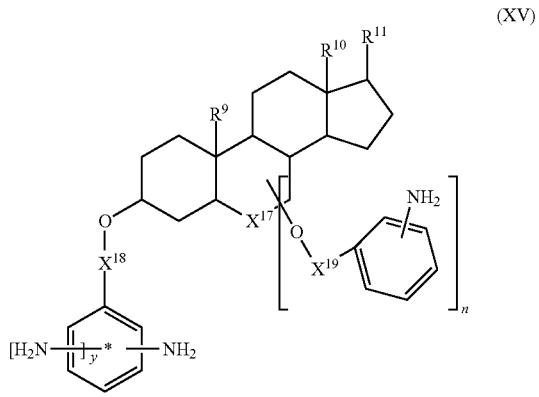

wherein
$R^9$, $R^{10}$, $R^{11}$ have independently from each other the above-described meaning, and $R^9$ and $R^{10}$ are $C_1$-$C_{30}$alkyl, and preferably methyl and $R^{11}$ is 2-methylheptane and n is 0, if y is 1 and y is 0 if n is 1, and y1 is a single or a double bond, and $X^{18}$ is carbonyl or a single bond or NH,
wherein $X^{17}$ is $CH_2$, O, NH, and which are linked at the aryl group to the side chain (I).

The term "alkylen" has the meaning of $(C_1$-$C_{12})$alkylene, which is branched, straight chain, substituted, unsubstituted, uninterrupted or interrupted by a linking group as defined above, and an alicyclic group, such as cyclohexylen or a $C_{17}$-$C_{40}$ alicyclic group, within the meaning and preferences as described above; or —Si$(R^3)_2$— or —O—Si$(R^3)_2$—, wherein $R^3$ has the meaning as given above.

Further, preferred in the present invention is diamine D (XV), wherein $X^{12}$ is a substituted or unsubstituted aliphatic, alicyclic group, preferably

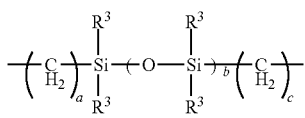

wherein $R^3$ has the same meaning and preferences as given above and a and c are independently from each other 1, 2 or 3, and c is an integer from 1 to 20; such as

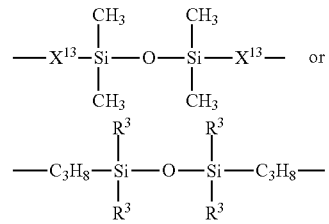

wherein $X^{13}$ is methylen, ethylen, propylene or butylen, and $R^3$ has the same meaning and is preferably methyl, ethyl or propyl.

Preferably, the diamine D (VIII) is on of formula (VIII-1)

(VIII-1)

wherein $R^9$ and $R^{10}$ are independently from each other hydrogen, halogen, hydroxyl, a carbocyclic or heterocyclic non-aromatic group or $C_1$-$C_{30}$alkyl, which is branched, straight chain, substituted, unsubstituted, uninterrupted or interrupted as described above and preferably interrupted by a linking group, and more preferably by a carbocyclic or heterocyclic non-aromatic group, such as cyclohexylen or a $C_{17}$-$C_{40}$ alicyclic group.

Preferably, the diamine D (IX) is of formula (IX-1)

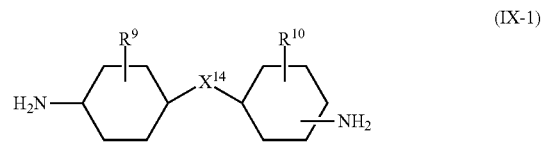

(IX-1)

wherein
$X^{14}$ is a bridging group or a single bond and preferably —COO—, —CONH—; a single bond, —O—, —S—, methylen, ethylen, propylene, $R^9$ and $R^{10}$ are independently from each other hydrogen, halogen, hydroxyl, a carbocyclic or heterocyclic non-aromatic group or $C_1$-$C_{30}$alkyl; preferably $X^{14}$ is a single bond, or, with $CF_3$, $OCF_3$, F, substituted or unsubstituted methylen, ethylen, propylene, butylen or pentylen and $R^9$ and $R^{10}$ are halogen or substituted or unsubstituted methylen, ethylen, propylene.

Preferably, the diamine D (X) is of formula (X-1)

(X-1)

wherein $R^{11}$, $R^{12}$, $R^{13}$ and $R^{14}$ are independently from each other hydrogen, halogen, hydroxyl, a carbocyclic or heterocyclic non-aromatic group or $C_1$-$C_{30}$alkyl. Preferably $C_1$-$C_{30}$alkyl is methyl, ethyl, propyl, butyl, pentyl or hexyl, 1,1'-cyclohexyl, 4-($C_1$-$C_{30}$ alkyl)-cyclohexyl, 3,4"-bis[4'-($C_1$-$C_{30}$alkyl)-1,1'-bi(cyclohexyl)-4-yl], 1,1'-bi(cyclohexyl)-4-yl, 2-pyridine, pyrrolidine-2,5-dione, which is unsubstituted or substituted by $CF_3$, $OCF_3$, F, benzyl, pentyl, benzoic acid ester, 4-(phenoxycarbonyl), carboxylic acid, —$SO_3H$, —$PO_3H$, —$OR^{15}$, wherein $R^{15}$ is $C_1$-$C_{30}$ alkyl, preferably —$C_{12}H_{25}$; unsubstituted or substituted benzyl, preferably, the two $NH_2$ groups of (X-1) are in meta or para position of the phenylene ring; further preferred structures of (X-1) are:

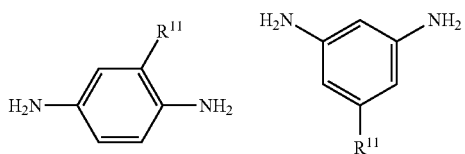

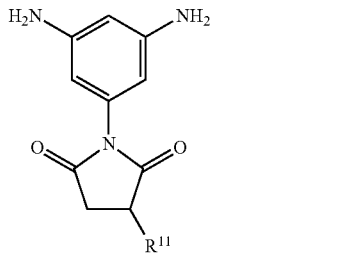

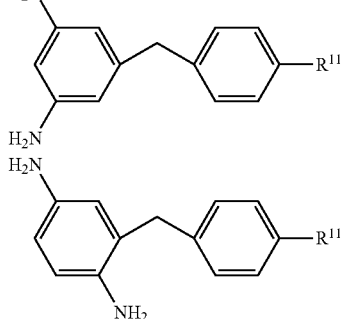

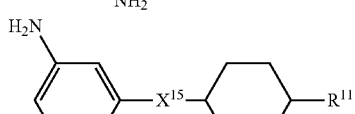

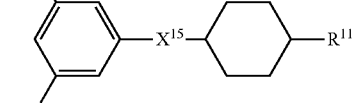

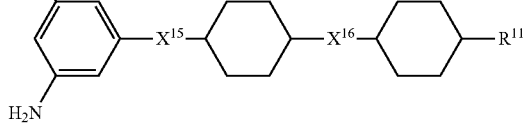

wherein $R^{11}$ has the meaning and preferences as given above, $X^{15}$ and $X^{16}$ are independently from each other a single bond or $C_1$-$C_{30}$alkyl, preferably $C_1$-$C_6$ alkyl, —COO— and —CONH—; —COO($C_1$-$C_6$alkylene)-, —CONH($C_1$-$C_6$alkylene)-.

Further preferred diamine compounds (X) are 1-hexa-decanoxy-2,4-diaminobenzene, 1-octadecanoxy-2,4-diaminobenzene, hexadecanoxy(3,5-diaminonbenzoyl), octadecanoxy(3,5-diaminobenzoyl).

Preferably, the diamine D (XI) is of formula (XI-1)

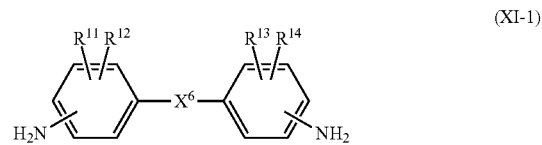

(XI-1)

wherein $X^6$ has the meaning and preferences as given above, and is preferably for example —O—, —S— or substituted or unsubstituted $C_1$-$C_6$alkylen, —O—($CH_2CH_2O$)n-; —O—($C_1$-$C_{12}$alkyl)n-O—, —S—($C_1$-$C_{12}$alkyl)n-S—, triazine, 1,3,5-triazinane-2,4,6-trione, 1,1'-cyclohexylene, $NR^5$(($C_1$-$C_6$alkyl)n$NR^6$), -(piperidine)$_{n1}$-($C_1$-$C_6$alkyl)n-(piperidine)n, wherein n is an integer from 1 to 6, and n1 are an integer from 0 to 6, wherein $R^{11}$, $R^{12}$, $R^{13}$ and $R^{14}$ have independently from each other the meaning and preferences as given above.

Further preferred diamine D (XI-1) is:

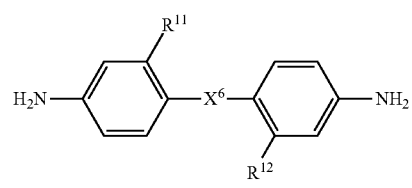

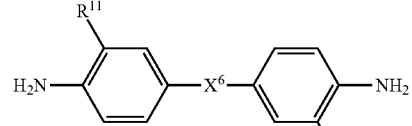

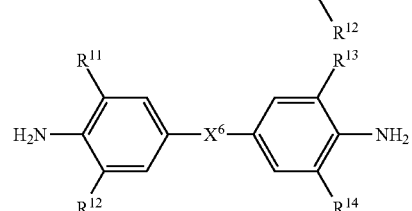

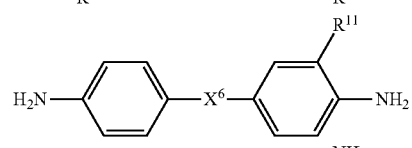

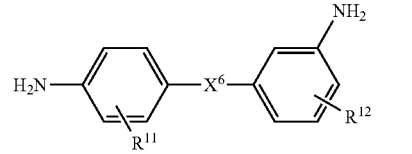

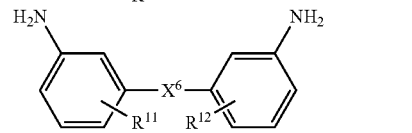

wherein $R^{11}$ and $R^{12}$ are independently from each other have the same meaning as given above, and which are preferably hydrogen, $C_1$-$C_6$alkyl, hydroxy, or 4-($C_1$-$C_{30}$alkyl)-cyclohexyl or 3,4"-bis[4'-($C_1$-$C_{30}$ alkyl)-1,1'-bi(cyclohexyl)-4-yl]. More preferred are diamine D (XI) given below:

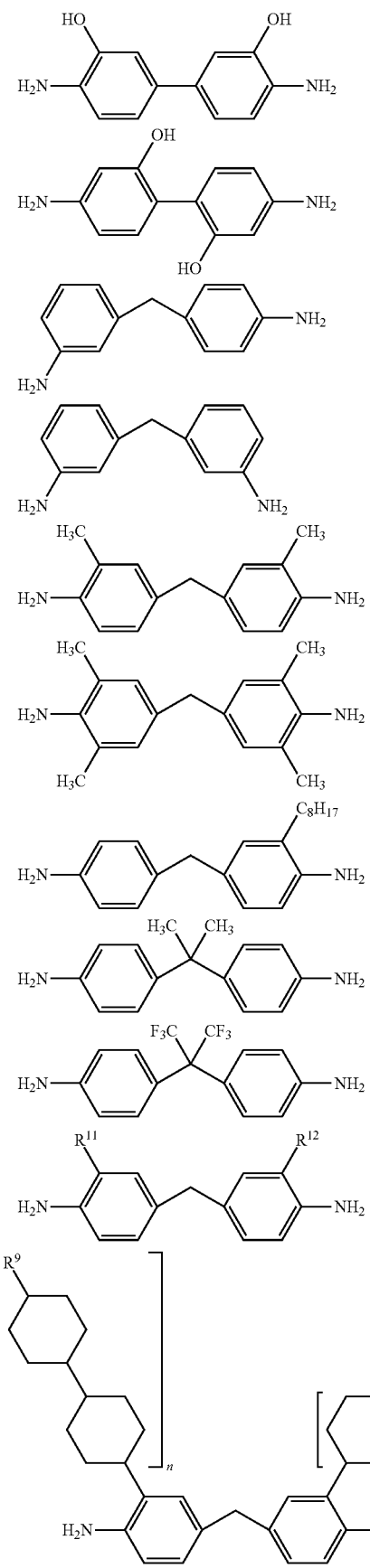

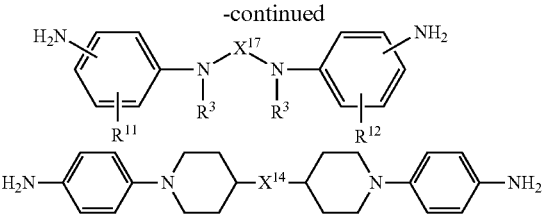

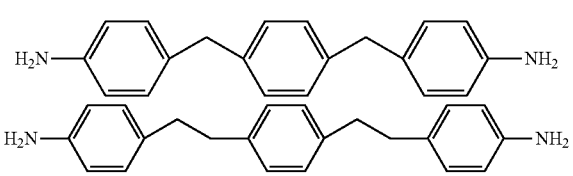

wherein n is independently from each other 0 or 1 and $R^3$, $R^{11}$, $R^{11}$, $X^{14}$ and $X^{17}$ have the same meanings and preferences as given above, and further more preferred are diamine compounds (XI) 4,4'-diaminodiphenyl, 4,4'-diaminodiphenyl-3,3'-dimethoxy, 4,4'-diaminodiphenyl-3,3'-dimethyl, 4,4'-diaminodiphenyl-3,3'-dihydroxy, 4,4'-diamino-diphenyl-methane, 4,4'-diaminodi-phenylsulfide, 4,4'-diaminodiphenylsulfone, 4,4'-diaminodiphenylcarbonyl, 4,4'-diaminodiphenyl oxomethylene, 4,4'-diaminodiphenyl-bis(trifluoromethyl)-methylene, 4,4'-diaminodiphenyl-bis(trifluoromethyl)methylene-3,3'-dimethoxy or 4,4'-diaminodiphenyl-bis(trifluoromethyl)methylene-3,3'-dihydroxy, 4,4'-diaminodiphenyl ether, 4,4'-(p-phenyleneiso-propylidene)bisaniline, 2,2-bis[4-(4-aminophenoxy)phenyl]-hexafluoro-propane, 2,2'-bis 4-4-amino-2-trifluoro-methyl-phenoxy-)phenyl) hexafluoropropane, 4,4'-diamino-2,2'-bis/trifluoromethyl)-biphenyl, 4,4'-bis[4-amino-2-trifluoromethyl)phenoxy]-octafluorobiphenyl.

Preferably, the diamine D (XII) and (XII) are diamines, wherein $X^7$ and $X^8$, $X^9$ and $X^{10}$ or $X^{11}$ are a single bond or $C_1$-$C_{30}$alkyl.

Preferably, $X^7$ and $X^8$, $X^9$ and $X^{10}$ or $X^{11}$ are independently from each other a single bond, —O-alkoxy-, such as —O-methylen-, methylen-O—; $C_1$-$C_{12}$alkylen such as methylene, ethylen, propylene, butylen, pentylen or hexylen, substituted or unsubstituted 1,1'-cyclohexylene, —SO—, —S—, —SO$_2$—, —O—, —N($R^{25}$)—, —C(CH$_3$)$_2$—, —C(CF$_3$)$_2$—, 1,1'-cyclohexyl, substituted or unsubstituted 4-(C$_1$-C$_{30}$ alkyl)-cyclohexyl, substituted or unsubstituted 3,4"-bis[4'-(C$_1$-C$_{30}$alkyl)-1,1'-bi(cyclohexyl)-4-yl], 1,1'-bi(cyclohexyl)-4-yl, wherein $R^{11}$ and $R^{12}$ are indepnetly from each other preferably hydrogen, methyl, ethyl, propyl, butyl, pentyl or hexyl;

preferably $X^{10}$ is —SO—, —SO$_2$—, —O—, —N(CH$_3$)—, —C(CH$_3$)$_2$—, —C(CF$_3$)$_2$—, 1,1'-cyclohexyl, 4-(C$_1$-C$_{30}$ alkyl)-cyclohexyl, 3,4"-bis[4'-(C$_1$-C$_{30}$ alkyl)-1,1'-bi(cyclohexyl)-4-yl] or 1,1'-bi(cyclohexyl)-4-yl, and wherein $X^9$ and $X^{11}$ are identical and are methylene, ethylen, propylene, butylen, pentylen, hexylen or —O—;

wherein n is an integer from 0 to 3, preferably, 0 or 1; and if n is 0 than $X^9$ and $X^{11}$ are identical and are methylene, ethylene, propylene, butylene, pentylene, hexylene, —O—, —S—, —C(CH$_3$)$_2$—, —C(CF$_3$)$_2$—.

Further preferred diamine D of (XII) is:

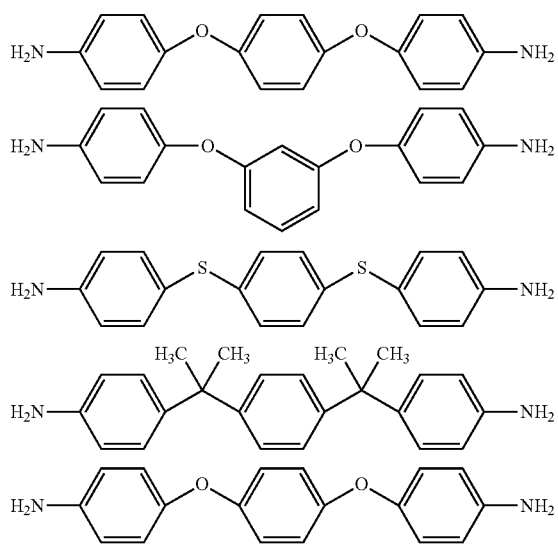
Further preferred diamine D of (XIII) are:
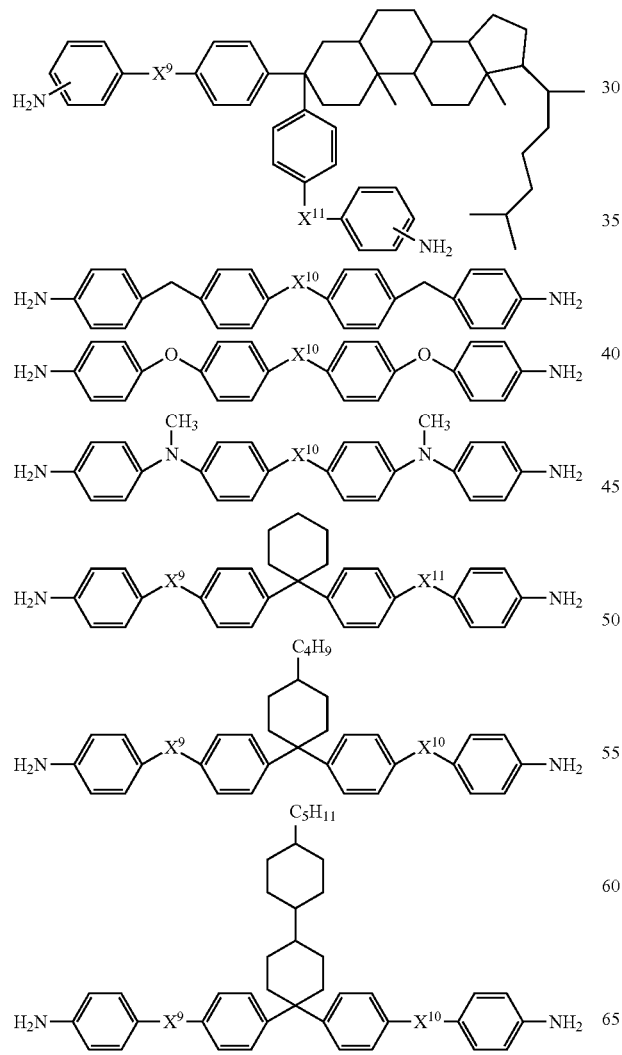
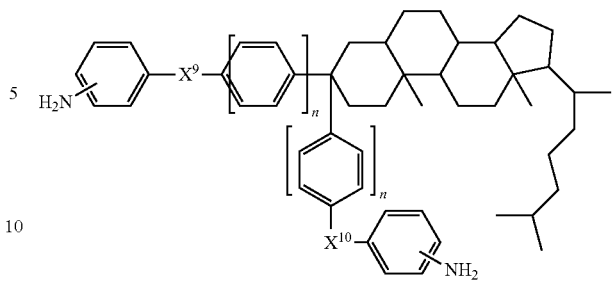
wherein n is 0 or 1, and wherein $X^7$ and $X^8$, $X^9$ and $X^{10}$ or $X^{11}$ have the above given meanings and preferences.
Preferably the diamine D (XIV) is 1,5-diaminonaphthalene, 2,7-diaminofluorene.
Preferably the diamine D (XV) is a compound as given below:
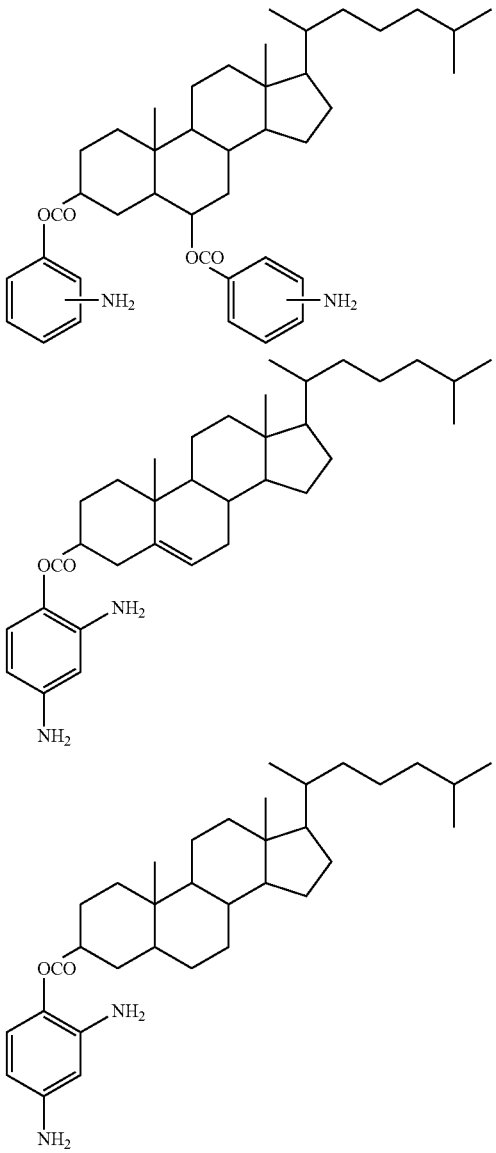

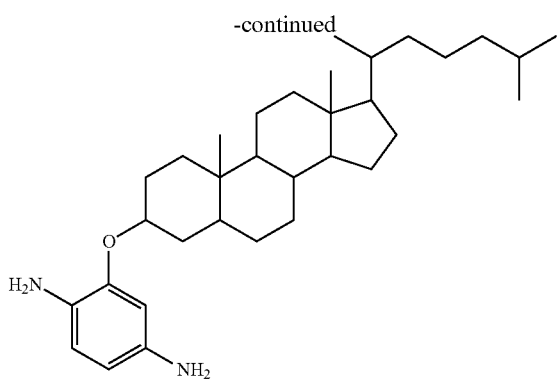

and further, 1-cholesteryl-oxy-2,4-diamino-benzene, 1-cholestanyloxy-2,4-diaminobenzene, cholesteryloxy(3,5-diamino-benzoyl), cholestan-yloxy(3,5-diaminobenzoyl).

Further, enclosed by reference are diamines as described in EP-A-1,818,354 on page 10, lines 48 to 58 and on page 11, lines 1 to 19.

Furtehr, the diamine represents an optionally substituted aliphatic, aromatic or alicyclic diamino group having from 1 to 40 carbon atoms and preferably made from or selected from the following group of structures: aniline, p-phenylenediamine, m-phenylenediamine, benzidine, diaminofluorene, or their derivatives, with the proviso that compounds listed which do not carry two amino groups are taken as derivatives with at least one additional amino group, and more preferably made from or selected from the following commercially available amino compounds (example of suppliers: Aldrich, ABCR, ACROS, Fluka) which can also be used as comonomers:

4-amino-2,3,5,6-tetrafluorobenzoic acid
4-amino-3,5-diiodobenzoic acid, 3,4-diaminobenzoic acid
4-amino-3-methylbenzoic acid,
4-amino-2-chlorobenzoic acid
4-aminosalicylic acid
4-aminobenzoic acid
4-aminophthalic acid
1-(4-aminophenyl)ethanol
4-aminobenzyl alcohol
4-amino-3-methoxybenzoic acid
4-aminophenyl ethyl carbinol
4-amino-3-nitrobenzoic acid
4-amino-3,5-dinitrobenzoic acid
4-amino-3,5-dichlorobenzoic acid
4-amino-3-hydroxybenzoic acid
4-aminobenzyl alcohol hydrochloride
4-aminobenzoic acid hydrochloride
pararosaniline base
4-amino-5-chloro-2-methoxybenzoic acid
4-(hexafluoro-2-hydroxyisopropyl)aniline
piperazine-p-amino benzoate
4-amino-3,5-dibromobenzoic acid
isonicotinic acid hydrazide p-aminosalicylate salt
4-amino-3,5-diiodosalicylic acid
4-amino-2-methoxybenzoic acid
2-[2-(4-aminophenyl)-2-hydroxy-1-(hydroxymethyl)ethyl]isoindoline-1,3-dione
4-amino-2-nitrobenzoic acid
2,4-diaminobenzoic acid
p-aminobenzoic acid,
[3,5-3h]-4-amino-2-methoxybenzoic acid
L-(+)-threo-2-amino-1-(4-aminophenyl)-1,3-propanediol
L-(+)-threo-2-(N,N-dimethylamino)-1-(4-aminophenyl)-1,3-propanediol
ethyl 2-(4-aminophenyl)-3,3,3-trifluoro-2-hydroxypropanoate
ethyl 2-(4-amino-3-methylphenyl)-3,3,3-trifluoro-2-hydroxypropanoate
ethyl 2-(4-amino-3-methoxyphenyl)-3,3,3-trifluoro-2-hydroxypropanoate
3,4-diaminobenzyl alcohol dihydrochloride
4-aminonaphthalene-1,8-dicarboxylic acid
4-amino-3-chloro-5-methylbenzoic acid
4-amino-2,6-dimethylbenzoic acid
4-amino-3-fluorobenzoic acid
4-amino-5-bromo-2-methoxybenzenecarboxylic acid
2,7-diaminofluorene
4,4'-diaminooctafluorobiphenyl
3,3'-diaminobenzidine
3,3',5,5'-tetramethylbenzidine
3,3'-dimethoxybenzidine
o-tolidine
3,3'-dinitrobenzidine
2-nitrobenzidine
3,3'-dihydroxybenzidine
o-tolidine sulfone
benzidine,
3,3'-dichlorobenzidine
2,2',5,5'-tetrachlorobenzidine,
benzidine-3,3'-dicarboxylic acid
4,4'-diamino-1,1'-binaphthyl
4,4'-diaminodiphenyl-3,3'-diglycolic acid
dihydroethidium
o-dianisidine
2,2'-dichloro-5,5'-dimethoxybenzidine
3-methoxybenzidine
3,3'-dichlorobenzidine (diphenyl-d6),
2,7-diamino-9-fluorenone
3,5,3',5'-tetrabromo-biphenyl-4,4'-diamine
2,2'-bis(trifluoromethyl)benzidine
2,2'-dichloro[1,1'-biphenyl]-4,4'-diamine
3,9-diamino-1,11-dimethyl-5,7-dihydro-dibenzo(a,c)cyclohepten-6-one
3,3'-bis(trifluoromethyl)benzidine
dibenzo(1,2)dithiine-3,8-diamine
3,3'-tolidine-5-sulfonic acid
3,3'-dichlorobenzidine-d6
tetramethylbenzidine
3,3'-diaminobenzophenone, 3,3'-diaminodiphenylmethane,
4,4-bis-(3-amino-4-hydroxyphenyl)-valeric acid
2,2-bis(3-amino-4-hydroxyphenyl)hexafluoropropane
2,2-bis(3-amino-4-methylphenyl)hexafluoropropane
tetrabromo methylenedianiline
2,7-diamino-9-fluorenone
2,2-bis(3-aminophenyl)hexafluoropropane
bis-(3-amino-4-chloro-phenyl)-methanone
bis-(3-amino-4-dimethylamino-phenyl)-methanone
3-[3-amino-5-(trifluoromethyl)benzyl]-5-(trifluoromethyl)aniline
1,5-diaminonaphthalene
or their derivatives, again with the proviso that compounds listed which do not carry two amino groups are taken as derivatives with at least one additional amino group.
Preferred examples of additional other diamines are:
ethylenediamine, 1,3-propylenediamine, 1,4-butylenediamine, 1,5-pentylenediamine, 1,6-hexylenediamine, 1,7-heptylenediamine, 1,8-octylenediamine, 1,9-nonylenediamine, 1,10-decylenediamine, 1,11-undecylenediamine, 1,12-dodecylenediamine, α,α'-diamino-m-xylene, α,α'- diamino-p-xylene, (5-amino-2,2,4-trimethylcyclopentyl) methylamine, 1,2-diaminocyclohexane, 4,4'-diaminodicyclohexylmethane, 1,3-bis(methylamino)cyclohexane, 4,9-dioxadodecane-1,12-diamine, 3,5-diaminobenzoic acid methyl ester, 3,5-diaminobenzoic acid hexyl ester, 3,5-diaminobenzoic acid dodecyl ester, 3,5-diaminobenzoic acid isopropyl ester, 4,4'-methylenedianiline, 4,4'-ethylenedianiline, 4,4'-diamino-3,3'-dimethyldiphenylmethane, 3,3',5,5'-tetramethylbenzidine, 4,4'-diaminodiphenyl sulfone, 4,4'-diaminodiphenyl ether, 1,5-diaminonaphthalene, 3,3'-dimethyl-4,4'-diaminobiphenyl, 3,4'-diaminodiphenyl ether, 3,3'-diaminobenzophenone, 4,4'-diaminobenzophenone, 4,4'-diamino-2,2'-dimethylbibenzyl, bis[4-(4-aminophenoxy)phenyl]sulfone, 1,4-bis(4-aminophenoxy)benzene, 1,3-bis(4-aminophenoxy)benzene, 1,3-bis(3-aminophenoxy)benzene, 2,7-diaminofluorene, 9,9-bis(4-aminophenyl)fluorene, 4,4'-methylene-bis(2-chloroaniline), 4,4'-bis(4-aminophenoxy)biphenyl, 2,2',5,5'-tetrachloro-4,4'-diaminobiphenyl, 2,2'-dichloro-4,4'-diamino-5,5'-dimethoxybiphenyl, 3,3'-dimethoxy-4,4'-diaminobiphenyl, 4,4'-(1,4-phenyleneisopropylidene) bisaniline, 4,4'-(1,3-phenyleneisopropylidene)bisaniline, 2,2-bis[4-(4-aminophenoxy)phenyl]propane, 2,2-bis[3-(4-aminophenoxy)phenyl]hexafluoropropane, 2,2-bis[3-amino-4-methylphenyl]hexafluoropropane, 2,2-bis(4-aminophenyl)hexafluoropropane, 2,2'-bis[4-(4-amino-2-trifluoromethylphenoxy)phenyl]hexafluoropropane, 4,4'-diamino-2,2'-bis(trifluoromethyl)biphenyl, and 4,4'-bis[(4-amino-2-trifluoromethyl)phenoxy]-2,3,5,6,2',3',5',6'-octafluorobiphenyl, as well as diamines disclosed in U.S. Pat. No. 6,340,506, WO-00/59966 and WO-01/53384.

The polymers of the present invention have a molecular weight MW between 1 000 and 5 000 000, preferably however between 5 000 and 2 000 000, especially advantageously however between 10 000 and 1 000 000.

The number of monomer building blocks from which the polymer chains according to the invention are synthesised can vary within a wide range. It is generally from 2 to 2000, but especially from 3 to 200.

The polymers, copolymers according to the invention may be used as a single polymer, copolymer or as mixture with other polymers, copolymers, oligomers, monomers, photoactive polymers, photoactive copolymers, photoactive oligomers and/or photoactive monomers. Thus the properties of the layer may be modified to give what is sought. For example, an induced pretilt angle, good surface wetting, high voltage holding ratio, a specific anchoring energy etc. may be obtained.

The present invention also relates to the use of the polymer materials, or copolymer materials comprising a monomer of formula (I) as orienting layer for liquid crystals.

Further, the present invention relates to a method for the preparation of an alignment layer for liquid crystals comprising irradiating polymer material or copolymer materials, which comprises repeating units of formula (I) or the composition comprising polymer material or copolymer materials, which comprises a monomer of formula (I) with aligning light, and optionally subsequently bringing into contact said alignment layer with a composition comprising polymerizable liquid crystals In general the composition is applied by general coating and printing methods known in the art. Coating methods are for example spin coating, air doctor coating, blade coating, knife coating, reverse-roll coating, transfer roll coating, gravure roll coating, kiss roll coating, cast coating, spray coating, roll to roll coating, slot-orifice coating, calendar coating, electrodepositing coating, dip coating or die coating.

Printing methods are for example relief printing such as flexographic printing, ink jet printing, intaglio printing such as direct gravure printing or offset gravure printing, lithographic printing such as offset printing, or stencil printing such as screen printing.

In the context of the present invention liquid crystals has the meaning of polymerizable or switchable liquid crystals. The polymerizable liquid crystal is preferably a photo-polymerisable liquid crystal, LCP.

Further, preferred is a method of the invention for the preparation of an orientation layer for liquid crystals comprising irradiating copolymer materials, which comprises repeating units of formula (I) having main absorption band in the UV-B- and/or UV-A spectrum to the near visible spectrum to 430 nm, preferably which have their highest absorption in the UV-A spectrum, and comonomers comprising photoreactive groups having a main absorption in the UV-C and/or UV-B spectrum.

In dependence from the envisaged method, e.g the used irradiation wave length(s) the ratio of the comonomers of the copolymers of the invention may vary.

For example it may be of advantage to reduce the UV-B exposure, have no UV-B exposure, in the aligning light.

By providing specific ratios of monomer to comonomer this can be achieved

Hence, in a further preferred embodiment the copolymers have a weight ratio of the first monomer to the second comonomer, preferably the comonomer X, is 99.5:0.5 to 1:1, more preferably from 99:1 to 80:20, and particularly preferred from 99:1 to 90:10.

In addition, it may be advantageful to aligning with different UV-wave length, such as UV-B and UV-A, or UV-A, UV-B and UV-C exposure.

Therefor, in addition, preferred are copolymers have a weight ratio of the first monomer to the second comonomer, preferably the comonomer X, is 90:10 to 30:70, more preferably from 90:10 to 50:50, and particularly preferred from 90:10 to 60:40.

A preferred method comprises a method for the preparation of an alignment layer according to the present invention, wherein one or more oligomers, dendrimers, copolymer or polymers according to the present invention or a composition according to the present invention, preferably in solution, is applied to a support, which is optionally provided with an electrode, and optionally after prior imidisation, said applied oligomers, dendrimers or polymers are reacted by irradiation with aligning light, preferably irradiating for orientation with 1.5 mJ·cm$^{-2}$ for <40 seconds, preferably <20 seconds, more preferably <10 seconds, and optionally subsequently bringing into contact said alignment layer with a composition comprising polymerizable liquid crystals.

Further, preferred method comprises
  applying a composition comprising a polymer material or copolymer materials of formula (I) within the meaning and preferences as described above to a carrier,
  and irradiating the polymer material or copolymer materials which comprises repeating units of formula (I) or the composition comprising polymer material or copolymer materials which comprises a monomer of formula (I) with aligning light; preferably Especially preferred is the method, wherein two irradiation processes are conducted one with aligning light and the other with or without aligning light, such as isotropic light.

In the context of the present invention the term carrier has the same meaning as support.

The term "carrier" as used in the context of the present invention is preferably transparent or not-transparent, flexible or not-flexible, and is preferably glass or plastic substrates, polymer films, such as polyethyleneterephthalat (PET), tri-acetyl cellulose (TAC), such as TAC foil, polypropylen, optionally coated with indium tin oxide (ITO), however not limited to them.

In general the composition is applied by general coating and printing methods known in the art, such as spin-coating, meniscus-coating, wire-coating, slot-coating, offset-printing, flexo-printing, gravure-printing, ink jet printing may be used. Coating methods are for example spin coating, air doctor coating, blade coating, knife coating, reverse-roll coating, transfer roll coating, gravure roll coating, kiss roll coating, cast coating, spray coating, slot-orifice coating, calendar coating, electrodepositing coating, dip coating or die coating.

Printing methods are for example relief printing such as flexographic printing, ink jet printing, intaglio printing such as direct gravure printing or offset gravure printing, lithographic printing such as offset printing, or stencil printing such as screen printing. In the context of the present invention, "aligning light" is light of wavelengths, which can initiate photoreaction, especially, which can induce anisotropy in the photoalignment layer of (I). Preferably, the wavelengths are in the UV-A, UVB and/or UV/C-range, or in the visible range. It depends on the photoalignment compound, which wavelengths are appropriate. Preferably, the photo-reactive groups are sensitive to visible and/or UV light. A further embodiment of the invention concerns the generating of aligning light by laser light. By fine tuning the aligning light wave length spectrum, special light sources may be used with specific wavelengths or special bandpass filters to allow or pass specific wavelengths.

The UV light is preferably selected according to the absorption of the photo-reactive groups, i.e. the absorption of the film should overlap with the emission spectrum of the lamp used for the LP-UV irradiation, more preferably with linearly polarized UV light. The intensity and the energy used are chosen depending on the photosensitivity of the material and on the orientation performances which are targeted. In most of the cases, very low energies (few mJ/cm2) already lead to high orientation quality.

More preferably, "aligning light" is at least partially linearly polarized, elliptically polarized, such as for example circularly polarized, or non-polarized, most preferably circularly polarized, or non-polarized light exposed obliquely, or at least partially linearly polarized light. Especially, most preferred aligning light denotes substantially polarised light, especially linearly polarised light; or aligning light denotes non-polarised light, which is applied by an oblique irradiation.

More preferably, the aligning light is UV light, preferably linearly polarized UV light. Thus, for the production of orienting layers in regions which are limited selectively by area, a solution of the polymer material obtained can applied. For example, firstly be produced and can be spun in a spin-coating apparatus on to a carrier which is optionally coated with an electrode (for example, a glass plate coated with indium-tin oxide (ITO) such that homogeneous layers of 0.05-50 µm thickness result. Subsequently, the regions to be oriented can be exposed e.g. to a mercury high-pressure lamp, a xenon lamp or a pulsed UV laser using a polarizer and optionally a mask in order to form structures. The duration of the exposure depends on the output of the individual lamps and can vary from a few minutes to several hours. The photoreaction can, however, also be effected by irradiating the homogeneous layer using filters which let through e.g. only the radiation which is suitable for the photo reaction.

The present invention also relates to orientation layers, comprising a polymer material or copolymer material, which comprises repeating units of formula (I) or a composition comprising said polymer material.

In the context the wording "orientation layer", has the same meaning and preferences as "alignment layer".

The use of the polymers or copolymers in accordance with the invention as orienting layers for liquid crystals as well as their use in of non-structured and structured optical and electro-optical components, especially for the production of hybrid layer elements, is also objects of the present invention.

Further, the present invention relates to optical or electro-optical elements comprising polymer material (I) or/and a composition comprising polymer material or copolymer material (I) or/and an orientation layer prepared by using polymer material (I).

The term "structured" refers to a variation in the azimuthal orientation, which is induced by locally varying the direction of the polarized aligning light.

In addition, the present invention relates to the use of the polymer material or copolymer materials according to the present invention as an orienting layer, for aligning organic or inorganic compounds, especially for aligning liquid crystals and liquid crystal polymers.

The present invention also relates to the use of the orienting layer of the invention in the manufacture of optical or electro-optical component and systems, especially multilayer systems, or devices for the preparation of
a display waveguide, a security or brand protection element, a bar code, an optical grating, a filter, a retarder, a 3-D-retarder, a compensation film, a reflectively polarizing film, an absorptive polarizing film, an anisotropically scattering film compensator and retardation film, a twisted retarder film, a cholesteric liquid crystal film, a guest-host liquid crystal film, a monomer corrugated film, a smectic liquid crystal film, a polarizer, a piezoelectric cell, a thin film exhibiting non linear optical properties, a decorative optical element, a brightness enhancement film, a component for wavelength-band-selective compensation, a component for multi-domain compensation, a component of multiview liquid crystal displays, an achromatic retarder, a polarization state correction/adjustment film, a component of optical or electro-optical sensors, a component of brightness enhancement film, a component for light-based telecommunication devices, a G/H-polarizer with an anisotropic absorber, a reflective circular polarizer, a reflective linear polarizer, a MC (monomer corrugated film), liquid crystal displays, especially twisted nematic (TN) liquid crystal displays, hybrid aligned nematic (HAN) liquid crystal displays, electrically controlled birefringence (ECB) liquid crystal displays, supertwisted nematic (STN) liquid crystal displays, optically compensated birefringence (OCB) liquid crystal displays, pi-cell liquid crystal displays, in-plane switching (IPS) liquid crystal displays, VA-IPS, fringe field switching (FFS) liquid crystal displays, vertically aligned (VA) liquid crystal displays; all above display types are applied in either transmissive or reflective or transflective mode.

The optical or electro-optical component and systems, especially multilayer systems and devices can be patterned or unpatterned.

The term patterning preferably denotes to birefringence patterning and/or thickness patterning and/or patterning of the optical axis orientation, and/or patterning of the degree of polymerization. Birefringence denotes the difference between the extra-ordinary and the ordinary index of refraction.

Thus the invention further relates to an optical or electro-optical elements, systems and devices device comprising polymer material or composition comprising said polymer material or copolymer materials, within the above given meaning and preferences.

Preferred are optical or electro-optical elements, systems and devices comprising orienting layers according to the present invention and at least one orientable layer, such as a liquid crystal layer or liquid crystal polymer layer.

An optical component, system or device creates, manipulates, or measures electromagnetic radiation.

An electro-optical component, system or device operates by modification of the optical properties of a material by an electric field. Thus it concerns the interaction between the electromagnetic (optical) and the electrical (electronic) states of materials.

The orienting material has the ability to align compounds, such as for example nematic liquid crystals, with their long axis along a preferred direction.

The present invention also relates to the use of the orienting layer according to the present invention, for aligning organic or inorganic compounds, especially for aligning liquid crystals.

The term "anisotropy" or "anisotropic" refers to the property of being directionally dependent. Something which is anisotropic may appear different or have different characteristics in different directions.

Preferred is the use for the induction of planar alignment, tilted or vertical alignment of adjacent liquid crystalline layers; more preferred is the use for the induction of planar alignment or vertical alignment in adjacent liquid crystalline layers.

Such alignment layers of the invention may be used in the production of optical or electro-optical devices having at least one orientation layer as well as unstructured and structured optical elements and multi-layer systems. Thus the invention further relates to an optical or electro-optical device comprising one or more oligomers, dendrimers or polymers according to the present invention in cross-linked form.

In the present invention photoreactive compounds were surprisingly found which give access to very fast orientation of liquid crystals. Herewith economic, less energy consumpting processes for the manufacturing of orientation layers for e.g. LCDs or retarder layers are accessible. Especially, the copolymers of the invention give access to very flexible manufacturing processes, by specifically selecting so that they adapt very well with the desired aligning light used in the manufacturing process. In addition, good orientation quality, such as high contrast, and stable orientation, such as azimuthal stability, with low energies of irradiation is accessed with these novel materials of the present invention. Also very much surprisingly it was found that copolymer of the invention shows excellent orientation and adhesion to the substrate even if irradiated by UVB, UVA or UVC light.

EXAMPLES

A) Synthesis Examples

Example 1

Synthesis of 8-{4-[(Z)-2-cyano-2-(3,5-dimethoxyphenyl)ethenyl]phenoxy}octyl poly-2-methylacrylate Preparation of 4-[(8-hydroxyoctyl)oxy]benzaldehyde

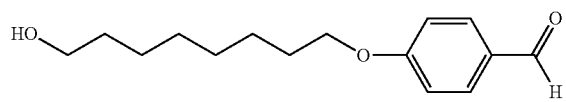 [SMILES: O=Cc1ccc(OCCCCCCCCO)cc1]

20.0 g (164 mmol) of 4-hydroxybenzaldehyde and 30.0 g (182 mmol) of 8-chlorooctan-1-ol are dissolved in 200 mL of N,N-dimethylformamide. 29.0 g (210 mmol) of potassium carbonate and 2.7 g (16 mmol) of potassium iodide are added and the suspension is heated to 100° C. After 48 h, the excess of potassium carbonate is filtered off and the resulting filtrate is poured to icy water. The aqueous layer is extracted twice with ethyl acetate. Combined organic layers are washed with brine and evaporated to dryness. The crude is purified twice on column chromatography ($SiO_2$, Heptane/ethyl acetate: 7/3) and dried overnight at 40° C. 25.6 g of 4-[(8-hydroxyoctyl)oxy]benzaldehyde are obtained as a yellow solid (62% yield). This material proves chromatographically homogenous and displays spectral characteristics consistent with its assigned structure.

Preparation of (2Z)-2-(3,5-dimethoxyphenyl)-3-{4-[(8-hydroxyoctyl)oxy]phenyl}prop-2-enenitrile

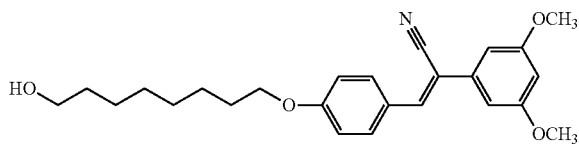 [SMILES: COc1cc(OC)cc(/C(C#N)=C/c2ccc(OCCCCCCCCO)cc2)c1]

5.0 g (20.0 mmol) of 4-[(8-hydroxyoctyl)oxy]benzaldehyde, 3.5 g (19.8 mmol) of 3,5-(dimethoxyphenyl)acetonitrile are dissolved in 50 mL of propan-2-ol. The solution is heated to 60° C. and 2.0 mL (2.0 mmol) of a one molar solution of tetrabuthylamoniumhydroxyde in methanol are added drop wise. After 2 h at 60° C., the reaction mixture is cooled to 0° C. The precipitate is filtered off, washed with cold propan-2-ol and recristalized in propan-2-ol. 3.5 g of (2Z)-2-(3,5-dimethoxyphenyl)-3-{4-[(8-hydroxyoctyl)oxy]phenyl}prop-2-enenitrile are obtained as a white solid (42% yield). This material proves chromatographically homogenous and displays spectral characteristics consistent with its assigned structure.

$^1$H NMR DMSO-$d_6$ 300 MHz: 7.99 (s, 1H), 7.94 (d, 2H), 7.09 (d, 2H), 6.86 (d, 2H), 6.56 (t, 1H), 4.32 (t, 1H), 4.05 (t, 2H), 3.81 (s, 6H), 3.37 (q, 2H), 1.73 (qi, 2H), 1.43-1.29 (m, 10H)

Preparation of 8-{4-[(Z)-2-cyano-2-(3,5-dimethoxyphenyl)ethenyl]phenoxy}octyl 2-methylacrylate

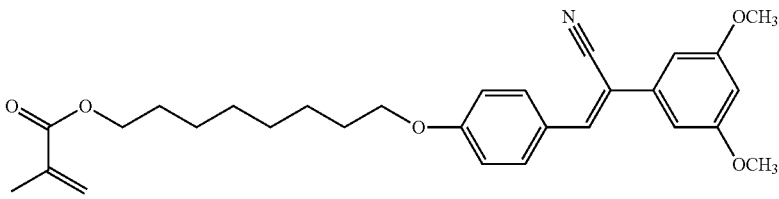 [SMILES: C=C(C)C(=O)OCCCCCCCCOc1ccc(/C=C(\C#N)c2cc(OC)cc(OC)c2)cc1]

2.5 g (6.10 mmol) of (2Z)-2-(3,5-dimethoxyphenyl)-3-{4-[(8-hydroxyoctyl)oxy]phenyl}prop-2-enenitrile, 75 mg (0.61 mmol) of 4-dimethylaminopyridine and 1.8 g (17.79 mmol) of triethylamine are dissolved in 40 mL of tetrahydrofurane. The solution is cooled to 0° C. and a solution 1.1 g (7.13 mmol) of methacrylic anhydride in 10 mL of tetrahydrofuran is added drop wise in 1 h at 0° C. After 2 h at 0° C., the reaction mixture is then allowed to heat up to room temperature. After 15 h, the reaction mixture is poured on icy water. The precipitate is filtered off, dried at 30° C. and recristalized in methanol with a small amount of 2,6-di-tert-buthyl-4-methylphenol. 2.14 g of 8-{4-[(Z)-2-cyano-2-(3,5-dimethoxyphenyl)ethenyl]phenoxy}octyl 2-methylacrylate are obtained as a white solid (73% yield). This material proves chromatographically homogenous and displays spectral characteristics consistent with its assigned structure. High-performance liquid chromatography, 97+% of purity with UV-detector at 330 nm.

Preparation of 8-{4-[(Z)-2-cyano-2-(3,5-dimethoxyphenyl)ethenyl]phenoxy}octyl poly-2-methylacrylate

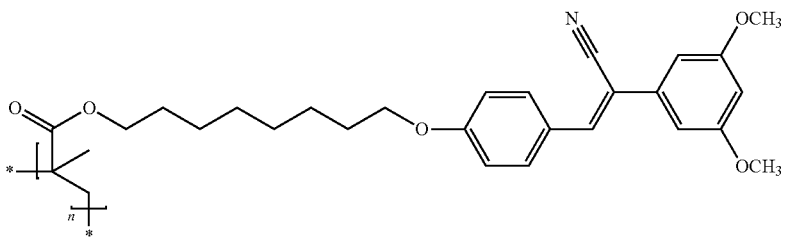

1.00 g (2.1 mmol) of 8-{4-[(Z)-2-cyano-2-(3,5-dimethoxyphenyl)ethenyl]phenoxy}octyl 2-methylacrylate is dissolved in 3 mL of degassed cyclohexanone. The solution is purged with argon (several vacuum-argon cycles) and heated to 60° C. A solution of 11.0 mg (0.07 mmol) of 2,2'-Azobis(2-methylpropionitrile) in 1.1 mL of cyclohexanone is added drop wise. After 36 h at 60° C., the reaction mixture is cooled to room temperature, diluted with 3 mL of tetrahydrofuran, and precipitated in 200 mL of cold methanol. The precipitate is filtered off, washed with methanol and dried overnight at 30° C. 0.92 g of 8-{4-[(Z)-2-cyano-2-(3,5-dimethoxyphenyl)ethenyl]phenoxy}octyl poly-2-methylacrylate are obtained as a white solid (92% yield). This material proves chromatographically homogenous and displays spectral characteristics consistent with its assigned structure. Size-exclusion chromatography (PS-equivalent), Mn 23,500; Mw 75,400; PDI 3.2. λ max of coated film=342 nm.

$^1$H NMR THF-d$_8$ 300 MHz: 7.87 (d, 2H), 7.58 (s, 1H), 6.93 (d, 2H), 6.79 (d, 2H), 6.44 (d, 1H), 3.96 (m, 4H), 3.76 (s, 6H), 1.86-1.70 (m, 2H), 1.64 (m, 2H), 1.55-1.27 (m, 10H), 1.16-0.83 (m, 3H).

Example 2

Synthesis of 8-{4-[(Z)-1-cyano-2-(3,5-dimethoxyphenyl)ethenyl]phenoxy}octyl poly-2-methylacrylate Preparation of {4-[(8-hydroxyoctyl)oxy]phenyl}acetonitrile

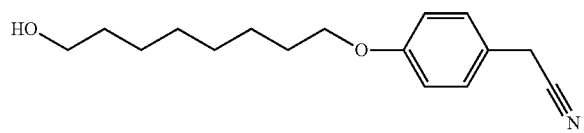 [SMILES: N#CCc1ccc(OCCCCCCCCO)cc1]

20.0 g (150 mmol) of (4-hydroxyphenyl)acetonitrile and 29.5 g (179 mmol) of 8-chlorooctan-1-ol are dissolved in 400 mL of N,N-dimethylformamide. 41.5 g (300 mmol) of potassium carbonate and 5.0 g (30 mmol) of potassium iodide are added and the suspension is heated to 80° C. After 48 h, the excess of potassium carbonate is filtered off and the resulting filtrate is poured to icy water. The aqueous layer is extracted twice with ethyl acetate. Combined organic layers are washed with brine and evaporated to dryness. The crude is purified twice on column chromatography (SiO$_2$, Heptane/ethyl acetate: 7/3) and dried overnight at 40° C. 24.5 g of {4-[(8-hydroxyoctyl)oxy]phenyl}acetonitrile are obtained as a yellow solid (62% yield). This material proves chromatographically homogenous and displays spectral characteristics consistent with its assigned structure.

Preparation of (2Z)-3-(3,5-dimethoxyphenyl)-2-{4-[(8-hydroxyoctyl)oxy]phenyl}prop-2-enenitrile

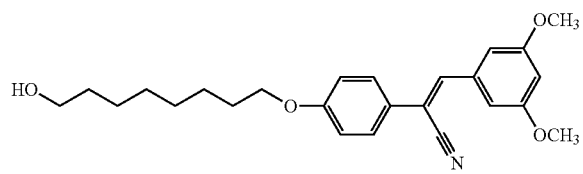 [SMILES: COc1cc(/C=C(\C#N)c2ccc(OCCCCCCCCO)cc2)cc(OC)c1]

(2Z)-3-(3,5-dimethoxyphenyl)-2-{4-[(8-hydroxyoctyl)oxy]phenyl}prop-2-enenitrile is prepared starting from {4-[(8-hydroxyoctyl)oxy]phenyl}acetonitrile and the commercial 3,5-dimethoxybenzaldehyde according the same procedure following for example 1 in 68% yield. This material proves chromatographically homogenous and displays spectral characteristics consistent with its assigned structure.

$^1$H NMR DMSO-$d_6$ 300 MHz: 7.84 (s, 1H), 7.67 (d, 2H), 7.11 (d, 2H), 7.06 (d, 2H), 6.63 (t, 1H), 4.32 (t, 1H), 4.02 (t, 2H), 3.79 (s, 6H), 3.37 (q, 2H), 1.73 (qi, 2H), 1.48-1.22 (m, 10H).

Preparation of 8-{4-[(Z)-1-cyano-2-(3,5-dimethoxyphenyl)ethenyl]phenoxy}octyl 2-methylacrylate

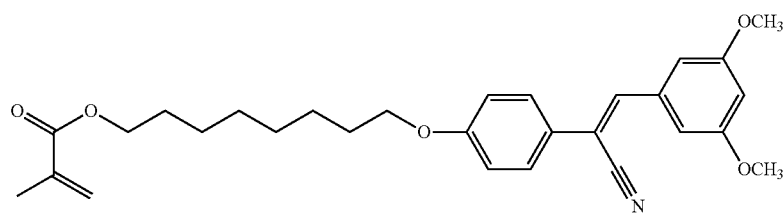 [SMILES: C=C(C)C(=O)OCCCCCCCCOc1ccc(/C(C#N)=C/c2cc(OC)cc(OC)c2)cc1]

8-{4-[(Z)-1-cyano-2-(3,5-dimethoxyphenyl)ethenyl]phenoxy}octyl 2-methylacrylate is prepared starting from (2Z)-3-(3,5-dimethoxyphenyl)-2-{4-[(8-hydroxyoctyl)oxy]phenyl}prop-2-enenitrile according the same procedure following for example 1 in 64% yield. This material proves chromatographically homogenous and displays spectral characteristics consistent with its assigned structure. High-performance liquid chromatography, 97+% of purity with UV-detector at 330 nm.

Preparation of 8-{4-[(Z)-1-cyano-2-(3,5-dimethoxyphenyl)ethenyl]phenoxy}octyl poly-2-methylacrylate

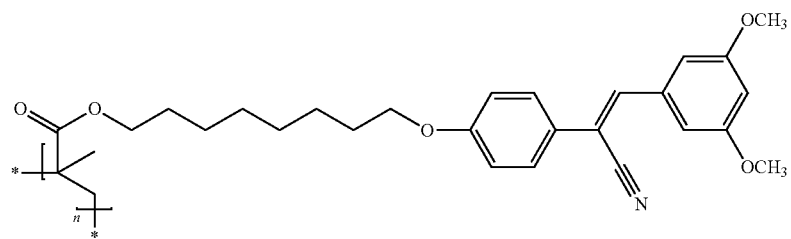

8-{4-[(Z)-1-cyano-2-(3,5-dimethoxyphenyl)ethenyl]phenoxy}octyl poly-2-methylacrylate is prepared starting from 8-{4-[(Z)-1-cyano-2-(3,5-dimethoxyphenyl)ethenyl]phenoxy}octyl 2-methylacrylate according the same procedure following for example 1 in 77% yield. This material displays spectral characteristics consistent with its assigned structure. Size-exclusion chromatography (PS-equivalent), Mn 19,700; Mw 49,300; PDI 2.5. λ max of coated film=338 nm.

$^1$H NMR THF-$d_8$ 300 MHz: 7.58 (d, 2H), 7.47 (s, 1H), 7.06 (d, 2H), 6.91 (d, 2H), 6.50 (d, 1H), 3.94 (m, 4H), 3.76 (s, 6H), 1.82-1.69 (m, 2H), 1.63 (m, 2H), 1.55-1.25 (m, 10H), 1.17-0.84 (m, 3H).

Example 3

Synthesis of 8-{4-[(Z)-2-cyano-2-(3,4-dimethoxyphenyl)ethenyl]phenoxy}octyl poly-2-methylacrylate Preparation of (2Z)-2-(3,4-dimethoxyphenyl)-3-{4-[(8-hydroxyoctyl)oxy]phenyl}prop-2-enenitrile

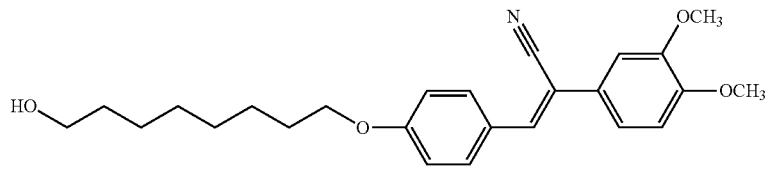 [SMILES: COc1ccc(/C(C#N)=C/c2ccc(OCCCCCCCCO)cc2)cc1OC]

(2Z)-2-(3,4-dimethoxyphenyl)-3-{4-[(8-hydroxyoctyl)oxy]phenyl}prop-2-enenitrile is prepared starting from 4-[(8-hydroxyoctyl)oxy]benzaldehyde and the commercial (3,4-dimethoxyphenyl)acetonitrile according the same procedure following for example 1 in 46% yield. This material proves chromatographically homogenous and displays spectral characteristics consistent with its assigned structure.

$^1$H NMR DMSO-$d_6$ 300 MHz: 7.91 (s, 1H), 7.87 (d, 2H), 7.30 (d, 1H), 7.22 (dd, 1H), 7.08 (d, 2H), 7.05 (m, 1H), 4.32 (t, 1H), 4.04 (t, 2H), 3.85 (s, 3H), 3.80 (s, 3H), 3.35 (q, 2H), 1.73 (qi, 2H), 1.49-1.22 (m, 10H).

Preparation of 8-{4-[(Z)-2-cyano-2-(3,4-dimethoxyphenyl)ethenyl]phenoxy}octyl 2-methylacrylate

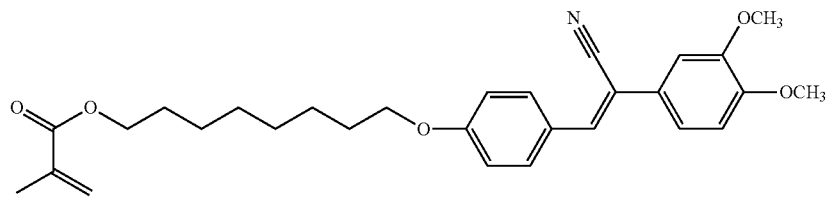 [SMILES: C=C(C)C(=O)OCCCCCCCCOc1ccc(/C=C(\C#N)c2ccc(OC)c(OC)c2)cc1]

8-{4-[(Z)-2-cyano-2-(3,4-dimethoxyphenyl)ethenyl]phenoxy}octyl 2-methylacrylate is prepared starting from (2Z)-2-(3,4-dimethoxyphenyl)-3-{4-[(8-hydroxyoctyl)oxy]phenyl}prop-2-enenitrile according the same procedure following for example 1 in 86% yield. This material proves chromatographically homogenous and displays spectral characteristics consistent with its assigned structure. High-performance liquid chromatography, 98+% of purity with UV-detector at 330 nm.

Preparation of 8-{4-[(Z)-2-cyano-2-(3,4-dimethoxyphenyl)ethenyl]phenoxy}octyl poly-2-methylacrylate

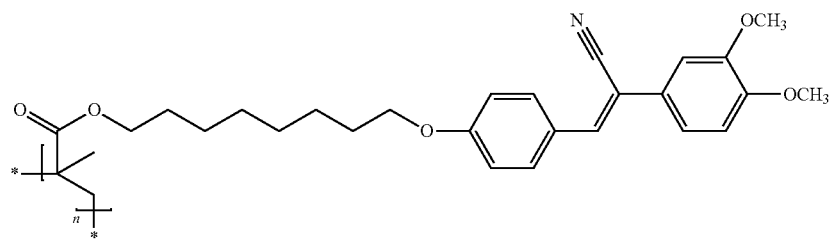

8-{4-[(Z)-2-cyano-2-(3,4-dimethoxyphenyl)ethenyl]phenoxy}octyl poly-2-methylacrylate is prepared starting from 8-{4-[(Z)-2-cyano-2-(3,4-dimethoxyphenyl)ethenyl]phenoxy}octyl 2-methylacrylate according the same procedure following for example 1 in 88% yield. This material displays spectral characteristics consistent with its assigned structure. Size-exclusion chromatography (PS-equivalent), Mn 35,800; Mw 373,000; PDI 10.4. λ max of coated film=356 nm.

$^1$H NMR THF-d$^8$ 300 MHz: 7.87 (m, 2H), 7.51 (m, 1H), 7.21 (m, 2H), 6.95 (m, 3H), 3.98-3.75 (m, 6H), 1.90-1.60 (m, 4H), 1.58-1.36 (m, 10H), 1.19-0.87 (m, 3H).

Example 4

Synthesis of 8-{4-[(Z)-1-cyano-2-(3,4-dimethoxyphenyl)ethenyl]phenoxy}octyl poly-2-methylacrylate Preparation of (2Z)-3-(3,4-dimethoxyphenyl)-2-{4-[(8-hydroxyoctyl)oxy]phenyl}prop-2-enenitrile

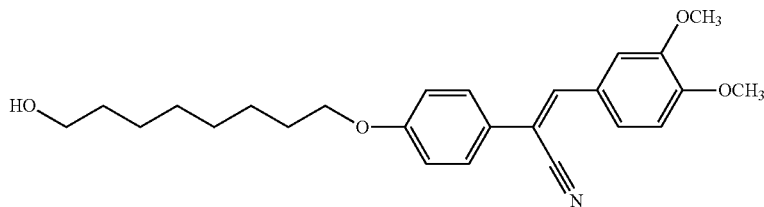 [SMILES: COc1ccc(/C=C(\C#N)c2ccc(OCCCCCCCCO)cc2)cc1OC]

(2Z)-3-(3,4-dimethoxyphenyl)-2-{4-[(8-hydroxyoctyl)oxy]phenyl}prop-2-enenitrile is prepared starting from {4-[(8-hydroxyoctyl)oxy]phenyl}acetonitrile and commercial 3,4-dimethoxybenzaldehyde according the same procedure following for example 1 in 65% yield. This material proves chromatographically homogenous and displays spectral characteristics consistent with its assigned structure.

$^1$H NMR DMSO-d$_6$ 300 MHz: 7.81 (s, 1H), 7.64 (m, 3H), 7.52 (dd, 1H), 7.11 (d, 1H), 7.04 (d, 2H), 4.32 (t, 1H), 4.01 (t, 2H), 3.83 (s, 3H), 3.81 (s, 3H), 3.37 (q, 2H), 1.72 (qi, 2H), 1.49-1.22 (m, 10H).

Preparation of 8-{4-[(Z)-1-cyano-2-(3,4-dimethoxyphenyl)ethenyl]phenoxy}octyl 2-methylacrylate

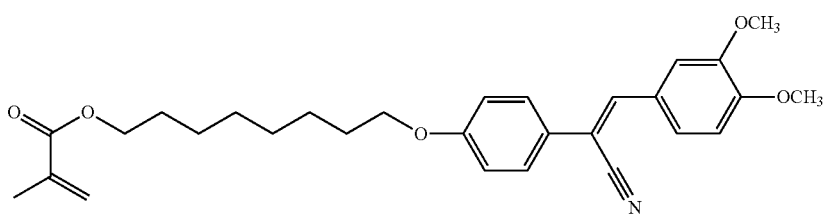 [SMILES: C=C(C)C(=O)OCCCCCCCCOc1ccc(/C(C#N)=C/c2ccc(OC)c(OC)c2)cc1]

8-{4-[(Z)-1-cyano-2-(3,4-dimethoxyphenyl)ethenyl]phenoxy}octyl 2-methylacrylate is prepared starting from (2Z)-3-(3,4-dimethoxyphenyl)-2-{4-[(8-hydroxyoctyl)oxy]phenyl}prop-2-enenitrile according the same procedure following for example 1 in 77% yield. This material proves chromatographically homogenous and displays spectral characteristics consistent with its assigned structure. High-performance liquid chromatography, 95+% of purity with UV-detector at 330 nm.

Preparation of 8-{4-[(Z)-1-cyano-2-(3,4-dimethoxyphenyl)ethenyl]phenoxy}octyl poly-2-methylacrylate

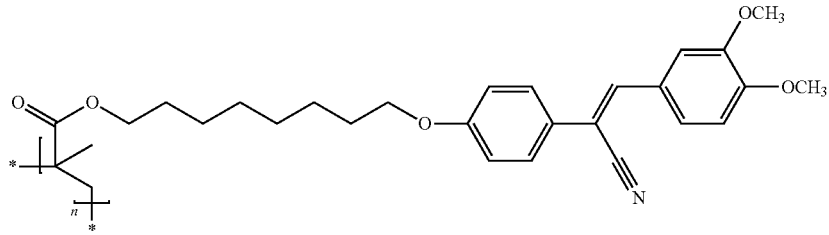

8-{4-[(Z)-1-cyano-2-(3,4-dimethoxyphenyl)ethenyl]phenoxy}octyl poly-2-methylacrylate is prepared starting from 8-{4-[(Z)-1-cyano-2-(3,4-dimethoxyphenyl)ethenyl]phenoxy}octyl 2-methylacrylate according the same procedure following for example 1 in 90% yield. This material displays spectral characteristics consistent with its assigned structure. Size-exclusion chromatography (PS-equivalent), Mn 22,800; Mw 86,000; PDI 3.8. λ max of coated film=354 nm.

$^1$H NMR DMSO-$d_6$ 300 MHz: 7.67 (s, 1H), 7.56 (d, 2H), 7.44 (s, 1H), 7.34 (d, 1H), 6.90 (m, 3H), 3.94 (m, 4H), 3.86-3.75 (m, 6H), 1.86-1.56 (m, 4H), 1.55-1.27 (m, 10H), 1.15-0.85 (m, 3H).

Example 5

Synthesis of 11-{4-[(Z)-2-(1,3-benzodioxol-5-yl)-2-cyanoethenyl]phenoxy}undecyl poly-2-methylacrylate Preparation of 4-[(11-hydroxyundecyl)oxy]benzaldehyde

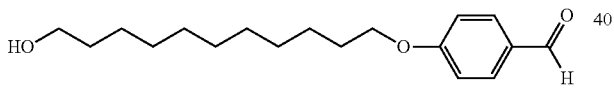

50.0 g (409 mmol) of 4-hydroxybenzaldehyde and 123.0 g (490 mmol) of 11-bromoundecan-1-ol are dissolved in 400 mL of N,N-dimethylformamide. 113.0 g (819 mmol) of potassium carbonate and 7.0 g (42 mmol) of potassium iodide are added and the suspension is heated to 80° C. After 48 h, the excess of potassium carbonate is filtered off and the resulting filtrate is poured to icy water. The aqueous layer is extracted twice with ethyl acetate. Combined organic layers are washed with brine, concentrated to minimum volume and precipitated in cold heptane. The precipitate is filtered off and washed with cold heptanes. 69.4 g of 4-[(11-hydroxyundecyl)oxy]benzaldehyde are obtained as a white solid (57% yield). This material proves chromatographically homogenous and displays spectral characteristics consistent with its assigned structure.

Preparation of (2Z)-2-(1,3-benzodioxol-5-yl)-3-{4-[(11-hydroxyundecyl)oxy]phenyl}prop-2-enenitrile

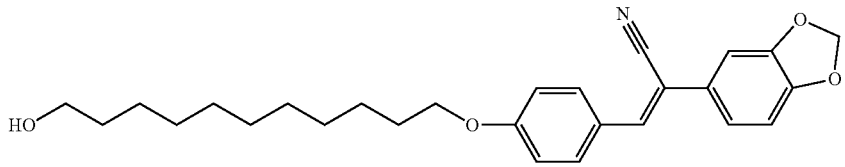 [SMILES: N#C/C(=C\c1ccc(OCCCCCCCCCCCO)cc1)c1ccc2c(c1)OCO2]

(2Z)-2-(1,3-benzodioxol-5-yl)-3-{4-[(11-hydroxyundecyl)oxy]phenyl}prop-2-enenitrile is prepared starting from 4-[(11-hydroxyundecyl)oxy]benzaldehyde and commercial [3,4-(methylenedioxy)phenyl]acetonitrile according the same procedure following for example 1 in 73% yield. This material proves chromatographically homogenous and displays spectral characteristics consistent with its assigned structure.

$^1$H NMR DMSO-$d_6$ 300 MHz: 7.89 (s, 1H), 7.84 (d, 2H), 7.38 (d, 1H), 7.17 (dd, 1H), 7.07 (d, 2H), 7.02 (d, 1H), 6.10 (s, 2H), 4.31 (t, 1H), 4.03 (t, 2H), 3.36 (q, 2H), 1.72 (qi, 2H), 1.49-1.17 (m, 16H).

Preparation of 11-{4-[(Z)-2-(1,3-benzodioxol-5-yl)-2-cyanoethenyl]phenoxy}undecyl 2-methylacrylate

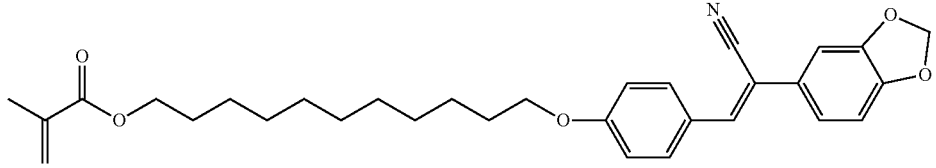 [SMILES: C=C(C)C(=O)OCCCCCCCCCCCOc1ccc(/C=C(\C#N)c2ccc3c(c2)OCO3)cc1]

11-{4-[(Z)-2-(1,3-benzodioxol-5-yl)-2-cyanoethenyl]phenoxy}undecyl 2-methylacrylate is prepared starting from (2Z)-2-(1,3-benzodioxol-5-yl)-3-{4-[(11-hydroxyundecyl)oxy]phenyl}prop-2-enenitrile according the same procedure following for example 1 in 73% yield. This material proves chromatographically homogenous and displays spectral characteristics consistent with its assigned structure. High-performance liquid chromatography, 97+% of purity with UV-detector at 330 nm.

Preparation of 11-{4-[(Z)-2-(1,3-benzodioxol-5-yl)-2-cyanoethenyl]phenoxy}undecyl poly-2-methylacrylate

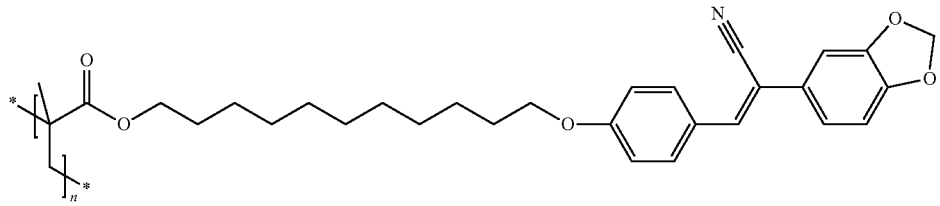

11-{4-[(Z)-2-(1,3-benzodioxol-5-yl)-2-cyanoethenyl]phenoxy}undecyl poly-2-methylacrylate is prepared starting from 11-{4-[(Z)-2-(1,3-benzodioxol-5-yl)-2-cyanoethenyl]phenoxy}undecyl 2-methylacrylate according the same procedure following for example 1 in 51% yield. This material displayed spectral characteristics consistent with its assigned structure. Size-exclusion chromatography (PS-equivalent), Mn 39,400; Mw 343,400; PDI 8.0. λ max of coated film=352 nm.

$^1$H NMR THF-$d_8$ 300 MHz: 7.84 (d, 2H), 7.48 (s, 1H), 7.16 (m, 2H), 6.93 (d, 2H), 6.83 (d, 1H), 5.96 (s, 2H), 3.97 (m, 4H), 1.83-1.68 (m, 2H), 1.63 (m, 2H), 1.56-1.34 (m, 16H), 1.13-0.79 (m, 3H).

Example 6

Synthesis of 11-{4-[(Z)-2-(1,3-benzodioxol-5-yl)-1-cyanoethenyl]phenoxy}undecyl poly-2-methylacrylate Preparation of {4-[(11-hydroxyundecyl)oxy]phenyl}acetonitrile

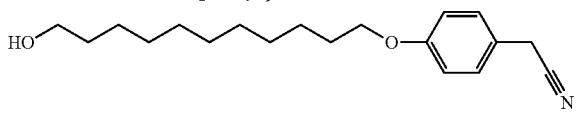

25.0 g (188 mmol) of (4-hydroxyphenyl)acetonitrile and 56.6 g (225 mmol) of 11-bromoundecan-1-ol are dissolved in 250 mL of N,N-dimethylformamide. 51.8 g (375 mmol) of potassium carbonate and 6.0 g (36 mmol) of potassium iodide are added and the suspension was heated to 80° C. After 48 h, the reaction mixture is cooled to room temperature and poured to icy water. The precipitate is filtered off, purified on column chromatography (AcOET/Tol: 2/8) and dried overnight at 40° C. 29.8 g of {4-[(11-hydroxyundecyl)oxy]phenyl}acetonitrile are obtained as a slightly yellow solid (52% yield). This material proves chromatographically homogenous and displays spectral characteristics consistent with its assigned structure.

Preparation of (2Z)-3-(1,3-benzodioxol-5-yl)-2-{4-[(11-hydroxyundecyl)oxy]phenyl}prop-2-enenitrile

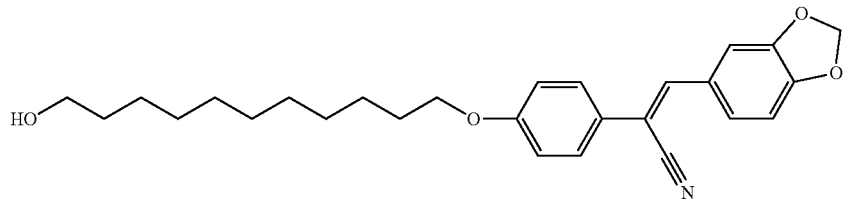 [SMILES: N#C/C(=C\c1ccc2c(c1)OCO2)c1ccc(OCCCCCCCCCCCO)cc1]

(2Z)-3-(1,3-benzodioxol-5-yl)-2-{4-[(11-hydroxyundecyl)oxy]phenyl}prop-2-enenitrile is prepared starting from 4-[(11-hydroxyundecyl)oxy]-benzeneacetonitrile and commercial 3,4-(methylenedioxy)benzaldehyde according the same procedure following for example 1 in 85% yield. This material proves chromatographically homogenous and displays spectral characteristics consistent with its assigned structure.

$^1$H NMR DMSO-$d_6$ 300 MHz: 7.80 (s, 1H), 7.63 (d, 2H), 7.56 (d, 1H), 7.41 (dd, 1H), 7.08 (d, 1H), 7.04 (d, 2H), 6.13 (s, 2H), 4.31 (t, 1H), 4.01 (t, 2H), 3.35 (q, 2H), 1.72 (qi, 2H), 1.40 (m, 4H), 1.26 (m, 12H).

Preparation of 11-{4-[(Z)-2-(1,3-benzodioxol-5-yl)-1-cyanoethenyl]phenoxy}undecyl 2-methylacrylate

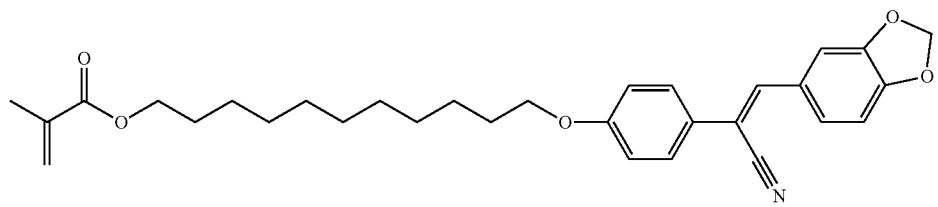 [SMILES: C=C(C)C(=O)OCCCCCCCCCCCOc1ccc(/C(C#N)=C/c2ccc3c(c2)OCO3)cc1]

11-{4-[(Z)-2-(1,3-benzodioxol-5-yl)-1-cyanoethenyl]phenoxy}undecyl 2-methylacrylate is prepared starting from (2Z)-3-(1,3-benzodioxol-5-yl)-2-{4-[(11-hydroxyundecyl)oxy]phenyl}prop-2-enenitrile according the same procedure following for example 1 in 89% yield. This material proves chromatographically homogenous and displays spectral characteristics consistent with its assigned structure. High-performance liquid chromatography, 97+% of purity with UV-detector at 330 nm.

Preparation of 11-{4-[(Z)-2-(1,3-benzodioxol-5-yl)-1-cyanoethenyl]phenoxy}undecyl poly-2-methylacrylate

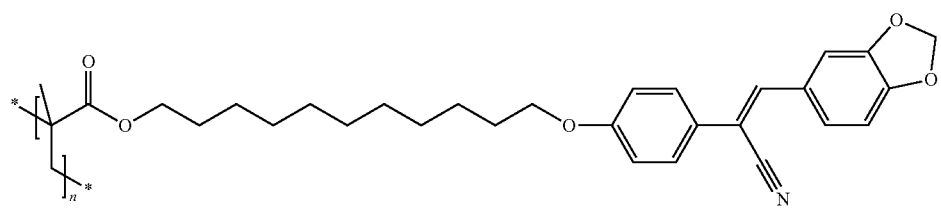

11-{4-[(Z)-2-(1,3-benzodioxol-5-yl)-1-cyanoethenyl]phenoxy}undecyl poly-2-methylacrylate is prepared starting from 11-{4-[(Z)-2-(1,3-benzodioxol-5-yl)-1-cyanoethenyl]phenoxy}undecyl 2-methylacrylate according the same procedure following for example 1 in 79% yield. This material displayed spectral characteristics consistent with its assigned structure. Size-exclusion chromatography (PS-equivalent), Mn 13,600; Mw 156,900; PDI 8.0. λ max of coated film=356 nm.

$^1$H NMR THF-d$_8$ 300 MHz: 7.56 (m, 3H), 7.44 (s, 1H), 7.30 (m, 1H), 6.91 (d, 2H), 6.85 (d, 1H), 6.00 (s, 2H), 3.94 (m, 4H), 1.83-1.68 (m, 2H), 1.62 (m, 2H), 1.53-1.24 (m, 16H), 1.14-0.83 (m, 3H).

Example 7

Synthesis of 11-{4-[(Z)-2-(1,3-benzodioxol-5-yl)-2-cyanoethenyl]-2-methoxyphenoxy}undecyl poly-2-methylacrylate Preparation of 4-[(11-hydroxyundecyl)oxy]-3-methoxybenzaldehyde

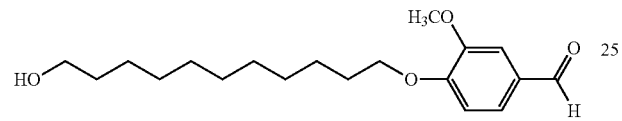

25.9 g (170 mmol) of 4-hydroxy-3-methoxybenzaldehyde and 38.9 g (155 mmol) of 11-bromoundecan-1-ol are dissolved in 200 mL of N,N-dimethylformamide. 23.57 g (170 mmol) of potassium carbonate and 2.47 g (15 mmol) of potassium iodide are added and the suspension is heated to 80° C. After 12 h, the reaction mixture is cooled to room temperature and poured to icy water. The precipitate is filtered off, digested in 500 mL of water and the mixture was neutralized with hydrochloric acid 37%. The precipitate is filtered off, washed with water and dried overnight at 40° C. 48.5 g of 4-[(11-hydroxyundecyl)oxy]-3-methoxybenzaldehyde are obtained as a slightly pink solid (97% yield). This material proves chromatographically homogenous and displays spectral characteristics consistent with its assigned structure.

Preparation of (2Z)-2-(1,3-benzodioxol-5-yl)-3-{4-[(11-hydroxyundecyl)oxy]-3-methoxyphenyl}prop-2-enenitrile

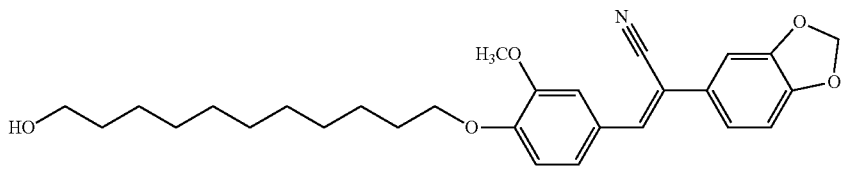

(2Z)-2-(1,3-benzodioxol-5-yl)-3-{4-[(11-hydroxyundecyl)oxy]-3-methoxyphenyl}prop-2-enenitrile is prepared starting from 4-[(11-hydroxyundecyl)oxy]-3-methoxybenzaldehyde and commercial [3,4-(methylenedioxy)phenyl]acetonitrile according the same procedure following for example 1 in 65% yield. This material proves chromatographically homogenous and displays spectral characteristics consistent with its assigned structure.

$^1$H NMR DMSO-d$_6$ 300 MHz: 7.67 (s, 1H), 7.34 (s, 2H), 7.18 (dd, 1H), 7.12 (dd, 1H), 6.92 (d, 1H), 6.88 (d, 1H), 6.02 (s, 2H), 4.32 (t, 1H), 4.09 (t, 2H), 3.95 (s, 3H), 3.66 (t, 2H), 1.89 (qi, 2H), 1.64-1.23 (m, 16H).

Preparation of 11-{4-[(Z)-2-(1,3-benzodioxol-5-yl)-2-cyanoethenyl]-2-methoxyphenoxy}undecyl 2-methylacrylate

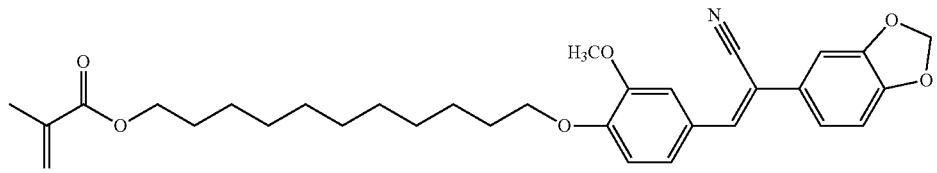 [SMILES: C=C(C)C(=O)OCCCCCCCCCCCOc1ccc(/C=C(\C#N)c2ccc3c(c2)OCO3)cc1OC]

11-{4-[(Z)-2-(1,3-benzodioxol-5-yl)-2-cyanoethenyl]-2-methoxyphenoxy}undecyl 2-methylacrylate is prepared starting from (2Z)-2-(1,3-benzodioxol-5-yl)-3-{4-[(11-hydroxyundecyl)oxy]-3-methoxyphenyl}prop-2-enenitrile according the same procedure following for example 1 in 87% yield. This material proves chromatographically homogenous and displays spectral characteristics consistent with its assigned structure. High-performance liquid chromatography, 97+% of purity with UV-detector at 330 nm.

Preparation of 11-{4-[(Z)-2-(1,3-benzodioxol-5-yl)-2-cyanoethenyl]-2-methoxyphenoxy}undecyl poly-2-methylacrylate

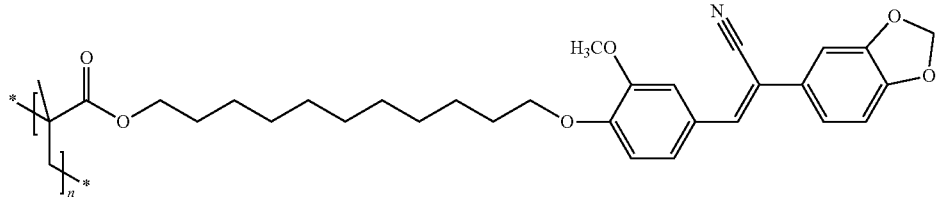

11-{4-[(Z)-2-(1,3-benzodioxol-5-yl)-2-cyanoethenyl]-2-methoxyphenoxy}undecyl poly-2-methylacrylate is prepared starting from 11-{4-[(Z)-2-(1,3-benzodioxol-5-yl)-2-cyanoethenyl]-2-methoxyphenoxy}undecyl 2-methylacrylate according the same procedure following for example 1 in 50% yield. This material displayed spectral characteristics consistent with its assigned structure. Size-exclusion chromatography (PS-equivalent), Mn 83,600; Mw 218,100; PDI 2.6. λ max of coated film=364 nm.

$^1$H NMR THF-$d_8$ 300 MHz: 7.67 (s, 1H), 7.47 (s, 1H), 7.32 (dd, 1H), 7.14 (m, 2H), 6.83 (m, 2H), 5.97 (s, 2H), 3.95 (m, 4H), 3.82 (s, 3H), 1.84-1.57 (m, 4H), 1.56-1.24 (m, 16H), 1.15-0.80 (m, 3H).

Example 8

Synthesis of 11-{4-[(Z)-2-(1,3-benzodioxol-5-yl)-1-cyanoethenyl]-2-methoxyphenoxy}undecyl poly-2-methylacrylate Preparation of {4-[(11-hydroxyundecyl)oxy]-3-methoxyphenyl}acetonitrile

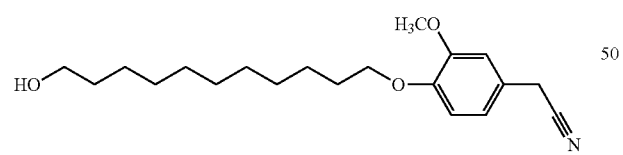

11.0 g (67 mmol) of [4-hydroxy-3-methoxy-phenyl]acetonitrile and 20.4 g (81 mmol) of 11-bromoundecan-1-ol were dissolved in 100 mL of N,N-dimethylformamide. 18.7 g (135 mmol) of potassium carbonate and 2.2.0 g (13 mmol) of potassium iodide were added and the suspension was heated to 80° C. After 48 h, the reaction mixture was cooled to room temperature and poured to icy water. The aqueous layer is extracted twice with ethyl acetate. Combined organic layers are washed with brine and evaporated to dryness. The crude is purified twice on column chromatography (SiO$_2$, Heptane/ethyl acetate: 7/3) and dried overnight at 40° C. 16.6 g of {4-[(11-hydroxyundecyl)oxy]-3-methoxyphenyl}acetonitrile are obtained as a yellow solid (74% yield). This material proves chromatographically homogenous and displays spectral characteristics consistent with its assigned structure.

Preparation of (2Z)-3-(1,3-benzodioxol-5-yl)-2-{4-[(11-hydroxyundecyl)oxy]-3-methoxyphenyl}prop-2-enenitrile

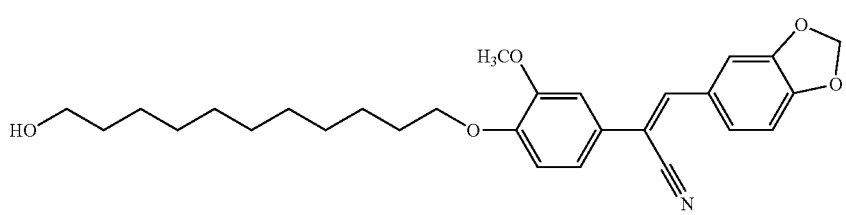 [SMILES: COc1cc(/C(C#N)=C/c2ccc3c(c2)OCO3)ccc1OCCCCCCCCCCCO]

(2Z)-3-(1,3-benzodioxol-5-yl)-2-{4-[(11-hydroxyundecyl)oxy]-3-methoxyphenyl}prop-2-enenitrile is prepared starting from {4-[(11-hydroxyundecyl)oxy]-3-methoxyphenyl}acetonitrile and commercial 3,4-(methylenedioxy)benzaldehyde according the same procedure following for example 1 in 72% yield. This material proves chromatographically homogenous and displays spectral characteristics consistent with its assigned structure.

$^1$H NMR DMSO-$d_6$ 300 MHz: 7.84 (s, 1H), 7.56 (d, 1H), 7.43 (dd, 1H), 7.28 (d, 1H), 7.20 (dd, 1H), 7.07 (m, 2H), 6.13 (s, 2H), 4.31 (t, 1H), 3.98 (t, 2H), 3.85 (s, 3H), 3.37 (q, 2H), 1.74 (qi, 2H), 1.47-1.20 (m, 16H).

Preparation of 11-{4-[(Z)-2-(1,3-benzodioxol-5-yl)-1-cyanoethenyl]-2-methoxyphenoxy}undecyl 2-methylacrylate

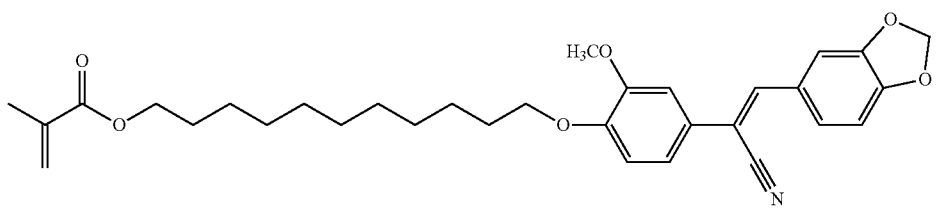 [SMILES: C=C(C)C(=O)OCCCCCCCCCCCOc1ccc(/C(C#N)=C/c2ccc3c(c2)OCO3)cc1OC]

11-{4-[(Z)-2-(1,3-benzodioxol-5-yl)-1-cyanoethenyl]-2-methoxyphenoxy}undecyl 2-methylacrylate is prepared starting from (2Z)-3-(1,3-benzodioxol-5-yl)-2-{4-[(11-hydroxyundecyl)oxy]-3-methoxyphenyl}prop-2-enenitrile according the same procedure following for example 1 in 70% yield. This material proves chromatographically homogenous and displays spectral characteristics consistent with its assigned structure. High-performance liquid chromatography, 97+% of purity with UV-detector at 330 nm.

Preparation of 11-{4-[(Z)-2-(1,3-benzodioxol-5-yl)-1-cyanoethenyl]-2-methoxyphenoxy}undecyl poly-2-methylacrylate

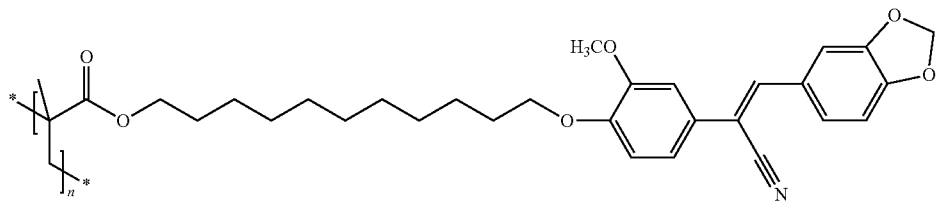

11-{4-[(Z)-2-(1,3-benzodioxol-5-yl)-1-cyanoethenyl]-2-methoxyphenoxy}undecyl poly-2-methylacrylate is prepared starting from 11-{4-[(Z)-2-(1,3-benzodioxol-5-yl)-1-cyanoethenyl]-2-methoxyphenoxy}undecyl 2-methylacrylate according the same procedure following for example 1 in 70% yield. This material displays spectral characteristics consistent with its assigned structure. Size-exclusion chromatography (PS-equivalent), Mn 23,400; Mw 75,400; PDI 3.2. λ max of coated film=364 nm.

$^1$H NMR THF-$d_8$ 300 MHz: 7.55 (d, 1H), 7.48 (s, 1H), 7.29 (d, 1H), 7.16 (m, 2H), 6.85 (m, 2H), 5.99 (s, 2H), 3.94 (m, 4H), 3.82 (s, 3H), 1.84-1.61 (m, 2H), 1.64 (m, 2H), 1.56-1.20 (m, 16H), 1.15-0.79 (m, 3H).

Example 9

Synthesis of 8-{4-[(Z)-1-cyano-2-(2,3-dihydro-1,4-benzodioxin-6-yl)ethenyl]phenoxy}octyl poly-2-methylacrylate Preparation of (2Z)-3-(2,3-dihydro-1,4-benzodioxin-6-yl)-2-{4-[(8-hydroxyoctyl)oxy]phenyl}prop-2-enenitrile

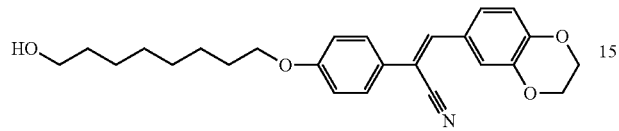

(2Z)-3-(2,3-dihydro-1,4-benzodioxin-6-yl)-2-{4-[(8-hydroxyoctyl)oxy]phenyl}prop-2-enenitrile is prepared starting from {4-[(8-hydroxyoctyl)oxy]phenyl}acetonitrile and commercial 1,4-Benzodioxan-6-carboxaldehyde according the same procedure following for example 1 in 41% yield.

$^1$H NMR DMSO-$d_6$ 300 MHz: 7.76 (s, 1H), 7.63 (d, 2H), 7.52 (d, 1H), 7.43 (dd, 1H), 7.04 (d, 2H), 7.00 (d, 1H), 4.31 (dd, 1H), 4.30 (d, 4H), 4.00 (dd, 2H), 3.37 (dd, 2H), 1.70 (dd, 2H), 1.42 (m, 4H), 1.29 (m, 6H).

Preparation of 8-{4-[(Z)-1-cyano-2-(2,3-dihydro-1,4-benzodioxin-6-yl)ethenyl]phenoxy}octyl 2-methylacrylate

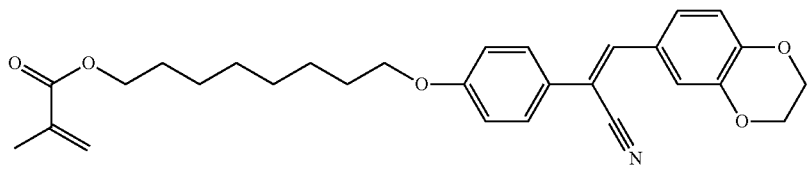 [SMILES: C=C(C)C(=O)OCCCCCCCCOc1ccc(/C(C#N)=C/c2ccc3c(c2)OCCO3)cc1]

8-{4-[(Z)-1-cyano-2-(2,3-dihydro-1,4-benzodioxin-6-yl)ethenyl]phenoxy}octyl 2-methylacrylate is prepared starting from (2Z)-3-(2,3-dihydro-1,4-benzodioxin-6-yl)-2-{4-[(8-hydroxyoctyl)oxy]phenyl}prop-2-enenitrile according the same procedure following for example 1 in 76% yield. This material proves chromatographically homogenous and displays spectral characteristics consistent with its assigned structure. High-performance liquid chromatography, 98+% of purity with UV-detector at 210 nm.

Preparation of 8-{4-[(Z)-1-cyano-2-(2,3-dihydro-1,4-benzodioxin-6-yl)ethenyl]phenoxy}octyl poly-2-methylacrylate

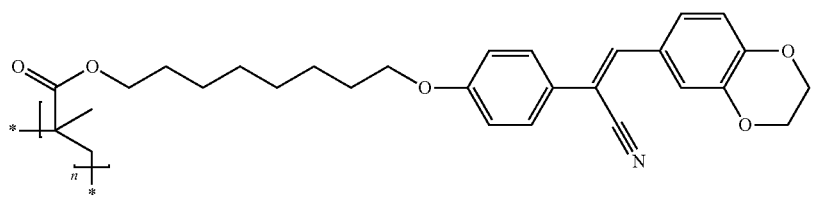

1.86 g (3.9 mmol) of 8-{4-[(Z)-1-cyano-2-(2,3-dihydro-1,4-benzodioxin-6-yl)ethenyl]phenoxy}octyl 2-methylacrylate is dissolved in 9.0 mL of degassed cyclohexanone. The solution is purged with argon (several vacuum-argon cycles) and heated to 60° C. A solution of 16.0 mg (0.10 mmol) of 2,2'-Azobis(2-methylpropionitrile) in 1.5 mL of cyclohexanone is added drop wise. After 15 h at 60° C., the reaction mixture is cooled to room temperature, diluted with 5 mL of tetrahydrofuran, and precipitated in 200 mL of cold methanol. The precipitate is filtered off, washed with methanol and dried overnight at 30° C. 1.74 g of 8-{4-[(Z)-1-cyano-2-(2,3-dihydro-1,4-benzodioxin-6-yl)ethenyl]phenoxy}octyl poly-2-methylacrylate are obtained as a white solid (97% yield). Size-exclusion chromatography (PS-equivalent), Mn 31,300; Mw 70,500; PDI 2.2. λ max of coated film=356 nm.

$^1$H NMR THF-d$_8$ 300 MHz: 7.7-7.3 (m, 5H), 7.0-6.7 (m, 3H), 4.25 (m, 4H), 3.95 (m, 4H), 1.90-1.55 (m, 4H), 1.55-1.20 (m, 10H), 1.2-0.8 (m, 3H).

Example 10

Synthesis of 8-{4-[(Z)-1-cyano-2-(2,3-dihydro-1-benzofuran-6-yl)ethenyl]phenoxy}octyl poly-2-methylacrylate Preparation of (2Z)-3-(2,3-dihydro-1-benzofuran-6-yl)-2-{4-[(8-hydroxyoctyl)oxy]phenyl}prop-2-enenitrile

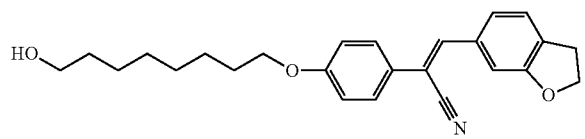 [SMILES: N#C/C(=C\c1ccc2c(c1)OCC2)c1ccc(OCCCCCCCCO)cc1]

((2Z)-3-(2,3-dihydro-1-benzofuran-6-yl)-2-{4-[(8-hydroxyoctyl)oxy]phenyl}prop-2-enenitrile is prepared starting from {4-[(8-hydroxyoctyl)oxy]phenyl}acetonitrile and commercial 2,3-Dihydrobenzofuran-5-carboxaldehyde according the same procedure following for example 1 in 61% yield.

$^1$H NMR DMSO-d$_6$ 300 MHz: 7.88 (s, 1H), 7.78 (s, 1H), 7.68 (dd, 1H), 7.63 (d, 2H), 7.03 (d, 2H), 6.91 (d, 1H), 4.63 (dd, 2H), 4.33 (dd, 1H), 4.00 (dd, 2H), 3.50-3.15 (m, 4H), 1.72 (dd, 2H), 1.41 (m, 4H), 1.29 (m, 6H).

Preparation of 8-{4-[(Z)-1-cyano-2-(2,3-dihydro-1-benzofuran-6-yl)ethenyl]phenoxy}octyl 2-methylacrylate

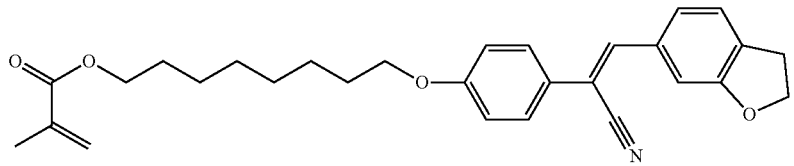 [SMILES: C=C(C)C(=O)OCCCCCCCCOc1ccc(/C(C#N)=C/c2ccc3c(c2)OCC3)cc1]

8-{4-[(Z)-1-cyano-2-(2,3-dihydro-1-benzofuran-6-yl)ethenyl]phenoxy}octyl 2-methylacrylate is prepared starting from ((2Z)-3-(2,3-dihydro-1-benzofuran-6-yl)-2-{4-[(8-hydroxyoctyl)oxy]phenyl}prop-2-enenitrile according the same procedure following for example 1 in 75% yield. This material proves chromatographically homogenous and displays spectral characteristics consistent with its assigned structure. High-performance liquid chromatography, 99+% of purity with UV-detector at 210 nm.

Preparation of 8-{4-[(Z)-1-cyano-2-(2,3-dihydro-1-benzofuran-6-yl)ethenyl]phenoxy}octyl poly-2-methylacrylate

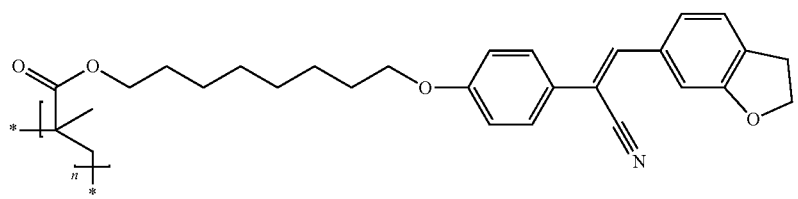

1.80 g (3.9 mmol) of 8-{4-[(Z)-1-cyano-2-(2,3-dihydro-1-benzofuran-6-yl)ethenyl]phenoxy}octyl 2-methylacrylate is dissolved in 9.0 mL of degassed cyclohexanone. The solution is purged with argon (several vacuum-argon cycles) and heated to 60° C. A solution of 16.0 mg (0.10 mmol) of 2,2'-Azobis(2-methylpropionitrile) in 1.5 mL of cyclohexanone is added drop wise. After 15 h at 60° C., the reaction mixture is cooled to room temperature, diluted with 5 mL of tetrahydrofuran, and precipitated in 200 mL of cold methanol. The precipitate is filtered off, washed with methanol and dried overnight at 30° C. 1.74 g of 8-{4-[(Z)-1-cyano-2-(2,3-dihydro-1-benzofuran-6-yl)ethenyl]phenoxy}octyl poly-2-methylacrylate are obtained as a white solid (97% yield). Size-exclusion chromatography (PS-equivalent), Mn 29,200; Mw 70,000; PDI 2.4. λ max of coated film=354 nm.

$^1$H NMR THF-d$_8$ 300 MHz: 7.88 (s, 1H), 7.80-7.55 (m, 2H), 7.45 (s, 1H), 7.00-6.85 (m, 2H), 6.77 (d, 1H), 4.56 (dd, 2H), 3.95 (m, 4H), 3.20 (m, 2H), 1.90-1.55 (m, 4H), 1.55-1.20 (m, 10H), 1.2-0.8 (m, 3H).

Example 11

Synthesis of 11-{4-[(Z)-1-cyano-2-(2,3-dihydro-1,4-benzodioxin-6-yl)ethenyl]-2-methoxyphenoxy}undecyl poly-2-methylacrylate Preparation of (2Z)-3-(2,3-dihydro-1,4-benzodioxin-6-yl)-2-{4-[(11-hydroxyundecyl)oxy]-3-methoxyphenyl}prop-2-enenitrile

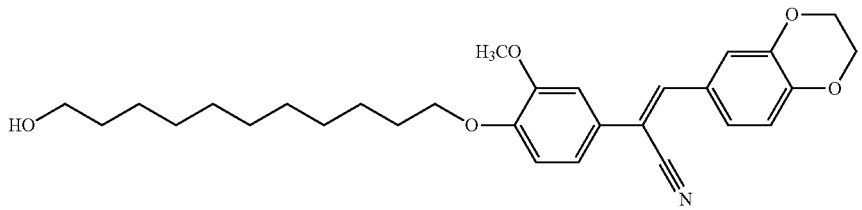 [SMILES: COc1cc(/C(C#N)=C/c2ccc3c(c2)OCCO3)ccc1OCCCCCCCCCCCO]

(2Z)-3-(2,3-dihydro-1,4-benzodioxin-6-yl)-2-{4-[(11-hydroxyundecyl)oxy]-3-methoxyphenyl}prop-2-enenitrile is prepared starting from {4-[(11-hydroxyundecyl)oxy]-3-methoxyphenyl}acetonitrile and commercial 1,4-Benzodioxan-6-carboxaldehyde according the same procedure following for example 1 in 80% yield.

$^1$H NMR DMSO-d$_6$ 300 MHz: 7.81 (s, 1H), 7.53 (d, 1H), 7.44 (dd, 1H), 7.28 (d, 1H), 7.20 (dd, 2H), 7.15-6.95 (m, 2H), 4.31 (dd, 1H), 4.30 (d, 4H), 3.97 (dd, 2H), 3.85 (s, 3H), 3.36 (dd, 2H), 1.70 (dd, 2H), 1.6-1.1 (m, 16H)

Preparation of 11-{4-[(Z)-1-cyano-2-(2,3-dihydro-1,4-benzodioxin-6-yl)ethenyl]-2-methoxyphenoxy}undecyl 2-methylacrylate

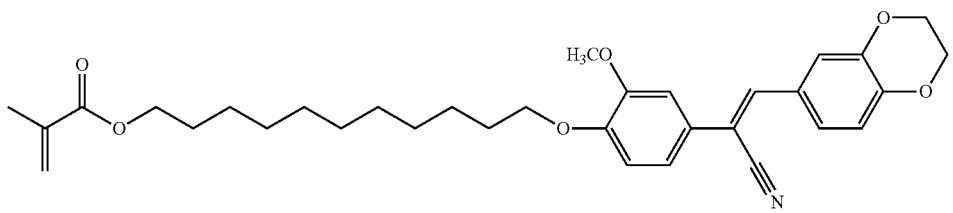 [SMILES: C=C(C)C(=O)OCCCCCCCCCCCOc1ccc(/C(C#N)=C/c2ccc3c(c2)OCCO3)cc1OC]

11-{4-[(Z)-1-cyano-2-(2,3-dihydro-1,4-benzodioxin-6-yl)ethenyl]-2-methoxyphenoxy}undecyl 2-methylacrylate is prepared starting from ((2Z)-3-(2,3-dihydro-1,4-benzodioxin-6-yl)-2-{4-[(11-hydroxyundecyl)oxy]-3-methoxyphenyl}prop-2-enenitrile according the same procedure following for example 1 in 87% yield. This material proves chromatographically homogenous and displays spectral characteristics consistent with its assigned structure. High-performance liquid chromatography, 96+% of purity with UV-detector at 210 nm.

Preparation of 11-{4-[(Z)-1-cyano-2-(2,3-dihydro-1,4-benzodioxin-6-yl)ethenyl]-2-methoxyphenoxy}undecyl poly-2-methylacrylate

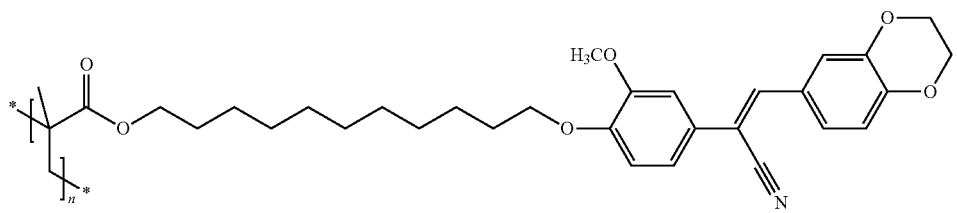

2.14 g (3.9 mmol) of 11-{4-[(Z)-1-cyano-2-(2,3-dihydro-1,4-benzodioxin-6-yl)ethenyl]-2-methoxyphenoxy}undecyl 2-methylacrylate is dissolved in 8.5 mL of degassed cyclohexanone. The solution is purged with argon (several vacuum-argon cycles) and heated to 60° C. A solution of 15.0 mg (0.09 mmol) of 2,2'-Azobis(2-methylpropionitrile) in 1.5 mL of cyclohexanone is added drop wise. After 21 h at 60° C., the reaction mixture is cooled to room temperature, diluted with 5 mL of tetrahydrofuran, and precipitated in 200 mL of cold methanol. The precipitate is filtered off, washed with methanol and dried overnight at 30° C. 2.01 g of 11-{4-[(Z)-1-cyano-2-(2,3-dihydro-1,4-benzodioxin-6-yl)ethenyl]-2-methoxyphenoxy}undecyl 2-methylacrylate are obtained as a white solid (94% yield). Size-exclusion chromatography (PS-equivalent), Mn 31,800; Mw 86,800; PDI 2.7. λ max of coated film=362 nm.

$^1$H NMR THF-$d_8$ 300 MHz: 7.48 (dd, 2H), 7.40 (dd, 1H), 7.22 (s, 1H), 7.20 (d, 1H), 7.00-6.80 (m, 2H), 4.26 (m, 4H), 3.86 (m, 2H), 3.61 (s, 3H), 1.90-1.60 (m, 4H), 1.60-1.20 (m, 16H), 1.15-0.80 (m, 3H).

Example 12

Synthesis of 11-{4-[(Z)-1-cyano-2-(2,3-dihydro-1-benzofuran-6-yl)ethenyl]-2-methoxyphenoxy}undecyl poly-2-methylacrylate Preparation of (2Z)-3-(2,3-dihydro-1-benzofuran-6-yl)-2-{4-[(11-hydroxyundecyl)oxy]-3-methoxyphenyl}prop-2-enenitrile

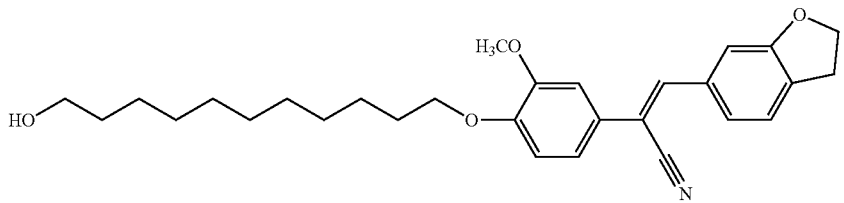 [SMILES: COc1cc(/C(C#N)=C/c2ccc3c(c2)OCC3)ccc1OCCCCCCCCCCCO]

(2Z)-3-(2,3-dihydro-1-benzofuran-6-yl)-2-{4-[(11-hydroxyundecyl)oxy]-3-methoxyphenyl}prop-2-enenitrile is prepared starting from {4-[(11-hydroxyundecyl)oxy]-3-methoxyphenyl}acetonitrile and commercial 2,3-Dihydrobenzofuran-5-carboxaldehyde according the same procedure following for example 1 in 64% yield.

$^1$H NMR DMSO-$d_6$ 300 MHz: 7.90 (s, 1H), 7.84 (s, 1H), 7.71 (dd, 1H), 7.28 (d, 1H), 7.19 (dd, 1H), 7.03 (d, 1H), 6.92 (d, 1H), 4.63 (dd, 2H), 4.32 (dd, 1H), 3.98 (dd, 2H), 3.85 (s, 3H), 3.5-3.1 (m, 4H), 1.70 (dd, 2H), 1.6-1.1 (m, 16H)

Preparation of 11-{4-[(Z)-1-cyano-2-(2,3-dihydro-1-benzofuran-6-yl)ethenyl]-2-methoxyphenoxy}undecyl 2-methylacrylate

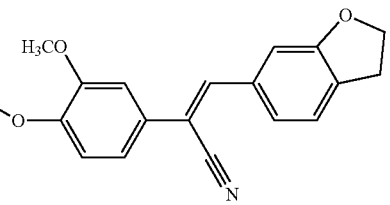

11-{4-[(Z)-1-cyano-2-(2,3-dihydro-1-benzofuran-6-yl)ethenyl]-2-methoxyphenoxy}undecyl 2-methylacrylate is prepared starting from (2Z)-3-(2,3-dihydro-1-benzofuran-6-yl)-2-{4-[(11-hydroxyundecyl)oxy]-3-methoxyphenyl}prop-2-enenitrile according the same procedure following for example 1 in 87% yield. This material proves chromatographically homogenous and displays spectral characteristics consistent with its assigned structure. High-performance liquid chromatography, 97+% of purity with UV-detector at 210 nm.

Preparation of 11-{4-[(Z)-1-cyano-2-(2,3-dihydro-1-benzofuran-6-yl)ethenyl]-2-methoxyphenoxy}undecyl poly-2-methylacrylate

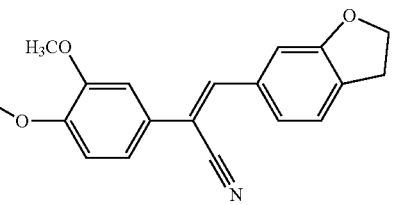

2.01 g (3.9 mmol) of 11-{4-[(Z)-1-cyano-2-(2,3-dihydro-1-benzofuran-6-yl)ethenyl]-2-methoxyphenoxy}undecyl 2-methylacrylate is dissolved in 9.0 mL of degassed cyclohexanone. The solution is purged with argon (several vacuum-argon cycles) and heated to 60° C. A solution of 16.0 mg (0.10 mmol) of 2,2'-Azobis(2-methylpropionitrile) in 1.5 mL of cyclohexanone is added drop wise. After 15 h at 60° C., the reaction mixture is cooled to room temperature, diluted with 5 mL of tetrahydrofuran, and precipitated in 200 mL of cold methanol. The precipitate is filtered off, washed with methanol and dried overnight at 30° C. 1.93 g of 11-{4-[(Z)-1-cyano-2-(2,3-dihydro-1-benzofuran-6-yl)ethenyl]-2-methoxyphenoxy}undecyl poly-2-methylacrylate are obtained as a white solid (93% yield). This material proves chromatographically homogenous and displays spectral characteristics consistent with its assigned structure. Size-exclusion chromatography (PS-equivalent), Mn 33,600; Mw 108,500; PDI 3.2. λ max of coated film=362 nm.

$^1$H NMR THF-$d_8$ 300 MHz: 7.89 (s, 1H), 7.61 (d, 1H), 7.48 (s, 1H), 7.20 (s, 1H), 7.17 (d, 1H), 6.88 (d, 1H), 6.78 (d, 1H), 4.56 (dd, 2H), 3.95 (m, 4H), 3.85 (s, 3H), 3.21 (m, 2H), 1.90-1.60 (m, 4H), 1.60-1.20 (m, 16H), 1.15-0.80 (m, 3H).

Example 13

Synthesis of 11-{4-[(Z)-2-cyano-2-(3,4,5-trimethoxyphenyl)ethenyl]-2-methoxyphenoxy}undecyl poly-2-methylacrylate Preparation of (2Z)-3-{4-[(11-hydroxyundecyl)oxy]-3-methoxyphenyl}-2-(3,4,5-trimethoxyphenyl)prop-2-enenitrile 7.1 g (22 mmol) of 4-[(11-hydroxyundecyl)oxy]-3-methoxybenzaldehyde, 5.0 g (24 mmol) of (3,4,5-trimethoxyphenyl)acetonitrile are dissolved in 50 mL of tert-butyl methyl ether. 0.49 g of potassium tert-butoxide are added under stirring and the mixture is heated to 54° C. After 18 h at 54° C., the reaction mixture is poured on 75 mL icy water under stirring. The pH is adjusted to 7 with 25% HCl. After 1 h stirring, the precipitate is filtered off, washed with water and dried at 40° C. under vacuum. 8.5 g of (2Z)-3-{4-[(11-hydroxyundecyl)oxy]-3-methoxyphenyl}-2-(3,4,5-trimethoxyphenyl)prop-2-enenitrile are obtained as a yellow solid (76% yield). This material proves chromatographically homogenous and displays spectral characteristics consistent with its assigned structure.

Preparation of 11-{4-[(Z)-2-cyano-2-(3,4,5-tri-methoxyphenyl)ethenyl]-2-methoxyphenoxy}undecyl 2-methylacrylate

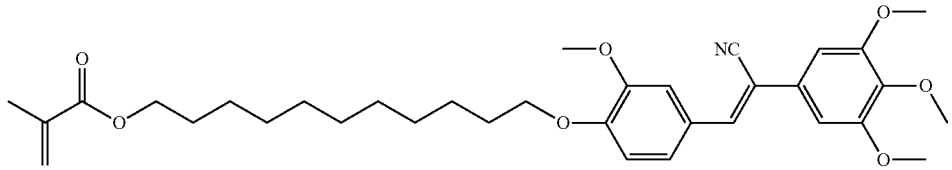 [SMILES: C=C(C)C(=O)OCCCCCCCCCCCOc1ccc(/C=C(\C#N)c2cc(OC)c(OC)c(OC)c2)cc1OC]

11-{4-[(Z)-2-cyano-2-(3,4,5-trimethoxyphenyl)ethenyl]-2-methoxyphenoxy}undecyl 2-methylacrylate is prepared starting from (2Z)-3-{4-[(11-hydroxyundecyl)oxy]-3-methoxyphenyl}-2-(3,4,5-trimethoxyphenyl)prop-2-enenitrile according the same procedure following for example 1 in 51% yield.

$^1$H NMR CDCl$_3$ 300 MHz: 7.67 (d, 1H), 7.38 (s, 1H), 7.36 (d, 1H), 6.95 (d, 1H), 6.86 (s, 2H), 6.11 (s, 1H), 5.56 (m, 1H), 4.15 (t, 2H), 4.09 (t, 2H), 3.97 (s, 3H), 3.95 (s, 6H), 3.90 (s, 3H), 1.96 (s, 3H), 1.90 (m, 2H), 1.70 (m, 2H), 1.49-1.23 (m, 14H)

Preparation of 11-{4-[(Z)-2-cyano-2-(3,4,5-tri-methoxyphenyl)ethenyl]-2-methoxyphenoxy}undecyl poly-2-methylacrylate

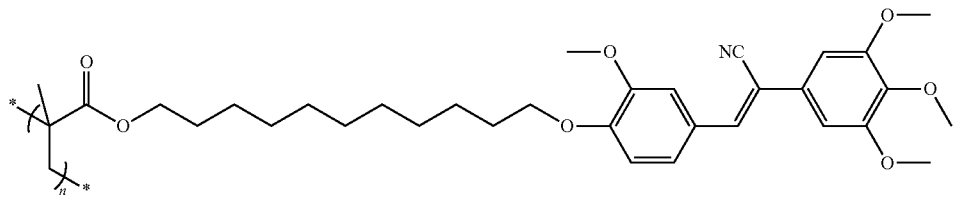

11-{4-[(Z)-2-cyano-2-(3,4,5-trimethoxyphenyl)ethenyl]-2-methoxyphenoxy}undecyl poly-2-methylacrylate is prepared starting from 11-{4-[(Z)-2-cyano-2-(3,4,5-trimethoxyphenyl)ethenyl]-2-methoxyphenoxy}undecyl 2-methylacrylate according the same procedure following for example 1 in 91% yield. The material displays spectral characteristic consistent with its assigned structure. Size-exclusion chromatography (PS-equivalent), Mn 36,300; Mw 155,400; PDI 4.3.

Example 14

Synthesis of 8-{4-[(Z)-2-(1,3-benzodioxol-5-yl)-2-cyanoethenyl]-2-methoxyphenoxy}octyl poly-2-methylacrylate Preparation of 4-[(8-hydroxyoctyl)oxy]-3-methoxybenzaldehyde

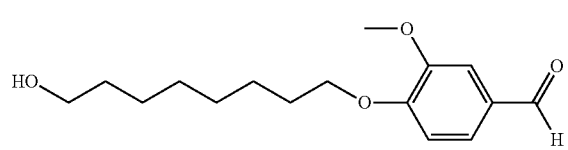 [SMILES: COc1cc(C=O)ccc1OCCCCCCCCO]

4-[(8-hydroxyoctyl)oxy]-3-methoxybenzaldehyde is prepared starting from 4-hydroxy-3-methoxybanzaldehyde and 8-chlorooctan-1-ol according the same procedure following for example 7 in 97% yield. This material proves chromatographically homogenous and displays spectral characteristics consistent with its assigned structure.

Preparation of (2Z)-2-(1,3-benzodioxol-5-yl)-3-{4-[(8-hydroxyoctyl)oxy]-3-methoxyphenyl}prop-2-enenitrile

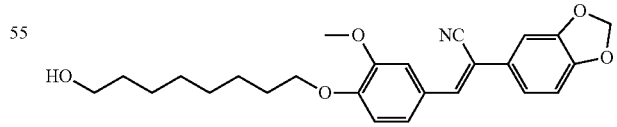

(2Z)-2-(1,3-benzodioxol-5-yl)-3-{4-[(8-hydroxyoctyl)oxy]-3-methoxyphenyl}prop-2-enenitrile is prepared starting from 4-[(8-hydroxyoctyl)oxy]-3-methoxybenzaldehyde and 1,3-benzodioxol-5-ylacetonitrile according the same procedure following for example 10 in 99% yield. This material proves chromatographically homogenous and displays spectral characteristics consistent with its assigned structure.

Preparation of 8-{4-[(Z)-2-(1,3-benzodioxol-5-yl)-2-cyanoethenyl]-2-methoxyphenoxy}octyl 2-methylacrylate

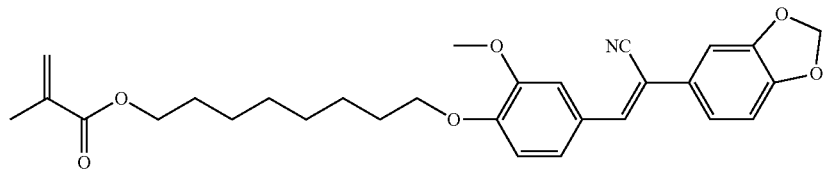 [SMILES: C=C(C)C(=O)OCCCCCCCCOc1ccc(/C=C(\C#N)c2ccc3c(c2)OCO3)cc1OC]

8-{4-[(Z)-2-(1,3-benzodioxol-5-yl)-2-cyanoethenyl]-2-methoxyphenoxy}octyl 2-methylacrylate is prepared starting from (2Z)-2-(1,3-benzodioxol-5-yl)-3-{4-[(8-hydroxyoctyl)oxy]-3-methoxyphenyl}prop-2-enenitrile according the same procedure following for example 1 in 81% yield.

$^1$H NMR CDCl$_3$ 300 MHz: 7.67 (d, 1H), 7.34-7.28 (m, 2H), 7.20-7.13 (m, 2H), 6.93-6.86 (m, 2H), 6.12 (s, 1H), 6.04 (s, 2H), 5.57 (m, 1H), 4.16 (t, 2H), 4.09 (t, 2H), 3.96 (s, 3H), 1.96 (s, 3H), 1.90 (m, 2H), 1.70 (m, 2H), 1.49-1.23 (m, 8H)

Preparation of 8-{4-[(Z)-2-(1,3-benzodioxol-5-yl)-2-cyanoethenyl]-2-methoxyphenoxy}octyl poly-2-methylacrylate

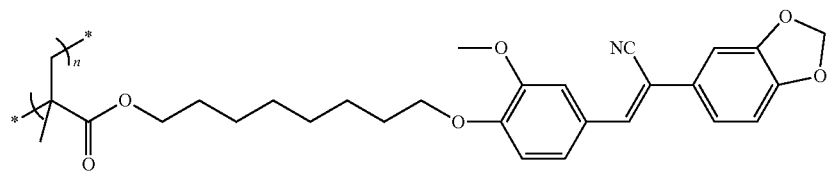

8-{4-[(Z)-2-(1,3-benzodioxol-5-yl)-2-cyanoethenyl]-2-methoxyphenoxy}octyl poly-2-methylacrylate is prepared starting from 8-{4-[(Z)-2-(1,3-benzodioxol-5-yl)-2-cyanoethenyl]-2-methoxyphenoxy}octyl 2-methylacrylate according the same procedure following for example 1 in 94% yield. The material displays spectral characteristic consistent with its assigned structure. Size-exclusion chromatography (PS-equivalent), Mn 29,400; Mw 130,900; PDI 4.5.

Example 15

Synthesis of 6-{4-[(Z)-2-(1,3-benzodioxol-5-yl)-2-cyanoethenyl]-2-methoxyphenoxy}hexyl poly-2-methylacrylate Preparation of 4-[(6-hydroxyhexyl)oxy]-3-methoxybenzaldehyde

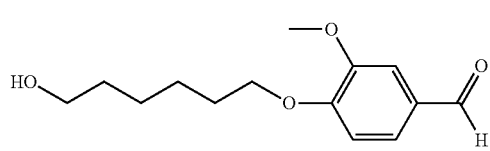 [SMILES: COc1cc(C=O)ccc1OCCCCCCO]

4-[(6-hydroxyhexyl)oxy]-3-methoxybenzaldehyde is prepared starting from 4-hydroxy-3-methoxybenzaldehyde and 6-chlorohexan-1-ol according the same procedure following for example 7 in 88% yield. This material proves chromatographically homogenous and displays spectral characteristics consistent with its assigned structure.

Preparation of (2Z)-2-(1,3-benzodioxol-5-yl)-3-{4-[(6-hydroxyhexyl)oxy]-3-methoxyphenyl}prop-2-enenitrile

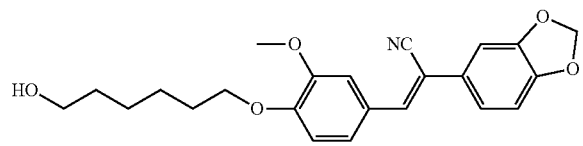 [SMILES: COc1cc(/C=C(\C#N)c2ccc3c(c2)OCO3)ccc1OCCCCCCO]

(2Z)-2-(1,3-benzodioxol-5-yl)-3-{4-[(6-hydroxyhexyl)oxy]-3-methoxyphenyl}prop-2-enenitrile is prepared from 4-[(6-hydroxyhexyl)oxy]-3-methoxybenzaldehyde and 1,3-benzodioxol-5-ylacetonitrile according the same procedure following for example 10 in 85% yield. This material proves chromatographically homogenous and displays spectral characteristics consistent with its assigned structure.

89

Preparation of 6-{4-[(Z)-2-(1,3-benzodioxol-5-yl)-2-cyanoethenyl]-2-methoxyphenoxy}hexyl 2-methylacrylate

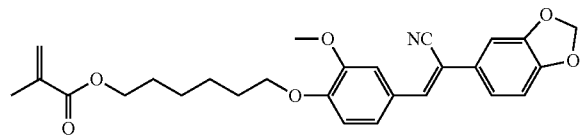 [SMILES: C=C(C)C(=O)OCCCCCCOc1ccc(/C=C(\C#N)c2ccc3c(c2)OCO3)cc1OC]

6-{4-[(Z)-2-(1,3-benzodioxol-5-yl)-2-cyanoethenyl]-2-methoxyphenoxy}hexyl 2-methylacrylate is prepared starting from (2Z)-2-(1,3-benzodioxol-5-yl)-3-{4-[(6-hydroxyhexyl)oxy]-3-methoxyphenyl}prop-2-enenitrile according the same procedure following for example 1 in 83% yield.

$^{1}$H NMR CDCl$_{3}$ 300 MHz: 7.67 (d, 1H), 7.34-7.28 (m, 2H), 7.20-7.13 (m, 2H), 6.93-6.86 (m, 2H), 6.11 (s, 1H), 6.03 (s, 2H), 5.57 (m, 1H), 4.17 (t, 2H), 4.09 (t, 2H), 3.96 (s, 3H), 1.96 (s, 3H), 1.90 (m, 2H), 1.70 (m, 2H), 1.49-1.23 (m, 4H)

Preparation of 6-{4-[(Z)-2-(1,3-benzodioxol-5-yl)-2-cyanoethenyl]-2-methoxyphenoxy}hexyl poly-2-methylacrylate

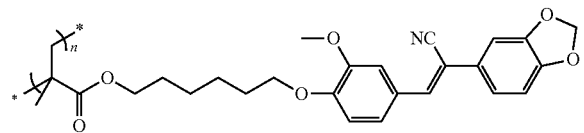

6-{4-[(Z)-2-(1,3-benzodioxol-5-yl)-2-cyanoethenyl]-2-methoxyphenoxy}hexyl poly-2-methylacrylate is prepared starting from 6-{4-[(Z)-2-(1,3-benzodioxol-5-yl)-2-cyanoethenyl]-2-methoxyphenoxy}hexyl 2-methylacrylate according the same procedure following for example 1 in 93% yield. The material displays spectral characteristic consistent with its assigned structure. Size-exclusion chromatography (PS-equivalent), 26,600; Mw 96,200; PDI 1.9.

Example 16

Synthesis of 6-{4-[(Z)-2-cyano-2-(3,4-dimethoxyphenyl)ethenyl]-2-ethoxyphenoxy}hexyl poly-2-methylacrylate Preparation of 3-ethoxy-4-[(6-hydroxyhexyl)oxy]benzaldehyde

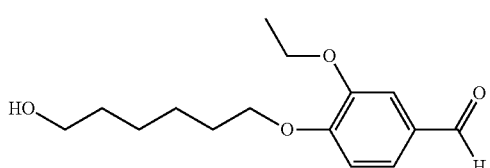

90

3-ethoxy-4-[(6-hydroxyhexyl)oxy]benzaldehyde is prepared starting from 3-ethoxy-4-hydroxybenzaldehyde and 6-chlorohexan-1-ol according the same procedure following for example 7 in 84% yield. This material proves chromatographically homogenous and displays spectral characteristics consistent with its assigned structure.

Preparation of (2Z)-2-(3,4-dimethoxyphenyl)-3-{3-ethoxy-4-[(6-hydroxyhexyl)oxy]phenyl}prop-2-enenitrile

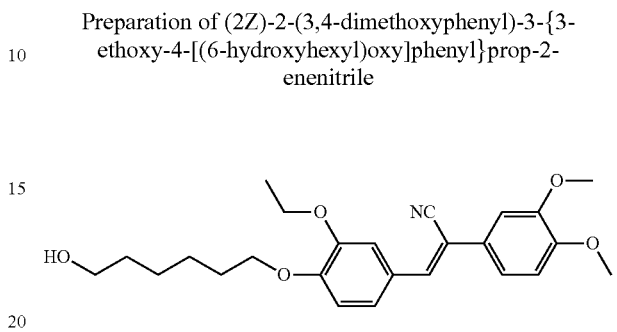

(2Z)-2-(3,4-dimethoxyphenyl)-3-{3-ethoxy-4-[(6-hydroxyhexyl)oxy]phenyl}prop-2-enenitrile is prepared starting from 3-ethoxy-4-[(6-hydroxyhexyl)oxy]benzaldehyde and (3,4-dimethoxyphenyl)acetonitrile according the same procedure following for example 10 in 96% yield. This material proves chromatographically homogenous and displays spectral characteristics consistent with its assigned structure.

Preparation of 6-{4-[(Z)-2-cyano-2-(3,4-dimethoxyphenyl)ethenyl]-2-ethoxyphenoxy}hexyl 2-methylacrylate

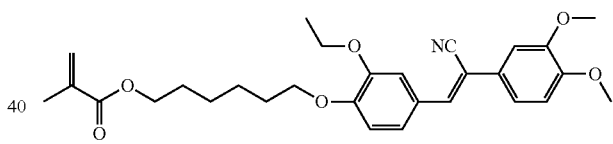

6-{4-[(Z)-2-cyano-2-(3,4-dimethoxyphenyl)ethenyl]-2-ethoxyphenoxy}hexyl 2-methylacrylate is prepared starting from (2Z)-2-(3,4-dimethoxyphenyl)-3-{3-ethoxy-4-[(6-hydroxyhexyl)oxy]phenyl}prop-2-enenitrile according the same procedure following for example 1 in 40% yield.

$^{1}$H NMR CDCl$_{3}$ 300 MHz: 7.66 (d, 1H), 7.35-7.24 (m, 3H), 7.13 (d, 1H), 6.94 (d, 2H), 6.11 (s, 1H), 5.57 (m, 1H), 4.20 (m, 4H), 4.09 (t, 2H), 3.97 (s, 3H), 3.94 (s, 3H), 1.96 (s, 3H), 1.90 (m, 2H), 1.70 (m, 2H), 1.59-1.27 (m, 7H)

Preparation of 6-{4-[(Z)-2-cyano-2-(3,4-dimethoxyphenyl)ethenyl]-2-ethoxyphenoxy}hexyl poly-2-methylacrylate

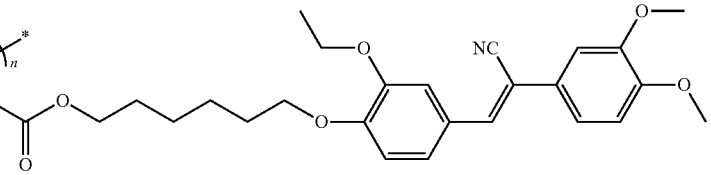

6-{4-[(Z)-2-cyano-2-(3,4-dimethoxyphenyl)ethenyl]-2-ethoxyphenoxy}hexyl poly-2-methylacrylate is prepared starting 6-{4-[(Z)-2-cyano-2-(3,4-dimethoxyphenyl)ethenyl]-2-ethoxyphenoxy}hexyl 2-methylacrylate according the same procedure following for example 1 in 91% yield. The material displays spectral characteristic consistent with its assigned structure. Size-exclusion chromatography (PS-equivalent), Mn 33,100; Mw 124,500; PDI 3.8.

Example 17

Synthesis of 6-{4-[(Z)-2-(1,3-benzodioxol-5-yl)-2-cyanoethenyl]-2-ethoxyphenoxy}hexyl poly-2-methylacrylate Preparation of (2Z)-2-(1,3-benzodioxol-5-yl)-3-{3-ethoxy-4-[(6-hydroxyhexyl)oxy]phenyl}prop-2-enenitrile

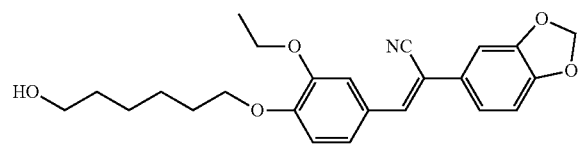

(2Z)-2-(1,3-benzodioxol-5-yl)-3-{3-ethoxy-4-[(6-hydroxyhexyl)oxy]phenyl}prop-2-enenitrile is prepared starting from 3-ethoxy-4-[(6-hydroxyhexyl)oxy]benzaldehyde and 1,3-benzodioxol-5-ylacetonitrile according the same procedure following for example 10 in 96% yield. This material proves chromatographically homogenous and displays spectral characteristics consistent with its assigned structure.

Preparation of 6-{4-[(Z)-2-(1,3-benzodioxol-5-yl)-2-cyanoethenyl]-2-ethoxyphenoxy}hexyl 2-methylacrylate

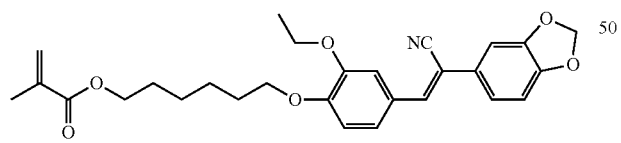

6-{4-[(Z)-2-(1,3-benzodioxol-5-yl)-2-cyanoethenyl]-2-ethoxyphenoxy}hexyl 2-methylacrylate is prepared starting from (2Z)-2-(1,3-benzodioxol-5-yl)-3-{3-ethoxy-4-[(6-hydroxyhexyl)oxy]phenyl}prop-2-enenitrile according the same procedure following for example 1 in 60% yield.

$^1$H NMR CDCl$_3$ 300 MHz: 7.66 (d, 1H), 7.32-7.28 (m, 2H), 7.19-7.12 (m, 2H), 6.93 (m, 2H), 6.11 (s, 1H), 6.04 (s, 2H), 5.57 (m, 1H), 4.22 (m, 4H), 4.08 (t, 2H), 1.96 (s, 3H), 1.90 (m, 2H), 1.70 (m, 2H), 1.59-1.27 (m, 7H)

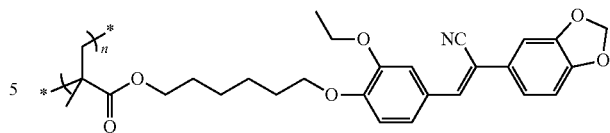

6-{4-[(Z)-2-(1,3-benzodioxol-5-yl)-2-cyanoethenyl]-2-ethoxyphenoxy}hexyl poly-2-methylacrylate is prepared starting from 6-{4-[(Z)-2-(1,3-benzodioxol-5-yl)-2-cyanoethenyl]-2-ethoxyphenoxy}hexyl 2-methylacrylate according the same procedure following for example 1 in 90% yield. The material displays spectral characteristic consistent with its assigned structure. Size-exclusion chromatography (PS-equivalent), Mn 34,000; Mw 200,800; PDI 5.9.

Example 18

Synthesis of 6-{4-[(Z)-2-cyano-2-(3,4-dimethoxyphenyl)ethenyl]-2,6-dimethoxyphenoxy}hexyl poly-2-methylacrylate Preparation of 4-[(6-hydroxyhexyl)oxy]-3,5-dimethoxybenzaldehyde

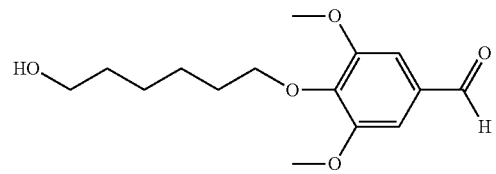 [SMILES: COc1cc(C=O)cc(OC)c1OCCCCCCO]

4-[(6-hydroxyhexyl)oxy]-3,5-dimethoxybenzaldehyde is starting from 4-hydroxy-3,5-dimethoxybenzaldehyde and 6-chlorohexan-1-ol according the same procedure following for example 7 in 47% yield. This material proves chromatographically homogenous and displays spectral characteristics consistent with its assigned structure.

Preparation of (2Z)-2-(3,4-dimethoxyphenyl)-3-{4-[(6-hydroxyhexyl)oxy]-3,5-dimethoxyphenyl}prop-2-enenitrile

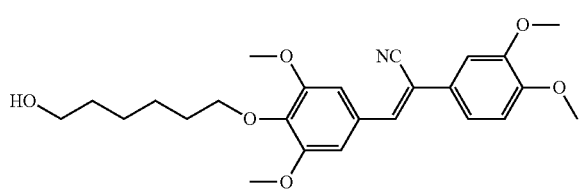 [SMILES: COc1ccc(/C(C#N)=C/c2cc(OC)c(OCCCCCCO)c(OC)c2)cc1OC]

(2Z)-2-(3,4-dimethoxyphenyl)-3-{4-[(6-hydroxyhexyl)oxy]-3,5-dimethoxyphenyl}prop-2-enenitrile is prepared starting from 4-[(6-hydroxyhexyl)oxy]-3,5-dimethoxybenzaldehyde and (3,4-dimethoxyphenyl)acetonitrile according the same procedure following for example 10 in 97% yield.

This material proves chromatographically homogenous and displays spectral characteristics consistent with its assigned structure.

Preparation of 6-{4-[(Z)-2-cyano-2-(3,4-dimethoxyphenyl)ethenyl]-2,6-dimethoxyphenoxy}hexyl 2-methylacrylate

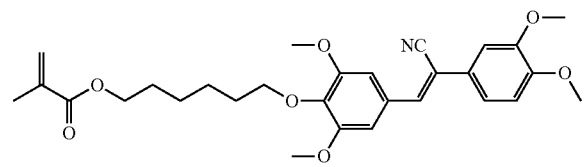 [SMILES: C=C(C)C(=O)OCCCCCCOc1c(OC)cc(/C=C(\C#N)c2ccc(OC)c(OC)c2)cc1OC]

6-{4-[(Z)-2-cyano-2-(3,4-dimethoxyphenyl)ethenyl]-2,6-dimethoxyphenoxy}hexyl 2-methylacrylate is prepared starting from (2Z)-2-(3,4-dimethoxyphenyl)-3-{4-[(6-hydroxyhexyl)oxy]-3,5-dimethoxyphenyl}prop-2-enenitrile according the same procedure following for example 1 in 40% yield.

$^1$H NMR CDCl$_3$ 300 MHz: 7.35 (s, 1H), 7.25 (m, 1H), 7.15 (m, 3H), 6.95 (d, 1H), 6.11 (s, 1H), 5.56 (m, 1H), 4.17 (t, 2H), 4.06 (t, 2H), 3.98 (s, 3H), 3.95 (s, 3H), 3.92 (s, 6H), 1.96 (s, 3H), 1.90 (m, 4H), 1.70 (m, 4H)

Preparation of 6-{4-[(Z)-2-cyano-2-(3,4-dimethoxyphenyl)ethenyl]-2,6-dimethoxyphenoxy}hexyl 2-methylacrylate

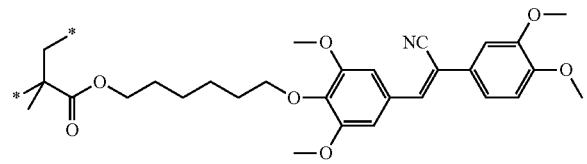 [SMILES: *CC(*)(C)C(=O)OCCCCCCOc1c(OC)cc(/C=C(\C#N)c2ccc(OC)c(OC)c2)cc1OC]

6-{4-[(Z)-2-cyano-2-(3,4-dimethoxyphenyl)ethenyl]-2,6-dimethoxyphenoxy}hexyl poly-2-methylacrylate is prepared starting 6-{4-[(Z)-2-cyano-2-(3,4-dimethoxyphenyl)ethenyl]-2,6-dimethoxyphenoxy}hexyl 2-methylacrylate according the same procedure following for example 1 in 86% yield. The material displays spectral characteristic consistent with its assigned structure. Size-exclusion chromatography (PS-equivalent), Mn 31,300; Mw 234,700; PDI 7.5.

Example 19

Synthesis of 6-{4-[(Z)-2-(1,3-benzodioxol-5-yl)-2-cyanoethenyl]-2,6-dimethoxyphenoxy}hexyl poly-2-methylacrylate Preparation of (2Z)-2-(1,3-benzodioxol-5-yl)-3-{4-[(6-hydroxyhexyl)oxy]-3,5-dimethoxyphenyl}prop-2-enenitrile

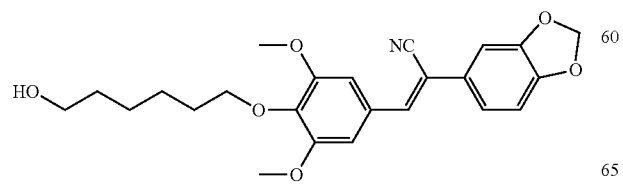

(2Z)-2-(1,3-benzodioxol-5-yl)-3-{4-[(6-hydroxyhexyl)oxy]-3,5-dimethoxyphenyl}prop-2-enenitrile is prepared starting from 4-[(6-hydroxyhexyl)oxy]-3,5-dimethoxybenzaldehyde and 1,3-benzodioxol-5-ylacetonitrile according the same procedure following for example 10 in 95% yield. This material proves chromatographically homogenous and displays spectral characteristics consistent with its assigned structure.

Preparation of 6-{4-[(Z)-2-(1,3-benzodioxol-5-yl)-2-cyanoethenyl]-2,6-dimethoxyphenoxy}hexyl 2-methylacrylate

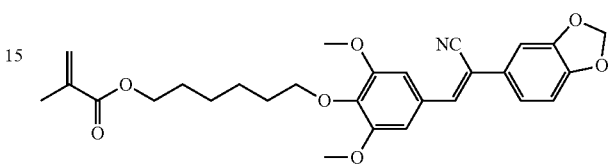

6-{4-[(Z)-2-(1,3-benzodioxol-5-yl)-2-cyanoethenyl]-2,6-dimethoxyphenoxy}hexyl 2-methylacrylate is prepared starting from (2Z)-2-(1,3-benzodioxol-5-yl)-3-{4-[(6-hydroxyhexyl)oxy]-3,5-dimethoxyphenyl}prop-2-enenitrile according the same procedure following for example 1 in 43% yield.

$^1$H NMR CDCl$_3$ 300 MHz: 7.32 (m, 2H), 7.28 (m, 3H), 6.89 (d, 1H), 6.11 (s, 1H), 6.04 (s, 2H), 5.57 (m, 1H), 4.17 (t, 2H), 4.06 (t, 2H), 3.92 (s, 6H), 1.96 (s, 3H), 1.90 (m, 4H), 1.70 (m, 4H)

Preparation of 6-{4-[(Z)-2-(1,3-benzodioxol-5-yl)-2-cyanoethenyl]-2,6-dimethoxyphenoxy}hexyl poly-2-methylacrylate

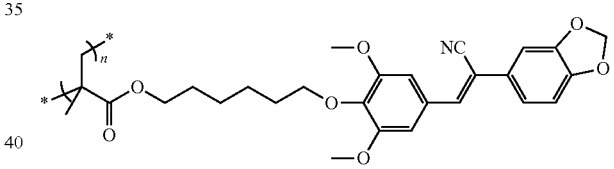

6-{4-[(Z)-2-(1,3-benzodioxol-5-yl)-2-cyanoethenyl]-2,6-dimethoxyphenoxy}hexyl poly-2-methylacrylate is prepared starting from 6-{4-[(Z)-2-(1,3-benzodioxol-5-yl)-2-cyanoethenyl]-2,6-dimethoxyphenoxy}hexyl 2-methylacrylate according the same procedure following for example 1 in 85% yield. The material displays spectral characteristic consistent with its assigned structure. Size-exclusion chromatography (PS-equivalent), Mn 29,700; Mw 159,100; PDI 5.4.

Example 20

Synthesis of 11-{4-[(Z)-2-cyano-2-(3,4-diethoxyphenyl)ethenyl]-2-methoxyphenoxy}undecyl poly-2-methylacrylate Preparation of 2-(3,4-diethoxyphenyl)-acetonitrile

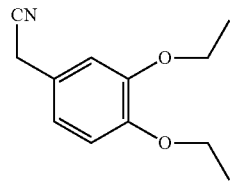

15.44 g (140 mmol) of bromoethane and 8.95 g (59 mmol) of 2-(3,4-Dihydroxyphenyl)-acetonitrile are dissolved in 120 mL of N,N-dimethylformamide. 19.39 g (140 mmol) of potassium carbonate and 0.97 g (6 mmol) of potassium iodide are added to the mixture and the resulting suspension is heated to 80° C. After 6 h the reaction mixture is cooled down to at least 30° C. Pour the suspension on 200 mL of icy water, stir for ca. 20 min and filter off. Digest the solid in 120 mL of water, neutralize with hydrochloric acid 25% stir for 30 min. The precipitate is filtered off, washed with water and dried under vacuum at r40° C. 4.72 g of 2-(3,4-diethoxyphenyl)-acetonitrile are obtained as a white powder (39.3% yield). This material proves chromatographically homogenous and displays spectral characteristics consistent with its assigned structure.

Preparation of
4-[(11-hydroxyundecyl)oxy]-3-methoxybenzaldehyde

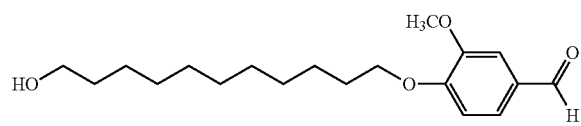 [SMILES: COc1cc(C=O)ccc1OCCCCCCCCCCCO]

25.9 g (170 mmol) of 4-hydroxy-3-methoxybenzaldehyde and 38.9 g (155 mmol) of 11-bromoundecan-1-ol are dissolved in 200 mL of N,N-dimethylformamide. 23.57 g (170 mmol) of potassium carbonate and 2.47 g (15 mmol) of potassium iodide are added and the suspension is heated to 80° C. After 12 h, the reaction mixture is cooled to room temperature and poured to icy water. The precipitate is filtered off, digested in 500 mL of water and the mixture was neutralized with hydrochloric acid 37%. The precipitate is filtered off, washed with water and dried overnight at 40° C. 48.5 g of 4-[(11-hydroxyundecyl)oxy]-3-methoxybenzaldehyde are obtained as a slightly pink solid (97% yield). This material proves chromatographically homogenous and displays spectral characteristics consistent with its assigned structure.

Preparation of (2Z)-2-(3,5-diethoxy)-3-{4-[(11-hydroxyundecyl)oxy]-3-methoxyphenyl}prop-2-enenitrile

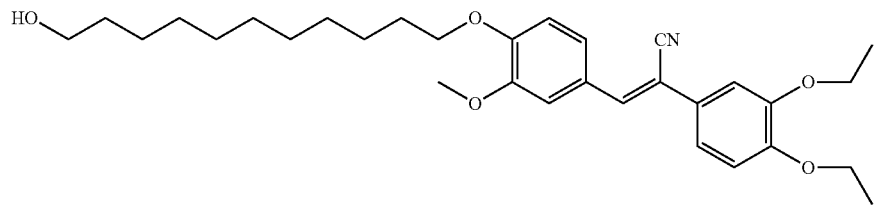 [SMILES: CCOc1ccc(/C(C#N)=C/c2ccc(OCCCCCCCCCCCO)c(OC)c2)cc1OCC]

(2Z)-2-(3,5-diethoxy)-3-{4-[(11-hydroxyundecyl)oxy]-3-methoxyphenyl}prop-2-enenitrile is prepared with 0.87 g (3 mmol) of 4-[(11-hydroxyundecyl)oxy]-3-methoxybenzaldehyde and 0.62 g (3 mmol) 2-(3,4-diethoxyphenyl)-acetonitrile (synthesized according to the procedure following the example 10). The chemicals are dissolved in 10 mL of tert-butyl methyl ether. 0.06 g (0.5 mmol) of Potassium-tert-butoxide is added and the suspension is heated to 54° C. Keep the reaction under heating and stirring for 17.5 h. Pour the remains on 75 mL of icy water under stirring, add hydrochloric acid to neutralize the solution, stir for 1 h, filter off, wash with water and dry at 40° C. under vacuum until stable mass. 0.9 g of (2Z)-2-(3,5-diethoxy)-3-{4-[(11-hydroxyundecyl)oxy]-3-methoxyphenyl}prop-2-enenitrile are obtained as orange powder (66% yield).

Preparation of 11-{4-[(Z)-2-cyano-2-(3,4-dimethoxyphenyl)ethenyl]-2-methoxyphenoxy}undecyl 2-methylacrylate

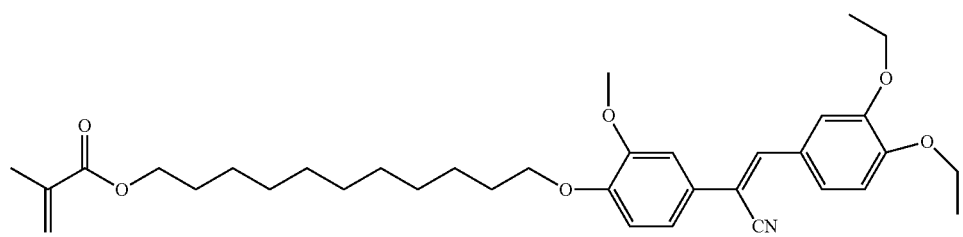 [SMILES: C=C(C)C(=O)OCCCCCCCCCCCOc1ccc(/C(C#N)=C/c2ccc(OCC)c(OCC)c2)cc1OC]

0.9 g (1.7 mmol) (2Z)-2-(3,5-diethoxy)-3-{4-[(11-hydroxyundecyl)oxy]-3-methoxyphenyl}prop-2-enenitrile, 0.34 g (3.4 mmol) of triethylamine and 0.02 g (0.2 mmol) of 4-dimethylaminopyridine are dissolved in 2.5 mL of tetrahydrofuran. Purge the system with argon, cool the solution to 0° C. and add 0.3 g (1.9 mmol) of methacrylic anhydride dropwise at maximum 5° C. under stirring. Stir the mixture for further 1 h and remove the cooling. Keep the reaction for 18 h at room temperature. Transfer the solution slowly under stirring to ca. 5 mL of icy water, stir the resulting suspension for 1 h. Filter off the sticky material, wash with water (pH neutral) and dry the solid at 40° C. under vacuum overnight. Add the solid to 3 mL of methanol and 5 mg (0.02 mmol) of 2,6-di-tert-butyl-4-methylphenol. Heat the suspension to 72° C. until complete dissolution. Remove the heating and allow the solid to recrystallize overnight under stirring. Filter off the suspension and dry the solid under vacuum at room temperature. 0.40 g of 11-{4-[(Z)-2-cyano-2-(3,4-dimethoxy)ethenyl]-2-methoxyphenoxy}undecyl-2-methylacrylate is obtained (39% yield).

$^1$H NMR CDCl$_3$ 300 MHz: 7.66 (d, 1H), 7.36 (m, 2H), 7.23 (m, 2H), 6.94 (d, 2H), 6.11 (s, 1H), 5.56 (m, 1H), 4.19 (m, 8H), 3.96 (s, 3H), 1.96 (s, 3H), 1.90 (m, 2H), 1.70 (m, 2H), 1.66-1.31 (m, 20H)

Preparation of 11-{4-[(Z)-2-cyano-2-(3,4-dimethoxyphenyl)ethenyl]-2-methoxyphenoxy}undecyl poly-2-methylacrylate 11-{4-[(Z)-2-cyano-2-(3,4-dimethoxyphenyl)ethenyl]-2-methoxyphenoxy}undecyl poly-2-methylacrylate is prepared starting from 11-{4-[(Z)-2-cyano-2-(3,4-dimethoxyphenyl)ethenyl]-2-methoxyphenoxy}undecyl 2-methylacrylate according the same procedure following for example 1 in 94.5% yield. This material displays spectral characteristics consistent with its assigned structure. Size-exclusion chromatography (PS-equivalent), Mn 37,907; Mw 133,526; PDI 3.5.

Example 21

Synthesis of 11-{4-[(Z)-2-cyano-2-(3,4-diisopropoxyphenyl)ethenyl]-2-methoxyphenoxy}undecyl poly-2-methylacrylate Preparation of 2-(3,4-(diisopropoxy phenyl)-acetonitrile

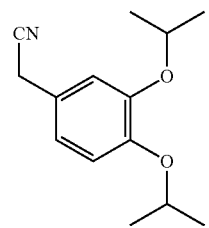

15.47 g (125 mmol) of 2-bromopropane and 7.94 g (52 mmol) of 2-(3,4-Dihydroxyphenyl)-acetonitrile are dissolved in 100 mL of N,N-dimethylformamide. 17.21 g (125 mmol) of potassium carbonate and 0.86 g (5 mmol) of potassium iodide are added to the mixture and the resulting suspension is heated to 80° C. After 4 h the reaction mixture is cooled down to at least 30° C. Pour the suspension on 200 mL of icy water, stir for ca. 20 min and filter off. Digest the solid in 120 mL of water, neutralize with hydrochloric acid 25% stir for 30 min. The precipitate is filtered off, washed with water and dried under vacuum at 40° C. 3.31 g of 2-(3,4-(diisopropoxy phenyl)-acetonitrile are obtained. This material proves chromatographically homogenous and displays spectral characteristics consistent with its assigned structure.

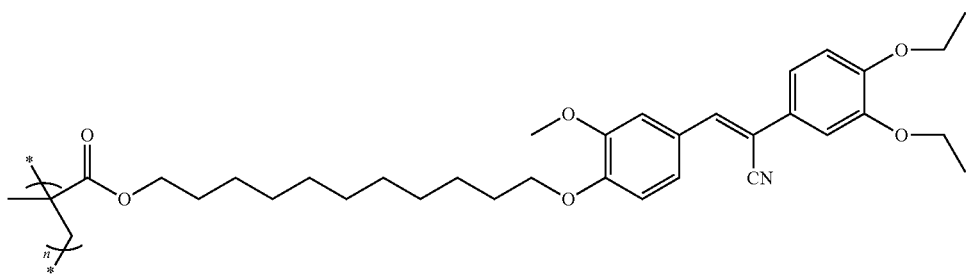

Preparation of 4-[(11-hydroxyundecyl)oxy]-3-methoxybenzaldehyde

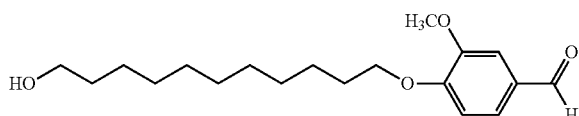

25.9 g (170 mmol) of 4-hydroxy-3-methoxybenzaldehyde and 38.9 g (155 mmol) of 11-bromoundecan-1-ol are dissolved in 200 mL of N,N-dimethylformamide. 23.57 g (170 mmol) of potassium carbonate and 2.47 g (15 mmol) of potassium iodide are added and the suspension is heated to 80° C. After 12 h, the reaction mixture is cooled to room temperature and poured to icy water. The precipitate is filtered off, digested in 500 mL of water and the mixture was neutralized with hydrochloric acid 37%. The precipitate is filtered off, washed with water and dried overnight at 40° C. 48.5 g of 4-[(11-hydroxyundecyl)oxy]-3-methoxybenzaldehyde are obtained as a slightly pink solid (97% yield). This material proves chromatographically homogenous and displays spectral characteristics consistent with its assigned structure.

Preparation of (2Z)-2-(3,4-diisopropoxy phenyl)-3-{4-[(11-hydroxyundecyl)oxy]-3-methoxyphenyl}prop-2-enenitrile

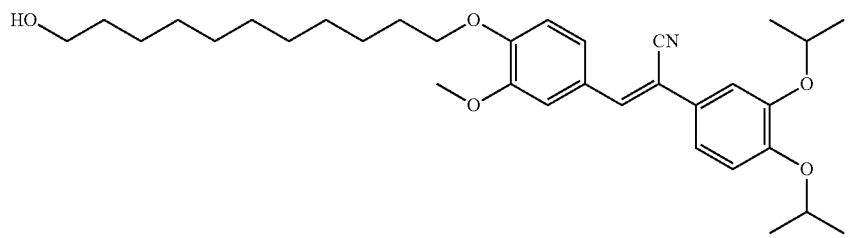 [SMILES: COc1cc(/C=C(\C#N)c2ccc(OC(C)C)c(OC(C)C)c2)ccc1OCCCCCCCCCCCO]

(2Z)-2-(3,4-diisopropoxy phenyl)-3-{4-[(11-hydroxyundecyl)oxy]-3-methoxyphenyl}prop-2-enenitrile is prepared with 4.16 g (13 mmol) of 2-(3,4-(diisopropoxy phenyl)-acetonitrile (according the procedure following the example 11) and 3.31 g (14 mmol) 4-[(11-hydroxyundecyl)oxy]-3-methoxybenzaldehyde (synthesized according to the procedure following the example 9). The chemicals are dissolved in 25 mL of tert-butyl methyl ether. 0.29 g (2.6 mmol) of potassium-tert-butoxide is added and the suspension is heated to 54° C. Keep the reaction under heating and stirring. Past ca. 19 h of reaction extra 0.15 g (1.3 mmol) of potassium-tert-butoxide is added to the reaction and stirred totalizing 43 h. Pour the remains on 40 mL of icy water under stirring, add hydrochloric acid to neutralize the solution, stir for 1 h. The product does not precipitate, results in a dark yellow-brownish oily fluid wish was dried at room temperature under vacuum until stable mass giving 7.35 g (96.3% yield).

Preparation of 11-{4-[(Z)-2-cyano-2-(3,4-diisopropoxyphenyl)ethenyl]-2-methoxyphenoxy}undecyl-2-methylacrylate

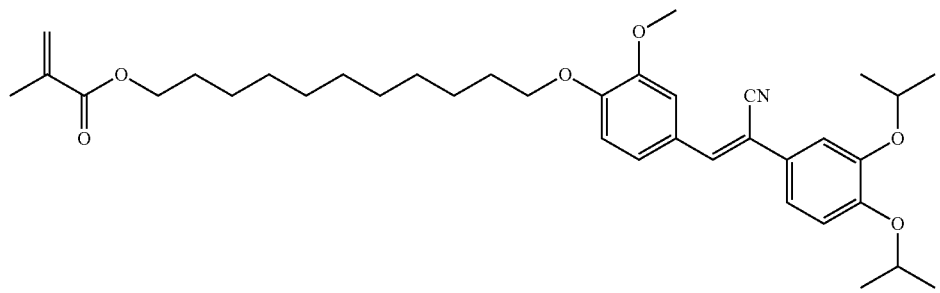 [SMILES: C=C(C)C(=O)OCCCCCCCCCCCOc1ccc(/C=C(\C#N)c2ccc(OC(C)C)c(OC(C)C)c2)cc1OC]

11-{4-[(Z)-2-cyano-2-(3,4-diisopropoxyphenyl)ethenyl]-2-methoxyphenoxy}undecyl-2-methylacrylate is prepared starting from 7.35 g (13 mmol) of (2Z)-2-(3,5-diisopropoxyphenyl)-3-{4-[(11-hydroxyundecyl)oxy]-3-methoxyphenyl}prop-2-enenitrile, 2.66 g (26 mmol) of triethylamine and 0.16 g (1.3 mmol) of 4-dimethylaminopyridine are dissolved in 20 mL of tetrahydrofuran. Purge the system with argon, cool the solution to 0° C. and add 2.23 g (14 mmol) of methacrylic anhydride dropwise at maximum 5° C. under stirring. Stir the mixture for further 1 h and remove the cooling. Keep the reaction for 19.5 h at room temperature. Transfer the solution slowly under stirring to ca. 30 mL of icy water, stir the resulting suspension for 1 h. Filter off the suspension, wash with water (pH neutral) and dry the solid at 40° C. under vacuum overnight. Add the solid to 40 mL of methanol and 5 mg (0.02 mmol) of 2,6-di-tert-butyl-4-methylphenol. Heat the suspension to 72° C. until complete dissolution. Remove the heating and allow the solid to recrystallize overnight under stirring. Filter off the suspension and dry the solid under vacuum at room temperature. 3.50 g of 11-{4-[(Z)-2-cyano-2-(3,5-diisopropoxy)ethenyl]-2-methoxyphenoxy}undecyl-2-methylacrylate is obtained (42.3% yield).

$^1$H NMR CDCl$_3$ 300 MHz: 7.67 (d, 1H), 7.33 (m, 2H), 7.22 (m, 2H), 6.94 (m, 2H), 6.11 (s, 1H), 5.57 (m, 1H), 4.55 (m, 2H), 4.15 (t, 2H), 4.09 (t, 2H), 3.96 (s, 3H), 1.96 (s, 3H), 1.90 (m, 2H), 1.70 (m, 2H), 1.66-1.31 (m, 26H)

Preparation of 11-{4-[(Z)-2-cyano-2-(3,4-diisopropoxyphenyl)ethenyl]-2-methoxyphenoxy}undecyl poly-2-methylacrylate

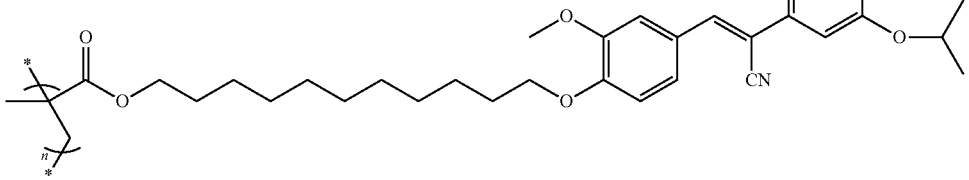

11-{4-[(Z)-2-cyano-2-(3,4-diisopropoxyphenyl)ethenyl]-2-methoxyphenoxy}undecyl poly-2-methylacrylate is prepared starting from 11-{4-[(Z)-2-cyano-2-(3,4-diisopropoxyphenyl)ethenyl]-2-methoxyphenoxy}undecyl 2-methylacrylate according the same procedure following for example 1 in 98.3% yield. This material displays spectral characteristics consistent with its assigned structure. Size-exclusion chromatography (PS-equivalent), Mn 45,807; Mw 218,282; PDI 4.8.

Example 22

Synthesis of Polyamic Acid PAA-1

Preparation of 11-{4-[(Z)-2-(1,3-benzodioxol-5-yl)-2-cyanoethenyl]-2-methoxyphenoxy}undecyl 3,5-dinitrobenzoate

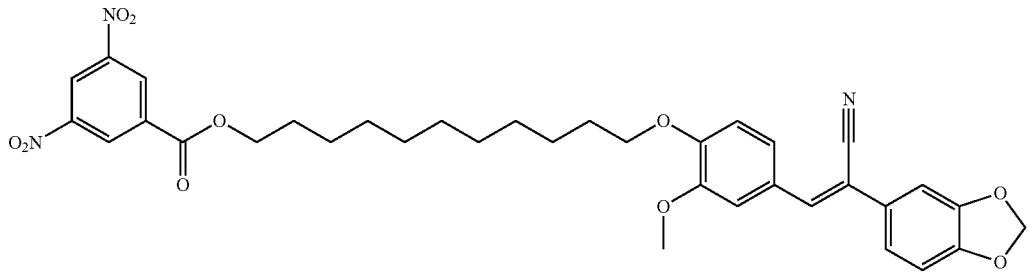 [SMILES: COc1cc(/C=C(\C#N)c2ccc3c(c2)OCO3)ccc1OCCCCCCCCCCCOC(=O)c1cc([N+](=O)[O-])cc([N+](=O)[O-])c1]

1.98 g (8.6 mmol) of 3,5-dinitrobenzoyl chloride are dissolved in 16 mL of toluene and 3 drops of DMF were incorporated. 4 g (8.6 mmol) of (2Z)-2-(1,3-benzodioxol-5-yl)-3-{4-[(11-hydroxyundecyl)oxy]-3-methoxyphenyl}prop-2-enenitrile from example 7, 0.052 g (0.4 mmol) of 4-dimethylaminopyridine and 1.03 mL (13 mmol) of pyridine are added. The mixture is stirred at room temperature for 96 hours. The solution is then heated up to 60° C. and 6.5 ml of MeOH are added. The suspension is stirred at room temperature for 1 hour and at 0° C. for 1 hour. The precipitate is filtered off. Recrystallisation of the residue in acetonitrile yielded 5.1 g (90%) of pure 11-{4-[(Z)-2-(1,3-benzodioxol-5-yl)-2-cyanoethenyl]-2-methoxyphenoxy}undecyl 3,5-dinitrobenzoate as yellowish powder.

Preparation of 11-{4-[(Z)-2-(1,3-benzodioxol-5-yl)-2-cyanoethenyl]-2-methoxyphenoxy}undecyl 3,5-diaminobenzoate

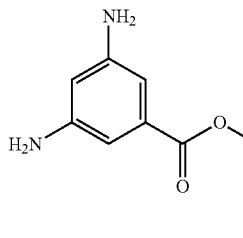
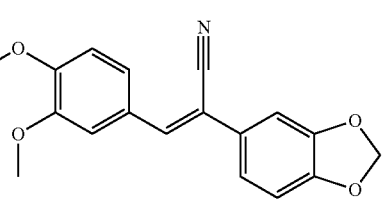

5 g (7.6 mmol) of 11-{4-[(Z)-2-(1,3-benzodioxol-5-yl)-2-cyanoethenyl]-2-methoxyphenoxy}undecyl 3,5-dinitrobenzoate are dissolved in a mixture of 84 ml of DMF and 9 ml of water. 15.7 g (58 mmol) of ferric chloride hexahydrate are added. 6.31 g (97 mmol) of zinc powder are added portionwise within 30 min. The mixture is allowed to react for 2 hours. The reaction mixture is then partitioned between ethyl acetate and water and filtered. The organic phase is washed repeatedly with water, dried over sodium sulfate, filtered and concentrated by rotary evaporation. Filtration of the residue on silica gel using toluene:ethyl acetate(1:3) as eluant and yielded 2.8 g (61%) of 11-{4-[(Z)-2-(1,3-benzodioxol-5-yl)-2-cyanoethenyl]-2-methoxyphenoxy}undecyl 3,5-diaminobenzoate as a white powder.

$^1$H NMR (300 MHz) in DMSO-$d_6$: 7.83 (s, 1H), 7.63 (d, 1H), 7.50 (dd, 1H), 7.37 (d, 1H), 7.18 (dd, 1H), 7.09 (d, 1H), 7.02 (d, 1H), 6.42 (d, 2H), 6.10 (s, 2H), 6.02 (t, 1H), 4.98 (s, 4H), 4.15 (t, 2H), 4.03 (t, 2H), 3.81 (s, 3H), 1.66 (m, 4H), 1.28 (m, 14H)

Preparation of Polyamic Acid PAA-1 from 11-{4-[(Z)-2-(1,3-benzodioxol-5-yl)-2-cyanoethenyl]-2-methoxyphenoxy}undecyl 3,5-diaminobenzoate

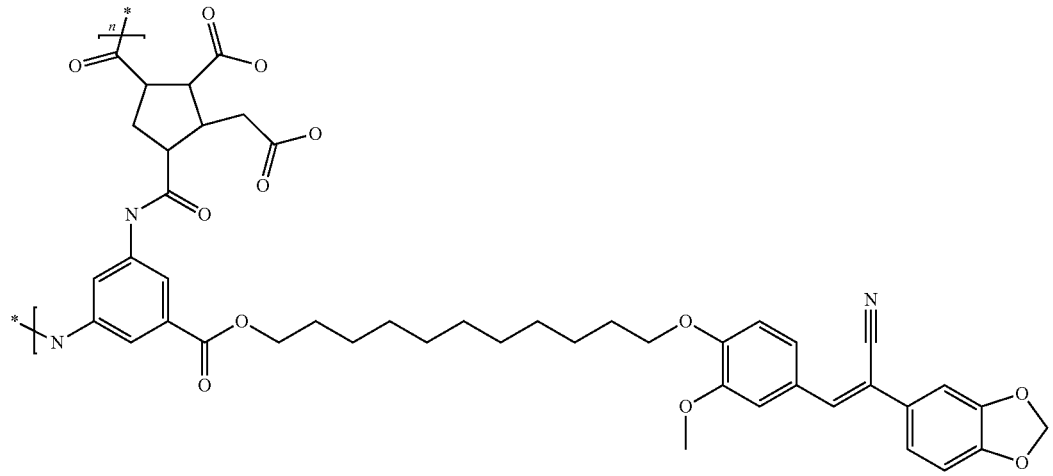

0.560 g (2.5 mmol) of 2,3,5-tricarboxycyclopentylacetic-1,2:3,4-dianhydride is added to a solution of 1.5 g (2.5 mmol) of 11-{4-[(Z)-2-(1,3-benzodioxol-5-yl)-2-cyanoethenyl]-2-methoxyphenoxy}undecyl 3,5-diaminobenzoate in 4.8 g of NMP. Stirring is then carried out at 0° C. for 2 hours. The mixture is subsequently allowed to react for 48 hours at room temperature. The polymer mixture is diluted with 30 g of NMP, precipitated into 300 mL of water to yield, after drying at 40° C. under vacuum, 2.02 g of polyamic acid PAA-1 in the form of a white powder.

$^1$H NMR (300 MHz) in DMSO-$d_6$: 12.6 (s, 2H), 10.03 (m, 2H), 8.01 (m, 1H), 7.94 (m, 1H), 7.77 (m, 1H), 7.60 (m., 1H), 7.45 (m, 1H), 7.32 (m, 1H), 7.15 (m, 1H), 7.05 (m, 3H), 6.01 (m, 2H), 4.22 (m, 2H), 3.97 (m, 2H), 3.78 (m, 3H), 3.30-2.80 (m, 3H), 2.40 (m, 4H), 1.70 (m, 5H), 1.35 (m, 14H)

Example 23

Synthesis of poly 6-{4-[(1E)-3-methoxy-3-oxoprop-1-enyl]phenoxy}hexyl 2-methylacrylate-co-11-{4-[(Z)-2-(1,3-benzodioxol-5-yl)-2-cyanoethenyl]-2-methoxyphenoxy}undecyl 2-methylacrylate (Monomer Weight Ratio 99:1)

Preparation of 6-{4-[(1E)-3-methoxy-3-oxoprop-1-enyl]phenoxy}hexyl 2-methylacrylate

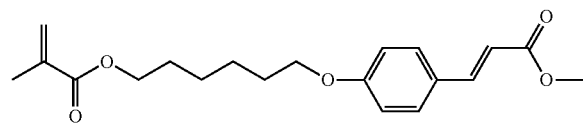 [SMILES: C=C(C)C(=O)OCCCCCCOc1ccc(/C=C/C(=O)OC)cc1]

6-{4-[(1E)-3-methoxy-3-oxoprop-1-enyl]phenoxy}hexyl 2-methylacrylate is prepared according the same procedure following for example 4 of U.S. Pat. No. 6,107,427.

Preparation of poly 6-{4-[(1E)-3-methoxy-3-oxoprop-1-enyl]phenoxy}hexyl 2-methylacrylate-co-11-{4-[(Z)-2-(1,3-benzodioxol-5-yl)-2-cyanoethenyl]-2-methoxyphenoxy}undecyl 2-methylacrylate (Monomer Weight Ratio 99:1)

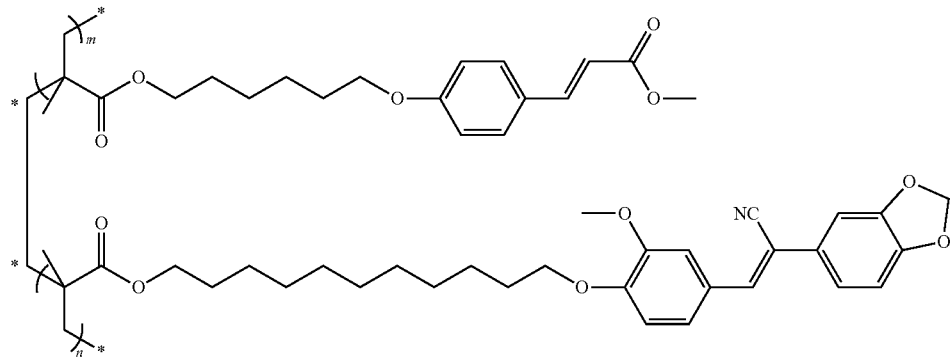

Poly 6-{4-[(1E)-3-methoxy-3-oxoprop-1-enyl]phenoxy}hexyl 2-methylacrylate-co-11-{4-[(Z)-2-(1,3-benzodioxol-5-yl)-2-cyanoethenyl]-2-methoxyphenoxy}undecyl 2-methylacrylate (monomer weight ratio 99:1) is prepared starting from 99 parts of 6-{4-[(1E)-3-methoxy-3-oxoprop-1-enyl]phenoxy}hexyl 2-methylacrylate and 1 part of 11-{4-[(Z)-2-(1,3-benzodioxol-5-yl)-2-cyanoethenyl]-2-methoxyphenoxy}undecyl 2-methylacrylate according the same procedure following for example 1 in 87% yield. The material displays spectral characteristic consistent with its assigned structure. Size-exclusion chromatography (PS-equivalent), Mn 52,516; Mw 161,210; PDI 3.1.

Example 24

Synthesis of poly 6-{4-[(1E)-3-methoxy-3-oxoprop-1-enyl]phenoxy}hexyl 2-methylacrylate-co-11-{4-[(Z)-2-(1,3-benzodioxol-5-yl)-2-cyanoethenyl]-2-methoxyphenoxy}undecyl 2-methylacrylate (monomer weight ratio 98:2)

Poly 6-{4-[(1E)-3-methoxy-3-oxoprop-1-enyl]phenoxy}hexyl 2-methylacrylate-co-11-{4-[(Z)-2-(1,3-benzodioxol-5-yl)-2-cyanoethenyl]-2-methoxyphenoxy}undecyl 2-methylacrylate (monomer weight ratio 98:2) is prepared starting from 98 parts of -{4-[(1E)-3-methoxy-3-oxoprop-1-enyl]phenoxy}hexyl 2-methylacrylate and 2 part of 11-{4-[(Z)-2-(1,3-benzodioxol-5-yl)-2-cyanoethenyl]-2-methoxyphenoxy}undecyl 2-methylacrylate according the same procedure following for example 1 in 88% yield. The material displays spectral characteristic consistent with its assigned structure. Size-exclusion chromatography (PS-equivalent), Mn 60,934; Mw 183,254; PDI 3.0.

Example 25

Synthesis of poly 6-{4-[(1E)-3-methoxy-3-oxoprop-1-enyl]phenoxy}hexyl 2-methylacrylate-co-11-{4-[(Z)-2-(1,3-benzodioxol-5-yl)-2-cyanoethenyl]-2-methoxyphenoxy}undecyl 2-methylacrylate (monomer weight ratio 97:3)

Poly 6-{4-[(1E)-3-methoxy-3-oxoprop-1-enyl]phenoxy}hexyl 2-methylacrylate-co-11-{4-[(Z)-2-(1,3-benzodioxol-5-yl)-2-cyanoethenyl]-2-methoxyphenoxy}undecyl 2-methylacrylate (monomer weight ratio 97:3) is prepared starting from 97 parts of 6-{4-[(1E)-3-methoxy-3-oxoprop-1-enyl]phenoxy}hexyl 2-methylacrylate and 3 part of 11-{4-[(Z)-2-(1,3-benzodioxol-5-yl)-2-cyanoethenyl]-2-methoxyphenoxy}undecyl 2-methylacrylate according the same procedure following for example 1 in 87% yield. The material displays spectral characteristic consistent with its assigned structure. Size-exclusion chromatography (PS-equivalent), Mn 35,185; Mw 134,656; PDI 3.8.

Example 26

Synthesis of poly 6-{4-[(1E)-3-methoxy-3-oxoprop-1-enyl]phenoxy}hexyl 2-methylacrylate-co-11-{4-[(Z)-2-cyano-2-(3,4-dimethoxyphenyl)ethenyl]-2-methoxyphenoxy}undecyl 2-methylacrylate (monomer weight ratio 97:3)

Preparation of 11-{4-[(Z)-2-cyano-2-(3,4-dimethoxyphenyl)ethenyl]-2-methoxyphenoxy}undecyl 2-methylacrylate
11-{4-[(Z)-2-cyano-2-(3,4-dimethoxyphenyl)ethenyl]-2-methoxyphenoxy}undecyl 2-methylacrylate is prepared according the same procedure following examples of U.S. Pat. No. 7,959,990.

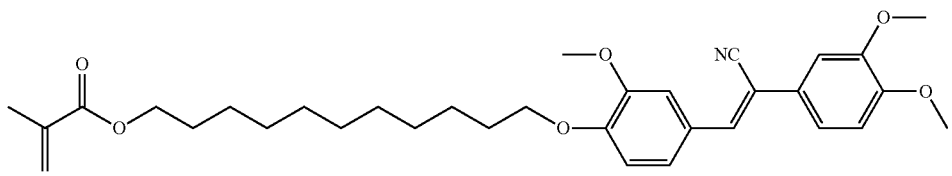 [SMILES: C=C(C)C(=O)OCCCCCCCCCCCOc1ccc(/C=C(\C#N)c2ccc(OC)c(OC)c2)cc1OC]

Preparation of poly 6-{4-[(1E)-3-methoxy-3-oxoprop-1-enyl]phenoxy}hexyl 2-methylacrylate-co-11-{4-[(Z)-2-cyano-2-(3,4-dimethoxyphenyl)ethenyl]-2-methoxyphenoxy}undecyl 2-methylacrylate (monomer weight ratio 97:3)

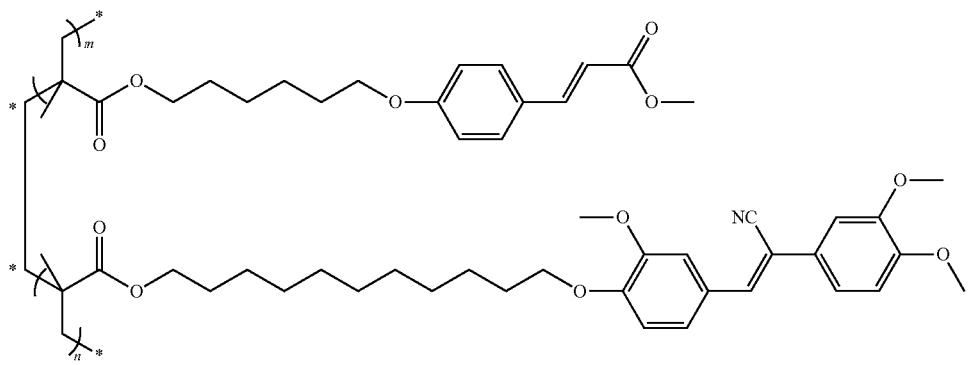

Poly 6-{4-[(1E)-3-methoxy-3-oxoprop-1-enyl]phenoxy}hexyl 2-methylacrylate-co-11-{4-[(Z)-2-cyano-2-(3,4-dimethoxyphenyl)ethenyl]-2-methoxyphenoxy}undecyl 2-methylacrylate (monomer weight ratio 97:3) is prepared starting from 97 parts of 6-{4-[(1E)-3-methoxy-3-oxoprop-1-enyl]phenoxy}hexyl 2-methylacrylate and 3 part of 11-{4-[(Z)-2-cyano-2-(3,4-dimethoxyphenyl)ethenyl]-2-methoxyphenoxy}undecyl 2-methylacrylate according the same procedure following for example 1 in 91% yield. The material displays spectral characteristic consistent with its assigned structure. Size-exclusion chromatography (PS-equivalent), Mn 41,812; Mw 186,091; PDI 4.5.

Example 27

Synthesis poly 6-{4-[(1E)-3-methoxy-3-oxoprop-1-enyl]phenoxy}hexyl 2-methylacrylate-co-11-{4-[(Z)-2-(1,3-benzodioxol-5-yl)-2-cyanoethenyl]-2-ethoxyphenoxy}undecyl 2-methylacrylate (monomer weight ratio 97:3)

Preparation of 3-ethoxy-4-[(11-hydroxyundecyl)oxy]benzaldehyde

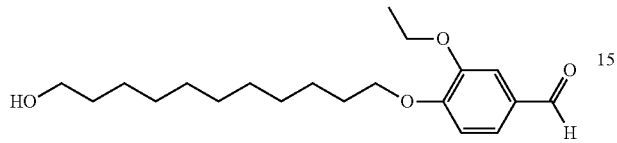

3-ethoxy-4-[(11-hydroxyundecyl)oxy]benzaldehyde is prepared starting from 3-ethoxy-4-hydroxybenzaldehyde and 11-bromoundecan-1-ol according the same procedure following for example 7 in 95% yield. This material proves chromatographically homogenous and displays spectral characteristics consistent with its assigned structure.

Preparation of (2Z)-2-(1,3-benzodioxol-5-yl)-3-{3-ethoxy-4-[(11-hydroxyundecyl)oxy]phenyl}prop-2-enenitrile

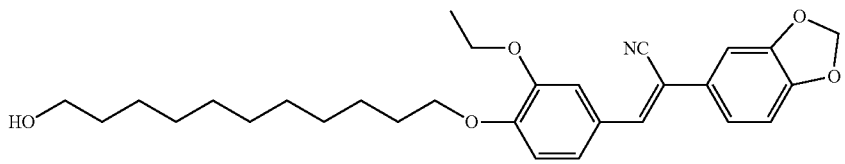 [SMILES: CCOc1cc(/C=C(\C#N)c2ccc3c(c2)OCO3)ccc1OCCCCCCCCCCCO]

(2Z)-2-(1,3-benzodioxol-5-yl)-3-{3-ethoxy-4-[(11-hydroxyundecyl)oxy]phenyl}prop-2-enenitrile is prepared from 3-ethoxy-4-[(11-hydroxyundecyl)oxy]benzaldehyde and 1,3-benzodioxol-5-ylacetonitrile according the same procedure following for example 10 in 96% yield. This material proves chromatographically homogenous and displays spectral characteristics consistent with its assigned structure.

Preparation of 11-{4-[(Z)-2-(1,3-benzodioxol-5-yl)-2-cyanoethenyl]-2-ethoxyphenoxy}undecyl 2-methylacrylate

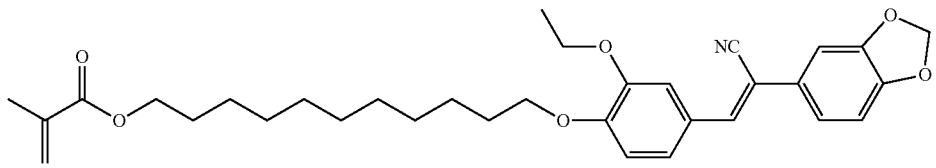 [SMILES: C=C(C)C(=O)OCCCCCCCCCCCOc1ccc(/C=C(\C#N)c2ccc3c(c2)OCO3)cc1OCC]

11-{4-[(Z)-2-(1,3-benzodioxol-5-yl)-2-cyanoethenyl]-2-ethoxyphenoxy}undecyl 2-methylacrylate is prepared starting from (2Z)-2-(1,3-benzodioxol-5-yl)-3-{3-ethoxy-4-[(11-hydroxyundecyl)oxy]phenyl}prop-2-enenitrile according the same procedure following for example 1 in 87% yield $^1$H NMR CDCl$_3$ 300 MHz: 7.67 (d, 1H), 7.33 (m, 2H), 7.19 (m, 2H), 6.93 (m, 2H), 6.11 (s, 1H), 6.03 (s, 2H), 5.57 (m, 1H), 4.19 (m, 4H), 4.08 (t, 2H), 1.96 (s, 3H), 1.90 (m, 2H), 1.70 (m, 2H), 1.66-1.31 (m, 17H)

Preparation of 6-{4-[(1E)-3-methoxy-3-oxoprop-1-enyl]phenoxy}hexyl 2-methylacrylate-co-11-{4-[(Z)-2-(1,3-benzodioxol-5-yl)-2-cyanoethenyl]-2-ethoxyphenoxy}undecyl 2-methylacrylate (monomer weight ratio 97:3)

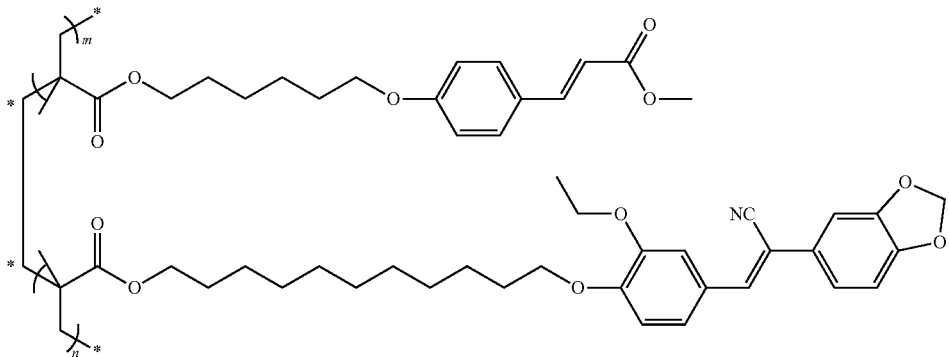

Poly 6-{4-[(1E)-3-methoxy-3-oxoprop-1-enyl]phenoxy}hexyl 2-methylacrylate-co-11-{4-[(Z)-2-(1,3-benzodioxol-5-yl)-2-cyanoethenyl]-2-ethoxyphenoxy}undecyl 2-methylacrylate (monomer weight ratio 97:3) is prepared starting from 97 parts 6-{4-[(1E)-3-methoxy-3-oxoprop-1-enyl]phenoxy}hexyl 2-methylacrylate and 3 part of 11-{4-[(Z)-2-(1,3-benzodioxol-5-yl)-2-cyanoethenyl]-2-ethoxyphenoxy}undecyl 2-methylacrylate according the same procedure following for example 1 in 91% yield. The material displays spectral characteristic consistent with its assigned structure. Size-exclusion chromatography (PS-equivalent), Mn 40,077; Mw 177,655; PDI 4.4.

Example 28

Synthesis poly 6-{4-[(1E)-3-methoxy-3-oxoprop-1-enyl]phenoxy}hexyl 2-methylacrylate-co-6-{4-[(Z)-2-(1,3-benzodioxol-5-yl)-2-cyanoethenyl]-2,6-dimethoxyphenoxy}hexyl 2-methylacrylate (monomer weight ratio 97:3)

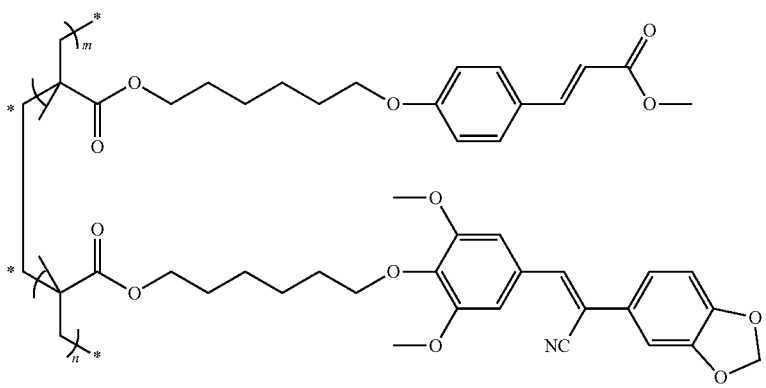

Poly 6-{4-[(1E)-3-methoxy-3-oxoprop-1-enyl]phenoxy}hexyl 2-methylacrylate-co-6-{4-[(Z)-2-(1,3-benzodioxol-5-yl)-2-cyanoethenyl]-2,6-dimethoxyphenoxy}hexyl 2-methylacrylate (monomer weight ratio 97:3) is prepared starting from 97 parts of 6-{4-[(1E)-3-methoxy-3-oxoprop-1-enyl]phenoxy}hexyl 2-methylacrylate and 3 part of 6-{4-[(Z)-2-(1,3-benzodioxol-5-yl)-2-cyanoethenyl]-2,6-dimethoxyphenoxy}hexyl 2-methylacrylate according the same procedure following for example 1 in 89% yield. The material displays spectral characteristic consistent with its assigned structure. Size-exclusion chromatography (PS-equivalent), Mn 39,943; Mw 268,604; PDI 6.7.

Example 29

Synthesis poly 6-{4-[(1E)-3-methoxy-3-oxoprop-1-enyl]phenoxy}hexyl 2-methylacrylate-co-6-{4-[(Z)-2-cyano-2-(3,4-dimethoxyphenyl)ethenyl]-2,6-dimethoxyphenoxy}hexyl 2-methylacrylate (monomer weight ratio 97:3)

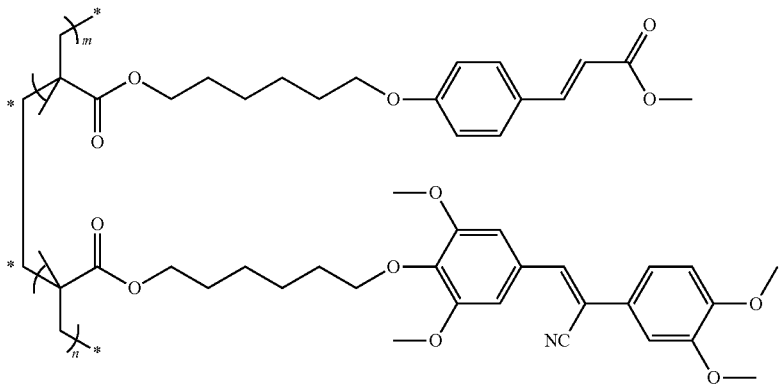

Poly 6-{4-[(1E)-3-methoxy-3-oxoprop-1-enyl]phenoxy}hexyl 2-methylacrylate-co-6-{4-[(Z)-2-cyano-2-(3,4-dimethoxyphenyl)ethenyl]-2,6-dimethoxyphenoxy}hexyl 2-methylacrylate (monomer weight ratio 97:3) is prepared starting from 97 parts of 6-{4-[(1E)-3-methoxy-3-oxoprop-1-enyl]phenoxy}hexyl 2-methylacrylate and 3 part of 6-{4-[(Z)-2-cyano-2-(3,4-dimethoxyphenyl)ethenyl]-2,6-dimethoxyphenoxy}hexyl 2-methylacrylate according the same procedure following for example 1 in 91% yield. The material displays spectral characteristic consistent with its assigned structure. Size-exclusion chromatography (PS-equivalent), Mn 33,825; Mw 132,562; PDI 3.9.

Example 30

Synthesis poly 6-{4-[(1E)-3-methoxy-3-oxoprop-1-enyl]phenoxy}hexyl 2-methylacrylate-co-6-{4-[(Z)-2-cyano-2-(3,4-dimethoxyphenyl)ethenyl]-2-ethoxyphenoxy}hexyl 2-methylacrylate (monomer weight ratio 97:3)

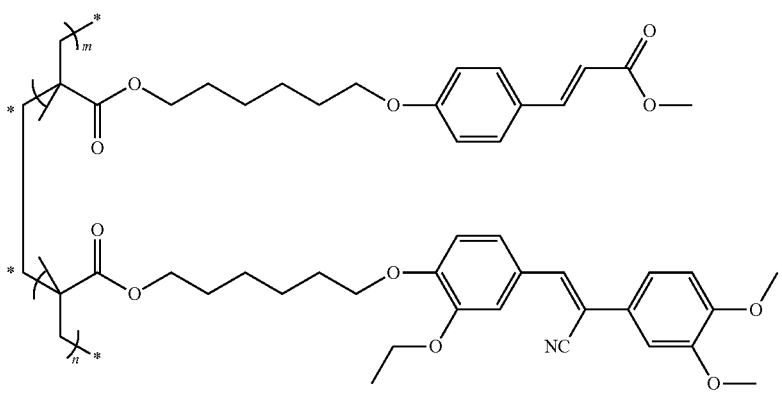

Poly 6-{4-[(1E)-3-methoxy-3-oxoprop-1-enyl]phenoxy}hexyl 2-methylacrylate-co-6-{4-[(Z)-2-cyano-2-(3,4-dimethoxyphenyl)ethenyl]-2-ethoxyphenoxy}hexyl 2-methylacrylate (monomer weight ratio 97:3) is prepared starting from 97 parts of 6-{4-[(1E)-3-methoxy-3-oxoprop-1-enyl]phenoxy}hexyl 2-methylacrylate and 3 part of 6-{4-[(Z)-2-cyano-2-(3,4-dimethoxyphenyl)ethenyl]-2-ethoxyphenoxy}hexyl 2-methylacrylate according the same procedure following for example 1 in 93% yield. The material displays spectral characteristic consistent with its assigned structure. Size-exclusion chromatography (PS-equivalent), Mn 36,300; Mw 142,326; PDI 3.9.

B) Application Examples

Example 31

Application as Photoalignment Material

This example illustrates how an alignment layer can be made of a material comprising functionalized photoreactive compounds according to the invention. A two percent by weight solution S1 of the photoreactive polymer formulation is prepared using cyclopentanone as solvent. The solution is stirred for 30 minutes at room temperature and filtered on 0.20 µm PTFE hi-cap (full name has to be given). The solution is spin-coated at 2000 rpm onto a glass substrate, which is then dried for 5 minutes at 180° C. The substrate is subsequently irradiated with polarized UVA light from a mercury high-pressure lamp, the direction of incidence being perpendicular to the substrate surface. For the polarization a Moxtec polarizer is used. By varying the exposure duration, different irradiation energies of 2, 4, 8, 12, 16 and 32 mJ·cm$^{-2}$ are applied. A liquid crystal photo-polymerisable monomer solution S2 made from 29.1 wt % LCM1, 0.3 wt % photoinitiator IRGACURE™ 369 from Ciba SC, 0.3 wt % of Tinuvine 123, and 0.3 wt % of BHT, is prepared using anisole as solvent. The solution is stirred for 30 minutes at room temperature and filtered on 0.20 μm PTFE hi-cap.

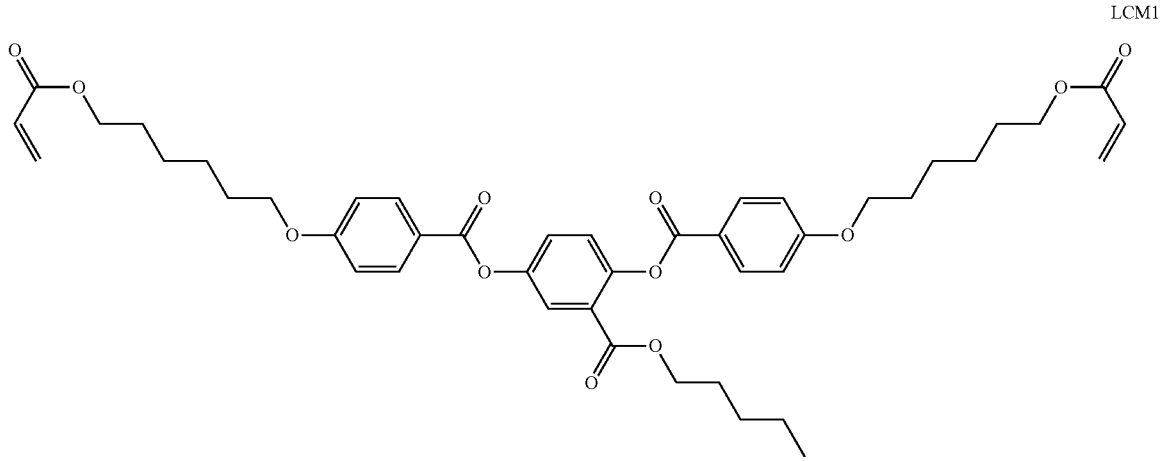 [SMILES: C=CC(=O)OCCCCCCOc1ccc(C(=O)Oc2ccc(OC(=O)c3ccc(OCCCCCCOC(=O)C=C)cc3)c(C(=O)OCCCCC)c2)cc1]

LCM1

The solution is spin-coated at 800 rpm onto the substrate, which is then dried for 30 seconds at 50° C. The substrate is subsequently irradiated with isotropic UV light under nitrogen atmosphere for 30 seconds. Between crossed polarizers, the minimum energy needed to obtain a LCP layer well aligned is determined for each compound. Contrast at this specific energy and azimuthal stability i.e. comparison of the resulting angle after double exposure with 128 mJ·cm$^{-2}$ at 0° and 45° are measured. The following table resumes the results obtained for examples 1 to 19.

| Sample | $E_{min}$ for orientation [mJ · cm$^{-2}$]/ irradiation time for a 1.5 mJ · cm$^{-2}$ [s] |
|---|---|
| Example 1 | 32/23.3 |
| Example 2 | 12/8 |
| Example 4 | 4/2.7 |
| Example 5 | 60/40 |
| Example 6 | 8/5.3 |
| Example 7 | 2/1.3 |
| Example 8 | 8/5.3 |
| Example 9 | 8/5.3 |
| Example 10 | 8/5.3 |
| Example 11 | 8/5.3 |
| Example 12 | 4/2.7 |
| Example 13 | 8/5.3 |
| Example 14 | 8/5.3 |
| Example 15 | 4/2.7 |
| Example 16 | 8/5.3 |
| Example 17 | 4/2.7 |
| Example 18 | 16/10.6 |
| Example 19 | 16/10.6 |

| Sample | Contrast with $E_{min}$ |
|---|---|
| Example 1 | 1900 |
| Example 2 | 4300 |
| Example 3 | 400 |
| Example 4 | 1400 |
| Example 7 | 1000 |
| Example 8 | 3200 |
| Example 9 | 2300 |
| Example 10 | 3300 |
| Example 11 | 2700 |
| Example 12 | 2650 |

| Sample | Azimuthal stability angle 128 mJ · cm−2 [°] |
|---|---|
| Example 1 | 13.5 |
| Example 2 | 3.5 |
| Example 4 | 6.5 |
| Example 7 | 6.5 |
| Example 8 | 5.5 |

Example 32

A liquid crystal cell was prepared as described in the procedure below, wherein the liquid crystal is aligned by photo reactive PAA-1.

A 4.0 wt % solution of polyamic acid PAA-1 was prepared by mixing the solid polyamic acid PAA-1 in NMP and stirred thoroughly till the solid polyamic acid PAA-1 is dissolved. A second solvent 2-butoxyethanol (BC) is added and the whole composition is stirred thoroughly to obtain final solution. The solvent ratio between NMP and butyl cellulose is 1:1. The above polymer solution was spin-coated onto the two ITO coated glass substrates at a spin speed of 1700 rpm for 30 seconds. After spin coating the substrates were subjected to baking procedure consisting of pre-baking for 1.5 minutes at 130° C. and post-baking for 40 minutes at a temperature of 200° C. The resulting layer thickness was around 70 nm. The substrates with the coated polymer layer on top were exposed to linearly polarized UV light (LPUV) at an incidence angle of 40° relative to the normal of the substrate surface. The plane of polarization was within the plane spanned by the substrate normal and the propagation direction of the light. The applied exposure dose was 100 mJ/cm$^2$. After LPUV exposure a cell was assembled with the 2 substrates, the exposed polymer layers facing to the inside of the cell. The substrates were adjusted relative to each other such that the induced alignment directions were parallel to each other (corresponds to the anti-parallel, i.e 180°, rubbed configuration in case of alignment by rubbing procedure). The cell was capillary filled with liquid crystal MLC3005 (Merck KGA), which had a positive dielectric anisotropy. After that, the cell is optionally annealed at about 92° for 10 minutes and slowly cooled down to room temperature. The liquid crystal in the cell showed well defined and homogeneous planar orientation before and after thermal annealing of the cell. A tilt angle of about 0.26° was measured using the rotating analyzer method from Shintech.

Example 33

Application as Photoalignment Material on Unprotected TAC (Cellulose Triacetate) Film In these examples the alignment layer is based on photo-reactive copolymers following the synthesis cited in the invention. A 3 wt % solution S3 is prepared using a mixture of butyl acetate/ethyl acetate 1:1 as solvent. The blend is stirred until all the solid is dissolved and the solution is homogeneous and filtered on 0.20 μm PTFE Sartorius filter. The solution is applied on a TAC foil using a control coater and meter bar. The coated TAC film is dried for 1 min in an oven at 80° C. and exposed to polarized UV irradiation with different energies from 10 to 100 mJ·cm$^{-2}$ in the UV-B range. Subsequently a solution of photo-polymerisable liquid crystal monomer, S4, made with 30 wt % liquid crystal formulation using butyl acetate as solvent, is applied on the photo-aligned layer. The coated TAC is dried for 1 min at 55 C and oriented by reaction under isotropic UV light, 1500 mJ·cm$^{-2}$ and under N$_2$. The alignment quality is checked between crossed polarizers and lowest energy dose defined for each product in the considered conditions. The table below presents results of application tests using some materials cited in the present invention.

| Sample | $E_{min}$ for orientation [mJ · cm$^{-2}$] |
|---|---|
| Example 23 | 20 |
| Example 24 | 20 |
| Example 25 | 20 |
| Example 26 | 20 |
| Example 27 | 40 |
| Example 28 | 20 |
| Example 29 | 20 |
| Example 30 | 20 |

The invention claimed is:

1. A compound comprising a terminal group of formula (Ia)

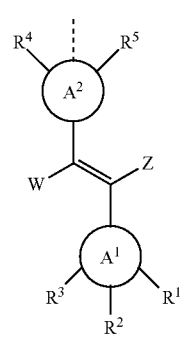

wherein:
the dotted line means a linkage of the terminal group to a residue of the compound;
A$^1$ and A$^2$ each independently are a ring system of 5 to 40 atoms, wherein each ring system includes at least one unsaturated bond directly connected via electron π-π conjugation bonding to the double bond shown in formula (Ia); and wherein A$^2$ is linked to a polymerizable group by a single bond or at least one spacer unit;
R$^1$ is hydrogen;
and wherein if
W is hydrogen and Z is an electron withdrawing group —CN, then
R$^4$, R$^5$ are independently from each other hydrogen or an alkoxy; and
R$^2$ and R$^3$ form together the residue of an electron-donating ring, wherein the residue of the electron-donating ring is —O-ethylene-O—, -ethylene-O— or —O-methylene-O—, which is condensed to ring A$^1$;
or if W is an electron withdrawing group —CN and Z is hydrogen, then
R$^4$, R$^5$ are independently from each other hydrogen or an alkoxy, and R$^2$ and R$^3$ form together the residue of an electron-donating ring, wherein the residue of the electron-donating ring is —O-ethylene-O—, -ethylene-O— or —O-methylene-O—, which is condensed to ring A$^1$.

2. The compound comprising the terminal group of formula (Ia) according to claim 1, wherein the polymerizable group is "D", which is selected from the group consisting of acrylate, methacrylate, 2-chloroacrylate, 2-phenylacrylate, optionally N-lower alkyl substituted acrylamide, methacrylamide, 2-chloroacrylamide, 2-phenylacrylamide, vinyl ether and ester, allyl ether and ester epoxy, styrene and styrene derivatives selected from the group consisting of alpha-methylstyrene, p-methylstyrene, p-tert-butyl styrene, and p-chlorostyrene, siloxanes, diamines, imide monomers, amic acid monomers and their esters, amidimide monomers, maleic acid and maleic acid derivatives selected from the group consisting of di-n-butyl maleate, dimethyl maleate, and diethyl maleate, fumaric acid and fumaric acid derivatives selected from the group consisting of di-n-butyl fumarate and di-(2-ethylhexyl) fumarate, and urethanes.

3. The compound comprising the terminal group of formula (Ia) according to claim 1, wherein the spacer units are S$^1$ and S$^2$ each independently from each other represents a single bond or a cyclic, straight-chain or branched, substituted or unsubstituted C$_1$-C$_{24}$alkylene, in which one or more C-atom, CH— or CH$_2$— group unreplaced or replaced by a linking group, or a non-aromatic, aromatic, unsubstituted or substituted carbocyclic or heterocyclic group of formula (V):

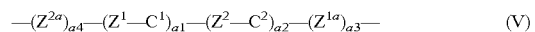

wherein:
C$^1$, C$^2$ each independently represents an alicyclic or aromatic, unsubstituted or substituted carbocyclic group or a heterocyclic group connected to each other via a group Z$^1$, Z$^2$, Z$_{1a}$, Z$^{2a}$, or various combinations thereof and Z$^1$, Z$^2$Z$^{2a}$ each independently represents a bridging group which is —CH(OH)—, —O—, —CH$_2$(CO)—, —SO—, —CH$_2$(SO)—, —SO$_2$—, —CH$_2$(SO$_2$)—, —COO—, —OCO—, —COF$_2$—, —CF$_2$CO—, —S—CO—, —CO—S—, —SOO—, —OSO—,—CH$_2$—, —CH$_2$—,O—CH$_2$—, —CH$_2$—, —O—CH$_2$—, —CH$_2$O—, —, —CH═CH—, —C═S——SH═CH—COO—, —OCO—CH═CH—, —CH═N—, —C(CH$_3$)═N—, —O—CO—O—, —N═N—, or an alkylene spacer of 1 to 6 carbon atoms, and a1, a2, a3, a4 each independently represents an integer from 0 to 3, such that a1+a2 +a3+a4≤6.

4. The compound according to claim 1 which is part of an oligomer, a dendrimer or a polymer, which may be a homopolymer or a copolymer.

5. An oligomer, dendrimer, copolymer or polymer comprising at least one compound according to claim 1 in its polymerized form as monomer unit.

6. The oligomer, dendrimer, copolymer or polymer according to claim 5 further comprising additives selected from the group consisting of silane-containing compounds, epoxy-containing crosslinking agents, a photosensitiser, a photo-radical generator and a cationic photoinitiator.

7. The oligomer, dendrimer, copolymer or polymer according to claim 5 further comprising in admixture other polymers, oligomers, monomers, photoactive polymers, photoactive oligomers and/or photoactive monomers.

8. The oligomer, dendrimer, copolymer or polymer according to claim 5 which is applied to a support and reacted by irradiation with aligning light.

9. A composition comprising an oligomer, dendrimer, copolymer or polymer according to claim 5.

10. A method of using one or more oligomers, dendrimers, copolymer or polymers according to claim 5, comprising providing said one or more oligomers, dendrimers, copolymer or polymers as an alignment layer for polymerizable liquid crystals or switchable liquid crystals.

11. An alignment layer comprising one or more oligomers, dendrimers, copolymer or polymers claim 5.

12. The alignment layer according to claim 11 having a pattern of different alignment directions.

13. A method for the preparation of an alignment layer according to claim 11, wherein one or more of the oligomers, dendrimers, copolymer or polymers, preferably in solution, is applied to a support, which is optionally provided with an electrode, and optionally after prior imidisation, said applied oligomers, dendrimers or polymers are reacted by irradiation with aligning light and optionally subsequently bringing into contact said alignment layer with a composition comprising polymerizable liquid crystals.

14. The method according to claim 13 wherein the alignment direction is controlled by photoalignment methods.

15. Optical and electro-optical unstructured or structured constructional elements comprising at least one alignment layer according to claim 11.

16. Optical and electro-optical unstructured or structured constructional elements according to claim 15, represented by multilayer systems, or devices for the preparation of a display waveguide, a security or brand protection element, a bar code, an optical grating, a filter, a retarder, a compensation film, a reflectively polarizing film, an absorptive polarizing film, an anisotropically scattering film compensator and retardation film, 3-D retarder, a twisted retarder film, a cholesteric liquid crystal film, a guest-host liquid crystal film, a monomer corrugated film, a smectic liquid crystal film, a polarizer, a piezoelectric cell, a thin film exhibiting non linear optical properties, a decorative optical element, a brightness enhancement film, a component for wavelength-band-selective compensation, a component for multi-domain compensation, a component of multiview liquid crystal displays, an achromatic retarder, a polarization state correction adjustment film, a component of optical or electro-optical sensors, a component of brightness enhancement film, a component for light-based telecommunication devices, a G/H-polarizer with an anisotropic absorber, a reflective circular polarizer, a reflective linear polarizer, a MC (monomer corrugated film), twisted nematic (TN) liquid crystal displays, hybrid aligned nematic (HAN) liquid crystal displays, electrically controlled birefringence (ECB) liquid crystal displays, supertwisted nematic (STN) liquid crystal displays, optically compensated birefringence (OCB) liquid crystal displays, pi-cell liquid crystal displays, in-plane switching (IPS) liquid crystal displays, fringe field switching (FFS) liquid crystal displays; (PSVA) polymer stabilised vertically aligned; (FPA) field-induced photo-reactive alignment; hybrid FPA; vertically aligned (VA), (PVA) patterned VA; VA-IPS mode or liquid crystal displays, or displays using blue phase liquid crystals; all above display types are applied in either transmissive or reflective or transflective mode.

17. The compound comprising a group terminal group of formula (Ia) according to claim 1, W is hydrogen and Z is an electron withdrawing group, —CN.

18. The compound comprising a group terminal group of formula (Ia) according to claim 1, W is an electron withdrawing group, —CN and Z is hydrogen.

* * * * *